US010980760B2

(12) United States Patent
Chandraratna et al.

(10) Patent No.: US 10,980,760 B2
(45) Date of Patent: Apr. 20, 2021

(54) TREATMENT OF NERVOUS SYSTEM DISORDERS USING COMBINATIONS OF RXR AGONISTS AND THYROID HORMONES

(71) Applicant: Io Therapeutics, Inc., Houston, TX (US)

(72) Inventors: Roshantha A. Chandraratna, San Juan Capistrano, CA (US); Martin E. Sanders, Seattle, WA (US)

(73) Assignee: Io Therapeutics, Inc., Houston, TX (US)

( * ) Notice: Subject to any disclaimer, the term of this patent is extended or adjusted under 35 U.S.C. 154(b) by 0 days.

(21) Appl. No.: 16/742,354

(22) Filed: Jan. 14, 2020

(65) Prior Publication Data
US 2020/0147023 A1    May 14, 2020

Related U.S. Application Data

(60) Continuation of application No. 16/364,653, filed on Mar. 26, 2019, now Pat. No. 10,842,764, which is a division of application No. 16/118,001, filed on Aug. 30, 2018, now Pat. No. 10,485,778, which is a continuation of application No. 15/812,821, filed on Nov. 14, 2017, now Pat. No. 10,278,932, which is a continuation of application No. 15/339,752, filed on Oct. 31, 2016, now Pat. No. 9,877,941.

(60) Provisional application No. 62/249,216, filed on Oct. 31, 2015.

(51) Int. Cl.
| *A61K 31/198* | (2006.01) |
| *A61P 25/28* | (2006.01) |
| *A61P 25/16* | (2006.01) |
| *A61K 31/455* | (2006.01) |
| *A61K 45/06* | (2006.01) |
| *A61P 25/00* | (2006.01) |
| *A61K 9/00* | (2006.01) |
| *A61K 31/192* | (2006.01) |
| *A61K 31/4418* | (2006.01) |
| *A61K 9/48* | (2006.01) |

(52) U.S. Cl.
CPC .......... *A61K 31/198* (2013.01); *A61K 9/0043* (2013.01); *A61K 9/0053* (2013.01); *A61K 31/192* (2013.01); *A61K 31/4418* (2013.01); *A61K 31/455* (2013.01); *A61K 45/06* (2013.01); *A61P 25/00* (2018.01); *A61P 25/16* (2018.01); *A61P 25/28* (2018.01); *A61K 9/0019* (2013.01); *A61K 9/48* (2013.01)

(58) Field of Classification Search
CPC .......... A61K 31/198; A61P 25/28; A61P 25/00
See application file for complete search history.

(56) References Cited

U.S. PATENT DOCUMENTS

| 4,756,911 A | 7/1988 | Drost |
| 5,378,475 A | 1/1995 | Smith |
| 5,455,265 A | 10/1995 | Chandraratna |
| 5,466,861 A | 11/1995 | Dawson et al. |
| 5,663,367 A | 9/1997 | Vuligonda et al. |
| 5,675,033 A | 10/1997 | Vuligonda et al. |
| 5,728,846 A | 3/1998 | Vuligonda et al. |
| 5,739,338 A | 4/1998 | Beard et al. |
| 5,763,635 A | 6/1998 | Vuligonda et al. |
| 5,773,594 A | 6/1998 | Johnson et al. |
| 5,776,699 A | 7/1998 | Klein et al. |
| 5,780,647 A | 7/1998 | Vuligonda et al. |
| 5,817,836 A | 10/1998 | Vuligonda et al. |
| 5,856,490 A | 1/1999 | Teng |
| 5,877,207 A | 3/1999 | Klein et al. |
| 5,917,082 A | 6/1999 | Vuligonda et al. |
| 5,919,970 A | 7/1999 | Song et al. |
| 5,952,345 A | 9/1999 | Klein et al. |
| 5,958,954 A | 9/1999 | Klein et al. |
| 5,965,606 A | 10/1999 | Teng |
| 5,998,655 A | 12/1999 | Vuligonda et al. |
| 6,008,204 A | 12/1999 | Klein et al. |
| 6,048,873 A | 1/2000 | Vasudevan et al. |
| 6,034,242 A | 3/2000 | Vuligonda et al. |
| 6,037,488 A | 3/2000 | Song et al. |
| 6,043,381 A | 3/2000 | Vuligonda et al. |
| 6,063,768 A | 5/2000 | First |
| 6,087,505 A | 7/2000 | Vuligonda et al. |
| 6,090,810 A | 7/2000 | Klein et al. |
| 6,114,533 A | 9/2000 | Vuligonda et al. |
| 6,117,987 A | 9/2000 | Johnson et al. |
| 6,147,224 A | 11/2000 | Vuligonda et al. |
| 6,187,750 B1 | 2/2001 | Chein |
| 6,211,385 B1 | 4/2001 | Vuligonda et al. |
| 6,218,128 B1 | 4/2001 | Klein et al. |

(Continued)

FOREIGN PATENT DOCUMENTS

| EP | 2322147 A1 | 5/2011 |
| EP | 2556827 A1 | 2/2013 |

(Continued)

OTHER PUBLICATIONS

Farvolden et. al. (Expert Opin. Investig. Drugs (2003) 12:65-86) (Year: 2003).*
Holtzheimer et. al. (Expert Opin. Pharmacother. (2006) 7:2323-2339). (Year: 2006).*
Russell et. all. (The International Journal of Neuropsychopharmacology (2000) 3:143-147). (Year: 2000).*
Madhu et. al. (International Journal of Pharmaceutical Sciences and Research (2013) 4:3731-3736) (Year: 2013).*
Saresella et al., PD1 negative and PD1 positive CD4+ T regulatory cells in mild cognitive impairment and Alzheimer's Disease. Journal of Alzheimer's Disease, 21:927-938 (2010).

(Continued)

*Primary Examiner* — Marcos L Sznaidman
(74) *Attorney, Agent, or Firm* — K&L Gates LLP; Louis C. Cullman; David Diamond

(57) ABSTRACT

Disclosed herein are methods of treating disease with a combination of a RXR agonist and a thyroid hormone.

30 Claims, 19 Drawing Sheets

(56) References Cited

U.S. PATENT DOCUMENTS

| | | |
|---|---|---|
| 6,225,494 B1 | 5/2001 | Song et al. |
| 6,228,848 B1 | 5/2001 | Klein et al. |
| 6,235,923 B1 | 5/2001 | Song et al. |
| 6,313,163 B1 | 11/2001 | Vuligonda et al. |
| 6,313,168 B1 | 11/2001 | Pacifici et al. |
| 6,387,950 B2 | 5/2002 | Nehme |
| 6,403,638 B1 | 6/2002 | Vuligonda et al. |
| 6,521,624 B1 | 2/2003 | Klein et al. |
| 6,521,641 B1 | 2/2003 | Klein et al. |
| 6,538,149 B1 | 3/2003 | Vuligonda et al. |
| 6,555,690 B2 | 4/2003 | Johnson et al. |
| 6,610,744 B2 | 8/2003 | Teng et al. |
| 6,630,463 B2 | 10/2003 | Kikuchi et al. |
| 6,653,483 B1 | 11/2003 | Johnson et al. |
| 6,720,423 B2 | 4/2004 | Vasudevan et al. |
| 6,720,425 B2 | 4/2004 | Johnson et al. |
| 6,776,984 B1 | 8/2004 | Schwartz |
| 6,818,775 B2 | 11/2004 | Johnson et al. |
| 6,942,980 B1 | 9/2005 | Klein et al. |
| 7,048,946 B1 | 5/2006 | Wong |
| 7,105,566 B2 | 9/2006 | Chandraratna et al. |
| 7,166,726 B2 | 1/2007 | Vuligonda et al. |
| 8,101,662 B2 | 1/2012 | Chandraratna |
| 9,308,186 B2 | 4/2016 | Chandraratna |
| 9,655,872 B2 | 5/2017 | Chandraratna |
| 9,717,702 B2 | 8/2017 | Chandraratna |
| 10,039,731 B2 | 8/2018 | Chandraratna |
| 10,188,618 B2 | 1/2019 | Chandraratna |
| 2001/0037025 A1 | 11/2001 | Murray et al. |
| 2002/0156054 A1 | 10/2002 | Klein et al. |
| 2002/0173631 A1 | 11/2002 | Johnson et al. |
| 2002/0193403 A1 | 12/2002 | Yuan et al. |
| 2003/0013766 A1 | 1/2003 | Lamph et al. |
| 2003/0077664 A1 | 4/2003 | Zhao et al. |
| 2003/0144330 A1 | 7/2003 | Spiegelman |
| 2003/0219832 A1 | 11/2003 | Klein et al. |
| 2004/0049072 A1 | 3/2004 | Ardecky |
| 2004/0147611 A1 | 7/2004 | Yuan et al. |
| 2004/0037025 A1 | 11/2004 | Murray et al. |
| 2005/0137134 A1 | 6/2005 | Gill et al. |
| 2005/0171151 A1 | 8/2005 | Yuan et al. |
| 2005/0181017 A1 | 8/2005 | Hughes |
| 2005/0244464 A1 | 11/2005 | Hughes |
| 2006/0286127 A1 | 12/2006 | Van Schaack et al. |
| 2007/0054882 A1 | 3/2007 | Klein et al. |
| 2007/0077652 A1 | 4/2007 | Peled et al. |
| 2007/0078129 A1 | 4/2007 | Lagu et al. |
| 2007/0122476 A1 | 5/2007 | Hanshew |
| 2007/0185055 A1 | 8/2007 | Jiang |
| 2007/0265449 A1 | 11/2007 | Vuligonda et al. |
| 2009/0004291 A1 | 1/2009 | Song |
| 2009/0136470 A1 | 5/2009 | Hilde et al. |
| 2009/0203720 A1 | 8/2009 | Zhao et al. |
| 2009/0227674 A1 | 9/2009 | Richon et al. |
| 2010/0298434 A1 | 11/2010 | Rouillard |
| 2011/0008437 A1 | 1/2011 | Altman |
| 2012/0115912 A1 | 5/2012 | Landreth |
| 2012/0238623 A1 | 9/2012 | Chandraratna |
| 2013/0190395 A1 | 7/2013 | Chandraratna et al. |
| 2014/0235676 A1 | 8/2014 | Landreth |
| 2014/0286973 A1 | 9/2014 | Powell, Jr. |
| 2015/0038585 A1 | 2/2015 | Chandraratna et al. |
| 2015/0196517 A1 | 7/2015 | Chandraratna et al. |
| 2015/0209549 A1 | 7/2015 | Gill |
| 2015/0342917 A1 | 12/2015 | Chandraratna et al. |
| 2017/0056348 A1 | 3/2017 | Chandraratna et al. |
| 2017/0119713 A1 | 5/2017 | Chandraratna et al. |
| 2017/0119714 A1 | 5/2017 | Chandraratna et al. |
| 2018/0064670 A1 | 3/2018 | Chandraratna et al. |
| 2018/0116985 A1 | 5/2018 | Chandraratna et al. |
| 2018/0263939 A1 | 9/2018 | Chandraratna et al. |
| 2018/0318241 A1 | 11/2018 | Chandraratna et al. |
| 2018/0369181 A1 | 12/2018 | Chandraratna et al. |
| 2019/0083441 A1 | 3/2019 | Chandraratna et al. |
| 2019/0117603 A1 | 4/2019 | Chandraratna |
| 2019/0125705 A1 | 5/2019 | Chandraratna et al. |
| 2019/0201358 A1 | 7/2019 | Chandraratna et al. |
| 2019/0209504 A1 | 7/2019 | Chandraratna et al. |
| 2019/0209505 A1 | 7/2019 | Chandraratna et al. |
| 2019/0216759 A1 | 7/2019 | Chandraratna et al. |
| 2019/0231726 A1 | 8/2019 | Chandraratna et al. |
| 2019/0240179 A1 | 8/2019 | Chandraratna et al. |
| 2019/0247348 A1 | 8/2019 | Chandraratna et al. |
| 2019/0247349 A1 | 8/2019 | Chandraratna et al. |
| 2019/0298678 A1 | 10/2019 | Chandraratna et al. |
| 2019/0365681 A1 | 12/2019 | Chandraratna et al. |
| 2019/0381022 A1 | 12/2019 | Chandraratna et al. |
| 2020/0147022 A1 | 5/2020 | Chandraratna et al. |
| 2020/0147024 A1 | 5/2020 | Chandraratna et al. |

FOREIGN PATENT DOCUMENTS

| | | |
|---|---|---|
| JP | 2010-280585 A | 12/2010 |
| WO | 1994/012880 A2 | 6/1994 |
| WO | 1994/014777 | 7/1994 |
| WO | 1996/039374 A1 | 12/1996 |
| WO | 1997/009297 A2 | 3/1997 |
| WO | 1999/033821 A1 | 7/1999 |
| WO | 1999/063980 A1 | 12/1999 |
| WO | 2000/020370 A1 | 4/2000 |
| WO | 2001/000662 A2 | 1/2001 |
| WO | 2001/007028 A2 | 2/2001 |
| WO | 2002/089781 A2 | 11/2002 |
| WO | 2002/089842 | 11/2002 |
| WO | 2003/062369 | 7/2003 |
| WO | 2003/078567 | 9/2003 |
| WO | 2003/093257 A1 | 11/2003 |
| WO | 2003/101928 | 12/2003 |
| WO | 2004/046096 | 6/2004 |
| WO | 2007/041076 A2 | 4/2007 |
| WO | 2007/041398 | 4/2007 |
| WO | 2008/157394 A2 | 12/2008 |
| WO | 2010/132671 A1 | 11/2010 |
| WO | 2011/006157 A2 | 1/2011 |
| WO | 2013/020966 | 2/2013 |
| WO | 2013/090616 A1 | 6/2013 |
| WO | 2015/059632 A1 | 4/2015 |
| WO | 2016/144976 A1 | 9/2016 |
| WO | 2017/075610 | 5/2017 |
| WO | 2017/075612 A1 | 5/2017 |
| WO | 2017/155577 A1 | 9/2017 |
| WO | 2017/155578 A1 | 9/2017 |
| WO | 2019/046591 A1 | 3/2019 |

OTHER PUBLICATIONS

Saresella et al., Increased activity of Th-17 and Th-9 lymphocytes and a skewing of the post-thymic differentiation pathway are seen in Alzheimer's disease. Brain, Behavior, and Immunity, 25:539-547 (2011).

Schneider et al., Hyperphosphorylation and aggregation of Tau in experimental autoimmune encephalomyelitis. The Journal of Biological Chemistry, vol. 279, No. 53, Issue of Dec. 31, pp. 55833-55839 (2004).

Shudo et al., Towards retinoid therapy for Alzheimer's disease. Current Alzheimer Research, 6:302-311 (2009).

Singh, Vijendra K., Neuroautoimmunity: pathogenic implications for Alzheimer's disease. Gerontology, 43:79-94 (1997).

Supplementary European Search Report for European Patent Application Serial No. 16861054 (PCT/US2016/059770) dated Jun. 13, 2019.

Taly, Antoine. Novel approaches to drug design for the treatment of schizophrenia. Expert Opinion on Drug Discovery, 8:10, pp. 1285-1296 (2013).

Wang et al., Splenocytes derived from young WT mice prevent AD progression in APPswe/PSENIdE9 transgenic mice. Oncotarget, vol. 6, No. 25, pp. 20851-20862 (2015).

Xiong et al., Investigational agents for treatment of traumatic brain injury. Expert Opinion Investigation Drugs, 24(6):743-760 (2015).

Zhang et al., Th17 cell-mediated neuroinflammation is involved in neurodegeneration of AB1-42-induced Alzheimer's disease model rats. PLOS One, vol. 8, Issue 10, p. e75786 (9 pp.) (2013).

(56) References Cited

OTHER PUBLICATIONS

Adalbert et al., Review: Axon pathology in age-related neurodegenerative disorders. Neuropathology and Applied Neurobiology, 39:90-108 (2013).
Butterfield et al., Redox proteomics: understanding oxidative stress in the progression of age-related neurodegenerative disorders. Expert Rev. Proteomics, 5(2):157-160 (2008).
Ayuso et al., Advanced neuroprotection for brain ischemia: an alternative approach to minimize stroke damage. Expert Opinion on Investigational Drugs, 24(9):1137-1142 (2015).
Hermann et al., Animal models of ischemic stroke and their impact on drug discovery. Expert Opinion on Drug Discovery, vol. 14, No. 3, pp. 315-326 (2019).
Singaporean Written Opinion dated Nov. 4, 2019 for Singaporean Application No. 11201803592X filed on Oct. 31, 2016.
Williams, Lawrence R. Oxidative stress, age-related neurodegeneration, and the potential for neurotrophic treatment. Cerebrovascular and Brain Metabolism Reviews, 7:55-73 (1995).
Silvestroff et al., Cuprizone-induced demyelination in the rat cerebral cortex and thyroid hormone effects on cortical remyelination. Experimental Neurology, 235, pp. 357-367 (2012).
Smit et al., Bexarotene-induced hypothrodism: bexarotene stimulates the peripheral metabolism of thyroid hormones. J. Clin. Endocrinol. Metab., 92(7):2496-2499 (2007).
Suh et al., Prevention and treatment of experimental breast cancer with the combination of a new selective estrogen receptor modulator, Arzoxifene, and a new rexinoid, LG 100268. Clin Cancer Res, 8:3270-3275 (2002).
Takahashi et al., Novel retinoid X receptor antagonists: specific inhibition of retinoid synergism in RXR-RAR heterodimer actions. Journal of Medicinal Chemistry, vol. 45, No. 16, pp. 3327-3330 (2002).
Teng et al., Identification of highly potent retinoic acid receptor alpha-selective antagonists. Journal of Medicinal Chemistry, vol. 40, pp. 2445-2451 (1997).
Tesseur et al., Comment on ApoE-directed Therapeutics Rapidly Clear beta-Amyloid and Reverse Deficits in AD Mouse Models. Science, 340:924-e (2013).
Tovar-Y-Romo et al., Trophic factors as modulators of motor neuron physiology and survival: implications for ALS therapy. Frontiers in Cellular Neuroscience, 8:Article 61 (2014).
Trillo et al., Ascending monoaminergic systems alterations in Alzheimer's disease. Translating basic science into clinical care. Neuroscience and Biobehavioral Riviews, 37:1363-1379 (2013).
Yap et al., The energy-redox axis in aging and age-related neurodegeneration. Advanced Drug Delivery Reviews, 61:1283-1298 (2009).
Aranami et al., Th17 cells and autoimmune encephalomyelitis (EAE/MS). Allergology International, 57:115-120 (2008).
Assaf et al., Minimizing adverse side-effects of oral bexarotene in cutaneous T-cell lymphoma: an expert opinion. British Journal of Dermatology, 155, pp. 261-266 (2006).
Baek et al., Neuroprotective effects of CD4+CD25+Foxp3+ regulatory T cells in a 3xTg-AD Alzheimer's disease model. Oncotarget, vol. 7, No. 43, pp. 69347-69357 (2016).
Banati et al., Inflammatory reaction in experimental autoimmune encephalomyelitis (EAE) is accompanied by a microglial expression of the BA4-amyloid precursor protein (APP). GLIA, 14:209-215 (1995).
Uslu et al., Doxazosin: a new cytotoxic agent for prostate cancer? BJU International, vol. 85, pp. 672-675 (2000).
Veeraraghavalu et al, Comment on ApoE-directed Therapeutics Rapidly Clear beta-Amyloid and Reverse Deficits in AD Mouse Models. Science 340:924-f, 2013.
Volakakis et al., Nurr1 and Retinoid X Receptor ligands stimulate Ret signaling in dopamine neurons and can alleviate alpha-synuclein disrupted gene expression. J. Neurosci., 35(42):14370-14385 (2015).

Walkley et al., Retinoic acid receptor anatagonism in vivo expands the numbers of precursor cells during granulopoiesis. Leukemia, vol. 16, No. 9, pp. 1763-1772 (2002).
Wallen-Mackenzie et al., Nurr1-RXR heterodimers mediate RXR ligand-induced signaling in neuronal cells. Genes and Development, 17: 3036-3047 (2003).
Wang et al., Selective brain penetrable Nurr1 transactivator for treating Parkinson's disease. Oncotarget 7(7):7469-7479 (2016).
Wang, (2013) Slide presentation at the Symposium on IRX4204 at The 11th International Conference on Alzheimer's and Parkinson's Diseases: The Novel RXR agonist IRX4204 as a Potential Disease-Modifying Agent in Alzheimer's Disease.
WebMD, Common Drugs and Medicines to Treat Multiple Sclerosis; Drugs & Medications Search, accessed May 12, 2017; pp. 1-3.
Xiao et al., Retinoic acid increases Foxp3+ regulatory T cells and inhibits development of TH17 cells by enhancing TFG-β-driven Smad3 signaling and inhibiting IL-6 and IL-23 receptor expression. The Journal of Immunology, 181: 2277-2284 (2008).
Xiao et al., *Adenomatous polyposis coli* (APC)-independent regulation of beta-catenin degradation via a retinoid X receptor-mediated pathway. Journal of Biological Chemistry, vol. 278, No. 32, pp. 29954-29962 (2003).
Yacila & Sari, Potential Therapeutic Drugs and Methods for the Treatment of Amyotrophic Lateral Sclerosis. Curr. Med. Chem., 21(31):3583-3593 (2014).
Yamada et al., Retinoid X receptor ligands: a patent review (2007-2013). Expert Opin. Ther. Patents, 24(4):443-452 (2014).
Zapata-Gonzalez et al., 9-cis-retinoic acid (9cRA), a retinoid X receptor (RXR) ligand, exerts immunosuppressive effects on dendritic cells by RXR-dependent activation: inhibition of peroxisome proliferator-activated receptor gamma blocks some of the 9cRA activities, and precludes them to mature phenotype development. The Journal of Immunogloy, 178:6130-6139 (2007).
Zhang et al., Thyroid hormone potentially benefits multiple sclerosis via facilitating remyelination. Mol. Neurobiol., 53, pp. 4406-4416 (2016).
Cristiano et al., Neutralization of IL-17 rescues amyloid-beta-induced neuroinflammation and memory impairment. British Pharmacological Society, 1-14 (2019).
Deloach et al., A retrospective review of the progress in amyotrophic lateral sclerosis drug discovery over the last decarde and a look at the latest strategies. Expert Opinion on Drug Discovery, 10:10, pp. 1099-1118 (2015).
Endong et al., The gap-junction inhibitor carbenoxolone suppresses the differentiation of Th17 cells through inhibition of IL-23 expression in antigen presenting cells. J. Neuroimmunol., 240-241:58-64 (2011).
Glicksman, Marcie A. The preclinical discovery of amyotrophic lateral sclerosis drugs. Expert Opinion on Drug Discovery, 6:11, pp. 1127-1138 (2011).
Gogoleva et al., Cytokines as mediators of neuroinflammation in experimental autoimmune encephalomyelitis. Biochemistry (Moscow), vol. 83, No. 9, pp. 1089-1103 (2018).
Itagaki et al., Presence of T-cytotoxic suppressor and leucocyte common antigen positive cells in Alzheimer's disease brain tissue. Neuroscience Letters, 91:259-264 (1988).
Katsuki et al., Retinoic acid receptor stimulation protects midbrain dopaminergic neurons from inflammatory degeneration via BDNF-mediated signaling. Journal of Neurochemistry, 110(2):707-718 (2009).
Koster et al., Emerging drugs for schizophrenia: an update. Expert Opinion on Emerging Drugs, 19:4, pp. 511-531 (2014).
Kuma-Kozaklewicz et al., New therapeutic targets for amyotrophic lateral scelrosis. Expert Opinion on Therapeutic Targets, 15:2, pp. 127-143 (2011).
Kumar et al., Inactivation of T cell receptor peptide-specific CD4 regulatory T cells induces chronic experimental autoimmune encephalomyelitis (EAE). J. Exp. Med., vol. 184, pp. 1609-1617 (1996).
Maas, Neuroprotective agents in traumatic brain injury. Expert Opinion Investigation Drugs, 10(4):753-767 (2001).
Mcgeer et al., Neuroimmune mechanisms in alzheimer disease pathogenesis. Alzheimer Disease and Associated Disorders, vol. 8, No. 3, pp. 149-158 (1994).

(56) References Cited

OTHER PUBLICATIONS

Mor et al., Autoimmune encephalomyelitis and uveitis induced by T cell immunity to self beta-synuclein. J. Immunol., 170:628-634 (2003).
Pirker et al., Upregulation of T-helper subtype 17 lymphocytes in cultured peripheral blood mononuclear cells of patients with Alzheimer's disease. Alzheimer's & Dementia, vol. 6, Iss. 4, Supplement, p. S262 (2010).
Pizza et al., Neuroinflamm-Aging and neurodegenerative diseases: An Overview. CNS & Neurological Disorders—Drug Targets, 10:621-634 (2011).
Popovic et al., Importance of immunological and inflammatory processes in the pathogenesis and therapy of Alzheimer's disease. Int. J. Neurosci., 95(3-4): 203-236 (1998).
Program and abstracts of Kinki Region Meeting of the Japanese Pharmacological Society, Jun. 2015, vol. 127, p. 51 (B-15).
Reisberg et al., Retrogenesis: clinical, physiologic, and pathologic mechanisms in brain aging, Alzheimer's and other dementing processes. Eur Arch Psychiatry Clin Neurosci, 249: Suppl. 3 III/28-III/36 (1999).
Ringheim et al., Neurodegenerative disease and the neuroimmune axis (Alzheimer's and Parkinson's disease, and viral infections. Journal of Neuroimmunology, 147:43-49 (2004).
Rogers et al., Expression of immune system-associated antigens by cells of the human central nervous system: relationship to the pathology of Alzheimer's disease. Neurobiology of Aging, vol. 9, pp. 339-349 (1988).
Roher et al., Increase AB peptides and reduced cholesterol and myelin proteins characterize white matter degeneration in Alzheimer's disease. Biochemistry, 41:11080-11090 (2002).
Rostami et al., Role of Th17 cells in the pathogenesis of CNS inflammatory demyelination. J. Neurol Sci., 333(0):76-87 (2013).
Sardi et al., Alzheimer's disease, autoimmunity and inflammation. The good, the bad and the ugly. Autoimmunity Reviews, 11:149-153 (2011).
Inoue et al., Rexinoids isolated from Sophora tonkinensis with a gene expression profile distinct from the synthetic rexinoid bexarotene. J. Nat. Prod. 77:1670-1677 (2014).
"Intranasal medication delivery—brief overview of the concept." Intranasal.net. Accessed Feb. 24, 2017.
Io Therapeutics, Inc. Brochure for the Symposium on IRX4204 at The 11th International Conference on Alzheimer's and Parkinson's Diseases (2013).
Jassem et al., A randomized phase III trial comparing bexarotene/cisplatin/vinorelbine versus cisplatin/vinorelbine in chemotherapy-naïve-patients with advanced or metastatic non-small cell lung cancer (NSCLC). Journal of Clinical Oncology, 2005 ASCO Annual Meeting Proceedings, vol. 23, No. 16S, Part I of II (Jun. 1 Supllement), Abstract 7024 (2005).
Johnson et al., Synthesis and biological activity of high-affinity retinoic acid receptor antagonists. Bioorganic & Medicinal Chemistry, vol. 7, No. 7, pp. 1321-1338 (1999).
Kagechika et al., Synthetic retinoids: recent developments concerning structure and clinical utility. Journal of Medicinal Chemistry, vol. 48, No. 19: 5875-5883, (2005).
Kawata et al., RXR partial agonist produced by side chain repositioning of alkoxy RXR full agonist retains antitype 2 diabetes activity without the adverse effects. J. Med. Chem. 58(2):912-926 (2015).
Kimura et al., IL-6: Regulator of Treg/Th17 balance. Eur. J. Immunol., 40:1830-1835 (2010).
Kim et al., Immunopathogenesis and therapy of cutaneous T cell lymphoma. Science in Medicine, The JCI Textbook of Molecular Medicine. Editors Marks et al., p. 164 (2007).
Klein et al., Cardiovascular involvement in general medial conditions. Thyroid disease and the heart. Circulation, 116:1725-1735 (2007).
Klein et al., Identification and functional separation of retinoic acid receptor neutral antagonists and inverse agonists. The Journal of Biological Chemistry, vol. 271, No. 37, pp. 22692-22696, 1996.

Knol et al., Absence of modulation of CD4+CD25high regulatory T cells in CTCL patients treated with bexarotene. Experimental Dermatology, 19:e95-e102 (2010).
Kotani et al., A naturally occurring rexinoid, honokiol, can serve as a regulator of various retinoid X receptor heterodimers. Biol. Pharm. Bull. 35(1):1-9 (2012).
Laclair et al., Treatment with bexarotene, a compound that increases apolipoprotein-E, provides no cognitive benefit in mutant APP/PS1 mice, Molecular Neurodegeneration 8:18 (10pp) (2013).
Lampen et al., Effects of receptor-selective retinoids on CYP26 gene expression and metabolism of all-trans-retinoic acid in intestinal cells. Drug Metabolism & Disposition, vol. 29, No. 3, pp. 742-747 (2001).
Lefebvre et al., Retinoid X receptors: common heterodimerization partners with distinct functions. Trends Endocrinol. Metab. 21:676-683 (2010).
Levasque et al., Nur77 and retinoid X receptors: crucial factors in dopamine-related neuroadaptation. Trends in Neuroscience, vol. 30, No. 1, pp. 22-30 (2007).
Li et al., Distinct Mechanisms of Glucose Lowering by Specific Agonists for Peroxisomal Proliferator Activated Receptor gamma and Retinoic Acid X Receptors, Journal of Biological Chemistry 280(46):38317-38327, 2005.
Liu et al., Combination Therapy of Insulin-Like Growth Factor Binding Protein-3 and Retinoid X Receptor Ligands Synergize on Prostate Cancer Cell Apoptosis In vitro and In vivo. Clin Cancer Res, 11(13):4851-4856 (2005).
Lowenthal et al., The Ethics of Early Evidence—Preparing for a Possible Breakthrough in Alzheimer's Disease, N Engl J Med., 367(6):488-490 (2012).
Macchia et al., RXR receptor agonist suppression of thryoid function: central effects in the absence of thyroid hormone receptor. Am. J. Physiol. Endocrinol. Metab., vol. 283, pp. E326-E331 (2002).
Mangelsdorf et al., Characterization of three RXR genes that mediate the action of 9-cis retinoic acid. Genes and Development 6:329-344 (1992).
Marketwire 2012: IRX4204 as a Potential Disease-Modifying Treatment for Alzheimer's Disease.
Marks et al., Science in Medicine: The JCI textbook of Molecular Medicine, p. 164 (2007).
Martin et al., Induction of the fatty acid transport protein 1 and acyl-CoA synthase genes by dimer-selective rexinoids suggests that the peroxisome proliferator-activated receptor-retinoid X receptor heterodimer is their molecular target. JBC 275(17):12612-12618 (2000).
Mcfarland et al., Low dose bexarotene treatment rescues dopamine neurons and restores behavioral function in models of Parkinson's disease. ACS Chem. Neurosci. 4:1430-1438 (2013).
Migliore, Intranasal Delivery of GDNF for the Treatment of Parkinson's Disease. Doctoral Thesis, Pharmaceutical Sciences, Northeastern University, Boston, MA (2008).
Miller et al., Initial clinical trial of a selective retinoid X receptor ligand, LGD1069. J Clin Oncol., 15(2):790-795 (1997).
Monahan et al., Neuroinflammation and peripheral immune infiltration in Parkinson's disease: an autoimmune hypothesis. Cell Transplant, 17:363-372 (2008).
Morris & Burns, Insulin: An Emerging Treatment for Alzheimer's Disease Dementia? Curr. Neurol. Neurosci. Rep. 12(5):520-527 (2012).
Munhoz et al., Parkinson's disease and thyroid dysfunction. Parkinsonism & Related Disorders, 10(6):381-383 (2004).
National Multiple Sclerosis Society, Medications, accessed May 12, 2017, pp. 1-5.
Natrajan et al., Retinoid X receptor activation reverses age-related deficiencies in myelin debris phagocytosis and remyelination. Brain A Journal of Neurology, 138:3581-3597 (2015).
Nishimaki-Mogami et al., The RXR agonists PA024 and HX630 have different abilities to activate LXR/RXR and to induce ABCA1 expression in macrophage cell lines. Biochemical Pharmacology, 76: 1006-1013 (2008).
Ohsawa et al., Modification of the lipophilic domain of RXR agonists differentially influences activation of RXR heterodimers. ACS Med Chem Lett., 1:521-525 (2010).

(56) References Cited

OTHER PUBLICATIONS

Olson et al., Immunomodulation as a neuroprotective and therapeutic strategy for Parkinson's disease. Curr Opin Pharmacol. 26:87-95 (2016).
Park et al., Salvage chemotherapy of gemcitabine, dexamethasone, and cisplatin (GDP) for patients with relapsed or refractory peripheral T-cell lymphomas: a consortium for improving survival of lymphoma (CISL) trial. Ann. Hematol., vol. 94, No. 11, pp. 1845-1851, see abstract (2015).
Perlmann et al., A novel pathway for vitamin A signaling mediated by RXR heterodimerization with NGFI-B and NURR1. Genes & Develop. 9:769-782 (1995).
Petty et al., Weekly paclitaxel (Taxol®), carboplatin (Paraplatin®), and bexarotene (Tagretin®) for the treatment of patients with advanced non-small cell lung cancer: Efficacy results from a Phase I/II study. Journal of Clinical ONcolocy, 2005 ASCO Annual Meeting Proceedings, vol. 23, No. 16S, Part I of II (Jun. 1 Supplement) Abstract 7243 (2005).
Pierrot et al., Targretin Improves Cognitive and Biological Markers in a Patient with Alzheimer's Disease. Journal of Alzheimer's Disease, 49:271-276 (2016).
Price et al., Comment on ApoE-directed Therapeutics Rapidly Clear beta-Amyloid and Reverse Deficits in AD Mouse Models. Science 340:924-d (2013).
Ramaswamy et al., Trophic factors therapy in Parkinson's disease. Prog. Brain Res., 175:201-216 (2009).
Ramlau et al., Randomized phase III trial comparing bexarotene (L1069-49)/cisplatin/vinorelbine with cisplatin/vinorelbine in chemotherapy-naïve patients with advanced or metastic non-small-cell lung cancer: Spirit I. J. Clin. Oncol., 26:1886-1892 (2008).
Reynolds et al., Regulatory T cells attenuate Th17 cell-mediated nigrostriatal dopaminergic neurodegneration in a model of Parkinson's disease. J. Immunol., vol. 184, pp. 2261-2271 (2010).
Riancho et al., Neuroprotective effect of bexarotene in SOD1G93A mouse model of amyotrophic lateral sclerosis. Frontiers in Cellular Neuroscience 9:Article 250 (2015).
Rigas et al., Emerging role of rexinoids in non-small cell lung cancer: Focus on bexarotene. The Oncologist, 10:22-33 (2005).
Rizvi et al., A phase I study of LGD1069 in adults with advanced cancer. Clin. Cancer Res., 5:1658-1664 (1999).
Sacchetti et al., Requirements for heterodimerization between orphan nuclear receptor Nurr1 and Retinoid X Receptors. The Journal of Biological Chemistry, 277(38):35088-35096 (2002).
Salama et al., Role of L-thyroxin in counteracting rotenone induced neurotoxocity in rats. Environmental Toxicology and Pharmacology, 35:270-277 (2013).
Sherman et al., Central hypothyroidism associated with retinoid X receptor-selective ligands. The New England Journal of Medicine, vol. 340, No. 14, pp. 1075-1079 (1999).
Alcala-Barraza et al., Intranasal delivery of neurotrophic factors BDNF, CNTF, EPO, and NT-4 to the CNS. Journal of Drug Targeting, 18(3):179-190 (2009).
Altucci L et al., RAR and RXR modulation in cancer and metabolic disease. Nature Review Drug Discovery, vol. 6: 793-810 (2007).
Alzforum 2013: Can Cancer Therapy Be Neurodegenerative Wonder Drug?
Annerbo et al., Review Article: A clinical review of the association of thyroid stimulating hormone and cognitive impairment. ISRN Endocrinology, vol. 2013, Article ID 856017, 6 pages (2013).
Balasubramanian et al., Suppression of human pancreatic cancer cell proliferation by AGN194204, an RXR-selective retinoid. Carcinogenesis, 2004, vol. 25, No. 8, pp. 1377-1385.
Balducci et al., The Continuing Failure of Bexarotene in Alzheimer's Disease Mice. J Alzheimers Dis., 46:471-482 (2015).
Benson et al., All-trans retinoic acid mediates enhanced T reg cell growth, differentiation, and gut homing in the face of high levels of co-stimulation. The Journal of Experimental Medicine, vol. 204, No. 8, pp. 1765-1774 (2007).
Beyer et al., Weight change and body composition in patients with Parkinson's disease. J. Am. DietAssoc., vol. 95, pp. 979-983 (1995).
Bilbao et al., Insulin-like growth factor-1 stimulates regulatory T cells and suppresses autoimmune disease. EMBO Mol. Med., 6(11):1423-1435 (2014).
Blumenschein et al., A randomized phase III trial comparing bexarotene/carboplatin/paclitaxel versus carboplatin/paclitaxel in chemotherapy-naive patients with advanced or metastatic non-small cell lung cancer (NSCLC). Journal of Clinical Oncology, 2005 ASCO Annual Meeting Proceedings, vol. 23, No. 16S, Part I of II, Abstract 7001 (2005).
Bordoni et al., Bexarotene improves TTP in untreated, advanced NSCLC, when given in combination with carboplalin/paclitaxel. Journal of Clinical Oncology, ASCO 2005 Annual Meeting, Abstract 7270.
Breen et al., Regulation of Thyroid-Stimulating Hormone beta-Subunit and Growth Hormone Messenger Ribonucleic Acid Levels in the Rat: Effect of Vitamin A Status, Endocrinology 136:543-9 (1995).
Cal et al., Doxazosin: a new cytotoxic agent for prostate cancer? BJU Int. 85:672-675 (2000).
Calza et al., Thyroid hormone activates oligodendrocyte precursors and increases a myelin-forming protein and NGF content in the spinal cord during experimental allergic encephalomyelitis. PNAS, vol. 99, No. 5, pp. 3258-3263 (2002).
Coya et al., Retinoic Acid Inhibits In Vivo Thyroid-Stimulating Hormone Secretion, Life Sciences, Pharmacology Letters, 60:247-50, 1997.
Cramer et al., ApoE-directed therapeutics rapidly clear β-amyloid and reverse deficits in AD mouse models. Science, 335(6075): 1503-1506 (2012).
Crowe et al.,A retinoid X receptor (RXR)-selective retinoid reveals that RXR-alpha is potentially a therapeutic target in breast cancer cell lines, and that it potentiates antiproliferative and apoptotic responses to peroxisome proliferator-activated receptor ligands. Breast Cancer Res., vol. 6, No. 5, pp. R546-R555 (2004).
Cummings et al., Double-blind, placebo-controlled, proof-of-concept trial of bexarotene Xin moderate Alzheimer's disease. Alzheimer's Research & Therapy, 8:4 (2016).
Debnath & Berk, Th17 Pathway—Mediated Immunopathogenesis of Schizophrenia: Mechanisms and Implications. Schizophrenia Bulletin, 40(6):1412-1421 (2014).
Dell'Acqua ML et al., Functional and molecular evidence of myelin- and neuroprotection by thyroid hormone administration in experimental allergic encephalomyelitis. Neuropath. Appl. Neurobiol., 38:454-470 (2012).
D'Intino G et al., Triiodothyronine administration ameliorates the demyelination/remyelination ratio in a non-human primate model of multiple sclerosis by corrected tissue hypothyroidism. J Neuroendocrin., 23:778-790 (2011).
Dore et al., Insulin-like growth factor I protects and rescues hippocampal neurons against beta-amyloid- and human amylin-induced toxicity. Proc. Natl. Acad. Sci. USA, 94:4772-4777 (1997).
Duvic et al., Phase 2 and 3 Clinical Trial of Oral Bexarotene (Targretin Capsules) for the Treatment of Refractory or Persistent Early-Stage Cutaneous T-Cell Lymphoma, Arch Dermatol. 137:581-593, 2001.
Estephan et al., Phase II trial of gemcitabine (G), carboplatin (C) and bexarotene (B) in patients (pts) with newly diagnosed, locally-advanced or metastatic non-small cell carcinoma of the lung. Journal of Clinical Oncology, 2005 ASCO Annual Meeting Proceedings, vol. 23, No. 16S, Part I of II (Jun. 1 Supplement, Abstract 7308 (2005).
Elias et al., Retinoic acid inhibits TH17 polarization and enhances FoxP3 expression through a Stat-3/Stat-5 independent signaling pathway. Blood, vol. 111, No. 3, pp. 1013-1020 (2008).
Fitz et al., Comment on ApoE-directed Therapeutics Rapidly Clear beta-Amyloid and Reverse Deficits in AD Mouse Models. Science 340:924-c (2013).
Franco et al., Thyroid hormones promote differentiation of oligodendrocyte progenitor cells and improve remyelination after cuprizone-induced demyelination. Experimental Neurology, 212, pp. 458-467, 2008 (2008).

(56) References Cited

OTHER PUBLICATIONS

Freiherr et al., Intranasal Insulin as a Treatment for Alzheimer's Disease: A Review of Basic Research and Clinical Evidence. CNS Drugs 27:505-514 (2013).
Friling et al., Activation of retinoid X receptor increases dopamine cell survival in models for Parkinson's disease. BMC Neuroscience, 10: 146 (2009).
Fu et al., Thyroid hormone prevents cognitive deficit in a mouse model of Alzheimer's disease. Neuropharmacology, 58:722-729 (2010).
Gibb et al., The substantia nigra and ventral tegmental area in Alzheimer's disease and Down's sydrome. J. Neurol. Neurosurg. and Psychiatry, 52:193-200 (1989).
Golub et al., Molecular classification of cancer: Class discovery and class prediction by gene expression monitoring. Science, vol. 286, Oct. 15, 1999, pp. 531-537.
Gonzalez et al., T-cell-mediated regulation of neuroinflammation involved in neurodegenerative diseases. J Neuroinflam 11:201-212 (2014).
Govindan et al., Phase II trial of bexarotene capsules in patients with non-small-cell lung cancer (NSCLC) who have failed at least 2 prior systemic therapies for Stage IIIB/IV disease. Journal of Clinical Oncology, 2005 ASCO Annual Meeting Proceedings, vol. 23, No. 16S, Part I of II, Abstract 7116 (2005).
Graber et al., Protective autoimmunity in the nervous system. Pharmacol. Therapeut., 121:147-159 (2009).
Haugen et al., The Thyrotrope-Restricted Isoform of the Retinoid-X Receptor-y1 Mediates 9-cis-Retinoic Acid Suppression of Thyrotropin-beta Promoter Activity. Molecular Endocrinology 11:481-9, 1997.
Henkel et al., Regulatory T-lymphocytes mediate amyotrophic lateral sclerosis progression and survival. EMBO Mol. Med., 5:64-79 (2012).
Hu et al., Imbalance between IL-17A-Producing Cells and Regulatory T Cells during Ischemic Stroke. Mediators of Inflammation 2014: Article ID 813045, 2014.
Huang et al., Retinoid X receptor gamma signaling accelerates CNS remyelination, Nature Neuroscience, 14(1):45-53, 2011 (Epub Dec. 5, 2010).
International Search Report and Written Opinion dated Mar. 28, 2013 for International Application Serial No. PCT/US2012/069566 filed on Dec. 13, 2012.
International Search Report and Written Opinion dated Jan. 5, 2017 for International Application Serial No. PCT/US2016/059770 filed Oct. 31, 2016.
International Search Report for PCT/US2007/011730 dated May 2, 2008.
International Search Report and Written Opinion dated Sep. 25, 2007 for International Application No. PCT/US2006/038252 filed on Oct. 2, 2006.
International Search Report and Written Opinion dated Dec. 29, 2016 for International Application No. PCT/US2016/059775 filed on Oct. 31, 2016.
International Search Report and Written Opinion dated Jan. 10, 2017 for International Application No. PCT/US2016/059776 filed on Oct. 31, 2016.
International Search Report and Written Opinion dated Dec. 29, 2016 for International Application No. PCT/US2016/059779 filed on Oct. 31, 2016.
International Search Report and Written Opinion dated May 22, 2017 for International Application No. PCT/US2016/059772 filed on Oct. 31, 2016.
International Search Report and Written Opinion dated Jan. 18, 2019 for International Application No. PCT/US2018/052031 filed on Sep. 20, 2018.
International Search Report and Written Opinion dated Dec. 11, 2018 for International Application No. PCT/US2018/048876 filed on Aug. 30, 2018.
International Application Serial No. PCT/US2018/052031 filed on Sep. 20, 2018.
U.S. Appl. No. 14/507,730, filed Oct. 6, 2014, Treatment of Diseases by Concurrently Eliciting Remyelination Effects and Immunomodulatory Effects Using Selective RXR Agonists.
U.S. Appl. No. 14/626,339 (U.S. Pat. No. 10,034,845), filed Feb. 19, 2015, Autoimmune Disorder Treatment Using RXR Agonists.
U.S. Appl. No. 14/732,328, filed Jun. 5, 2015, Autoimmune Disorder Treatment Using RXR Agonists.
U.S. Appl. No. 15/339,762 (U.S. Pat. No. 10,092,535), filed Oct. 31, 2016, Treatment of Nervous System Disorders Using Combinations of RXR Agonists and Thyroid Hormones.
U.S. Appl. No. 15/339,752 (U.S. Pat. No. 9,877,941), filed Oct. 31, 2016, Treatment of Nervous System Disorders Using Combinations of RXR Agonists and Thyroid Hormones.
U.S. Appl. No. 15/341,969 (U.S. Pat. No. 10,285,960), filed Nov. 2, 2016, Autoimmune Disorder Treatment Using RXR Agonists.
U.S. Appl. No. 15/812,821 (U.S. Pat. No. 10,278,932), filed Nov. 14, 2017, Treatment of Nervous System Disorders Using Combinations of RXR Agonists and Thyroid Hormones.
U.S. Appl. No. 15/852,580 (U.S. Pat. No. 10,201,512), filed Dec. 22, 2017, Autoimmune Disorder Treatment Using RXR Agonists.
U.S. Appl. No. 16/083,619, filed Sep. 10, 2018, Treatment of Muscular Disorders with Combinations of RXR Agonists and Thyroid Hormones.
U.S. Appl. No. 15/770,737, filed Apr. 24, 2018, Treatment of Nervous System Disorders Using Thyroid Hormone Neutral Doses of RXR Agonists.
U.S. Appl. No. 16/083,799, filed Sep. 10, 2018, Treatment of Autoimmune Diseases with Combinations of RXR Agonists and Thyroid Hormones.
U.S. Appl. No. 15/988,965, filed May 24, 2018, Autoimmune Disorder Treatment Using RXR Agonists.
U.S. Appl. No. 16/118,001, filed Aug. 30, 2018, Treatment of Nervous System Disorders Using Combinations of RXR Agonists and Thyroid Hormones.
U.S. Appl. No. 16/228,217, filed Dec. 20, 2018, Autoimmune Disorder Treatment Using RXR Agonists.
U.S. Appl. No. 16/355,354, filed Mar. 15, 2019, Treatment of Nervous System Disorders Using Combinations of RXR Agonists and Thyroid Hormones.
U.S. Appl. No. 16/358,021, filed Mar. 19, 2019, Treatment of Nervous System Disorders Using Combinations of RXR Agonists and Thyroid Hormones.
U.S. Appl. No. 16/364,653, filed Mar. 26, 2019, Treatment of Nervous System Disorders Using Combinations of RXR Agonists and Thyroid Hormones.
U.S. Appl. No. 16/296,012, filed Mar. 7, 2019, Treatment of Nervous System Disorders Using Combinations of RXR Agonists and Thyroid Hormones.
U.S. Appl. No. 16/379,074, filed Apr. 9, 2019, Treatment of Nervous System Disorders Using Combinations of RXR Agonists and Thyroid Hormones.
U.S. Appl. No. 16/386,058, filed Apr. 16, 2019, Treatment of Nervous System Disorders Using Combinations of RXR Agonists and Thyroid Hormones.
U.S. Appl. No. 16/391,665, filed Apr. 23, 2019, Treatment of Nervous System Disorders Using Combinations of RXR Agonists and Thyroid Hormones.
U.S. Appl. No. 16/373,414, filed Apr. 2, 2019, Treatment of Nervous System Disorders Using Combinations of RXR Agonists and Thyroid Hormones.
U.S. Appl. No. 16/742,331, filed Jan. 14, 2020, Treatment of Nervous System Disorders Using Combinations of RXR Agonists and Thyroid Hormones.
U.S. Appl. No. 16/742,375, filed Jan. 14, 2020, Treatment of Nervous System Disorders Using Combinations of RXR Agonists and Thyroid Hormones.
Li, et al., Altered expression of CD4+ CD25+ regulatory T cells and its 5-HT1a receptor in patients with major depressive disorder. Journal of Affective Disorders 124:68-75 (2010).
Chen, et al., Emerging tendency toward autoimmune process in major depressive patients: A novel insight from Th17 cells. Psychiatry Research 188:224-230 (2011).

(56) References Cited

OTHER PUBLICATIONS

Kim, et al., CD4+ CD25+ Regulatory T-cell Depletion Modulates Anxiety and Depression-like Behaviors in Mice. Kim, et al., PLoS One 7(7):e42054* (2012). pp. 1-11 as submitted.

Beurel, et al., Inflammatory Th17 cells promote depression-like behavior in mice. Biol Psychiatry 73(7):622-630* (2013). pp. 1-16 as submitted.

Aston, et al., Transcriptional profiling reveals evidence for signaling and oligodendroglial abnormalities in the temporal cortex from patients with major depressive disorder. Molecular Psychiatry 10:309-322 (2005).

Regenold, et al., Myelin staining of deep white matter in the dorsolateral prefrontal cortex in schizophrenia, bipolar disorder, and unipolar major depression. Regenold, et al., Psychiatry Research 151:179-188 (2007).

Edgar and Sabille, A putative functional role for oligodendrocytes in mood regulation. Transl Psychiatry 2:e109* (2012). pp. 1-9 as submitted.

Guo, et al., Altered white matter integrity in young adults with first-episode treatment-naïve, and treatment responsive depression. Neuroscience Letters 522:139-144 (2012).

Guo, et al., Altered white matter integrity of forebrain in treatment-resistant depression: A diffusion tensor imaging study with tract-based spatial statistics. Progress in Neuro-Psychopharmacology & Biological Psychiatry 38:201-206 (2012).

* cited by examiner

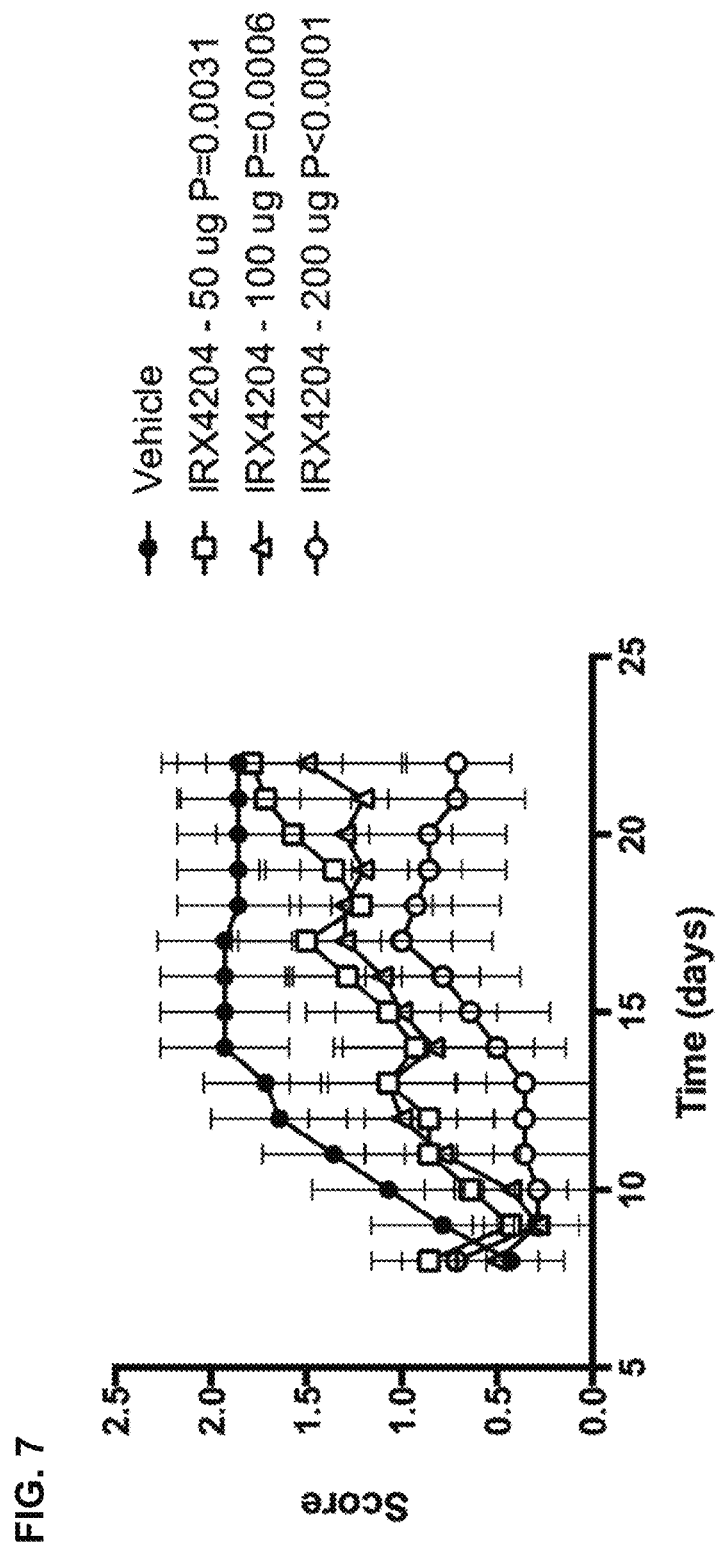

TREATMENT OF NERVOUS SYSTEM DISORDERS USING COMBINATIONS OF RXR AGONISTS AND THYROID HORMONES

RELATED APPLICATIONS

This application is a continuation of U.S. patent application Ser. No. 16/364,653, filed Mar. 26, 2019, which is a divisional of Ser. No. 16/118,001, filed Aug. 30, 2018, now U.S. Pat. No. 10,485,778, which is continuation of U.S. patent application Ser. No. 15/812,821, filed Nov. 14, 2017, now U.S. Pat. No. 10,278,932, which is a continuation of U.S. patent application Ser. No. 15/339,752 filed Oct. 31, 2016, now issued U.S. Pat. No. 9,877,941, which claims priority to U.S. Provisional Patent Application No. 62/249,216, filed on Oct. 31, 2015. The entire content of each of these applications is incorporated herein by reference.

FIELD

The present disclosure is directed to methods of treating nervous system disorders by inducing remyelination, neuroprotection, and immunomodulation using a Retinoid X Receptor (RXR) agonist in combination with a thyroid hormone.

BACKGROUND

The current standard of care treatment for nervous system diseases include several anti-inflammatory and immunomodulatory drugs that promote clinical benefit by modulating the patient's inflammatory/immune responses. While these therapies delay disease progression, they are unable to reverse the pathology or restore neurological function. One way to achieve significant advancement in the current standard of care for nervous system disorder patients is to promote remyelination or neuroprotection, or both, and thereby regenerate or maintain healthy axons and neurons.

SUMMARY

Disclosed herein are methods of treating nervous system disorders by inducing remyelination, neuroprotection, and immunomodulation using a Retinoid X Receptor (RXR) agonists in combination with a thyroid hormone Specifically, disclosed herein are methods for treating a nervous system disorder, the methods comprising administering to an individual in need thereof a therapeutically effective amount of a RXR agonist and a therapeutically effective amount of a thyroid hormone, wherein administration of the combination of the RXR agonist and the thyroid hormone treats the nervous system disorder in the individual more effectively than treatment with the RXR agonist or thyroid hormone alone. In some embodiments, the combination of RXR agonist and thyroxine treats the nervous system disorder in the individual by both promoting remyelination and neuroprotection of neurons and modulating the individual's immune system.

In some embodiments, the RXR agonist is a selective RXR agonist and is 3,7-dimethyl-6(S),7(S)-methano,7-[1,1,4,4-tetramethyl-1,2,3,4-tetrahydronaphth-7-yl]2(E),4(E) heptadienoic acid, and has the structure of formula III:

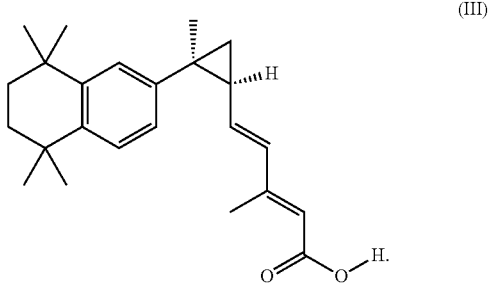

In other embodiments, the RXR agonist is bexarotene or LG268.

In certain embodiments, the nervous system disorder is a central nervous system (CNS) disorder. In certain embodiments, the nervous system disorder is relapsing/remitting, primary progressive, and secondary progressive forms of multiple sclerosis (MS), diffuse white matter injury in pre-term infants, neuromyelitis optica, acute disseminated encephalomyelitis, Marburg multiple sclerosis, diffuse myelinoclastic sclerosis (Schilder's disease), Balo concentric sclerosis, solitary sclerosis, optic neuritis, transverse myelitis, amyotrophic lateral sclerosis (ALS), leukodystrophy (multiple variants, e.g. adrenoleukodystrophy, adrenomyeloneuropathy), Parkinson's disease, Alzheimer's disease, progressive supranuclear palsy, stroke, CNS trauma including traumatic brain injury and traumatic spinal cord injury, radiation induced neuroinflammation, radiation somnolence syndrome, Devic's disease, inflammatory demyelinating diseases, CNS neuropathies, central pontine myelinolysis, Tabes dorsalis (syphilitic myelopathy), progressive multifocal leukoencephalopathy, leukodystrophy, depression, schizophrenia, epilepsy, migraine, and dementias In certain embodiments, the nervous system disorder is a demyelination-related disorder such as multiple sclerosis or radiation-induced nervous system inflammation.

In some embodiments, the demyelination-related disorder is a peripheral nervous system disorder such as Guillain-Barré Syndrome, acute inflammatory demyelinating polyneuropathy, chronic inflammatory demyelinating polyneuropathy, demyelinating diabetic neuropathy, progressive inflammatory neuropathy, drug- or toxin-induced neuropathy, such as chemotherapy-induced neuropathy or organophosphate-induced neuropathy, anti-MAG peripheral neuropathy, Charcot-Marie-Tooth Disease, or copper deficiency.

In some embodiments, the therapeutically effective amount of the RXR agonist is about 0.001 mg/day to about 100 mg/day. In other embodiments, the therapeutically effective amount of the RXR agonist is about 1 mg/day to about 20 mg/day. In some embodiments, the thyroid hormone is thyroxine. In certain embodiments, the therapeutically effective amount of thyroxine is about 12.5 µg/day to about 250 µg/day. In some embodiments, the RXR agonist is administered by nasal administration. In some embodiments, both the RXR agonist and thyroxine are administered by nasal administration. In some embodiments, the RXR agonist is administered orally. In some embodiments, the RXR agonist and the thyroxine are administered substantially simultaneously. In some embodiments, the RXR agonist and thyroxine are administered on different schedules. In some embodiments, the thyroid hormone is administered orally or subcutaneously.

In certain embodiments, treatment with the combination of RXR agonist and thyroxine reduces at least one symptom of a nervous system disorder, wherein the at least one symptom reduced is inflammation, fatigue, dizziness, headache, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, blurred or double vision, ataxia, clonus, dysarthria, fatigue, clumsiness, hand paralysis, hemiparesis, genital anesthesia, incoordination, paresthesias, ocular paralysis, impaired muscle coordination, weakness (muscle), loss of sensation, impaired vision, neurological symptoms, unsteady gait, spastic paraparesis, incontinence, hearing problems, or speech problems. In other embodiments, treatment with the combination of RXR agonist and thyroxine reduces at least two symptoms of the nervous system disorder. In other embodiments, treatment with the combination of RXR agonist and thyroxine reduces at least five symptoms of the nervous system disorder.

In some embodiments, the methods further comprise determining free serum thyroxine; and adjusting the dose of thyroxine to keep thyroxine levels in an euthyroid range.

In some embodiments, further comprises administration of a neurotrophic factor, or neurotrophic factor mimetic in combination with the RXR agonist and the thyroid hormone for treatment of a disease of the nervous system. In some embodiments, the neurotrophic factor is BDNF, GDNF, NGF, NT-3, bFGF, CNTF, NT-4/5, IGF, or insulin, or a mimetic thereof.

In certain embodiments, wherein the disease of the nervous system is Parkinson's disease, Alzheimer's disease, a multiple sclerosis, an optic neuritis, a stroke, a CNS trauma, amyotrophic lateral sclerosis, a neuropathy, a nervous system hypoxia, a CNS toxicity, a dementia, a retinopathy, Huntington's disease, a synucleinopathy, epilepsy, autism, schizophrenia, depression, or an aging-related CNS degeneration.

In some embodiments, the neurotrophic factor is GDNF, or a GDNF mimetic, and the nervous system disease is Parkinson's disease. In some embodiments, the neurotrophic factor is GDNF, or a GDNF mimetic, and the nervous system disease is amyotrophic lateral sclerosis. In some embodiments, the neurotrophic factor is BDNF and the nervous system disease is Alzheimer's disease. In some embodiments, the neurotrophic factor is insulin or insulin-like growth factor, and the nervous system disease is Alzheimer's disease. In some embodiments, the neurotrophic factor is BDNF and the nervous system disease is multiple sclerosis. In some embodiments, the neurotrophic factor is BDNF, and the nervous system disease is stroke, nervous system trauma, aging, or dementia. In some embodiments, the neurotrophic factor is BDNF, GDNF, or insulin, and the nervous system disease is aging-related nervous system neurodegeneration. In certain embodiments, the neurotrophic factor or mimetic is administered by oral, parenteral, nasal, or topical routes, or by controlled release.

Also disclosed herein is the use of a combination of a RXR agonist, a thyroid hormone, and a neurotrophic factor, or neurotrophic factor mimetic, for in vitro promotion of survival or growth of neurons or glial cells, for subsequent implantation into the nervous system of a patient with a nervous system disorder.

Also disclosed herein are methods for promoting survival or repair of neurons or glial cells in a patient with a nervous system disorder, the method comprising administering to an individual in need thereof a therapeutically effective amount of a RXR agonist disclosed herein and a therapeutically effective amount of a thyroid hormone, wherein administration of the combination of the RXR agonist and the thyroid hormone treats the nervous system disorder in the individual.

In certain embodiments, the method for promoting survival or repair of neurons or glial cells further comprises administration of a neurotrophic factor, or neurotrophic factor mimetic to promote survival or repair of neurons or glial cells in a patient with a nervous system disorder. In some embodiments, the neurotrophic factor is BDNF, GDNF, NGF, NT-3, bFGF, CNTF, NT-4/5, IGF, or insulin, or a mimetic thereof.

In some embodiments, the neurotrophic factor is GDNF, or a GDNF mimetic, and the nervous system disease is Parkinson's disease. In some embodiments, the neurotrophic factor is GDNF, or a GDNF mimetic, and the nervous system disease is amyotrophic lateral sclerosis. In some embodiments, the neurotrophic factor is BDNF and the nervous system disease is Alzheimer's disease. In some embodiments, the neurotrophic factor is insulin or insulin-like growth factor, and the nervous system disease is Alzheimer's disease. In some embodiments, the neurotrophic factor is BDNF and the nervous system disease is multiple sclerosis. In some embodiments, the neurotrophic factor is BDNF, and the nervous system disease is stroke, nervous system trauma, aging, or dementia. In some embodiments, the neurotrophic factor is BDNF, GDNF, or insulin, and the nervous system disease is aging-related nervous system neurodegeneration. In certain embodiments, the neurotrophic factor or mimetic is administered by oral, parenteral, nasal, or topical routes, or by controlled release.

Also disclosed herein are methods for treating multiple sclerosis, the method comprising administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid (compound of Formula III) and a therapeutically effective amount of thyroxine; and wherein administration of the combination treats the multiple sclerosis in the individual more effectively than treatment with 3,7-dimethyl-6(S),7(S)-methano,7-[1,1,4,4-tetramethyl-1,2,3,4-tetrahydronaphth-7-yl]2(E),4(E) heptadienoic acid or thyroid hormone alone.

Also disclosed herein are methods for treating a nervous system disorder, the method comprising administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid and a therapeutically acceptable amount of thyroxine; and wherein administration of the combination treats the nervous system disorder in the individual more effectively than treatment with 3,7-dimethyl-6(S),7(S)-methano,7-[1,1,4,4-tetramethyl-1,2,3,4-tetrahydronaphth-7-yl]2(E),4(E) heptadienoic acid or thyroid hormone alone, and wherein the RXR agonist is delivered directly to the nervous system of the individual by intrathecal administration, epidural administration, cranial injection or implant, or nasal administration.

Also disclosed are methods for treating Parkinson's disease, the method comprising administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid and a therapeutically effective amount of thyroxine; and wherein administration of the combination treats the Parkinson's disease in the individual more effectively than treatment with 3,7-dimethyl-6(S),7(S)-methano,7-[1,1,4,4-tetramethyl-1,2,3,4-tetrahydronaphth-7-yl]2(E),4(E) heptadienoic acid or thyroid hormone alone.

Also disclosed herein are methods for treating Alzheimer's disease, the method comprising administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid and a therapeutically effective amount of thyroxine; and wherein administration of the combination treats the Alzheimer's disease in the individual more effectively than treatment with 3,7-dimethyl-6(S),7(S)-methano,7-[1,1,4,4-tetramethyl-1,2,3,4-tetrahydronaphth-7-yl]2(E),4(E) heptadienoic acid or thyroid hormone alone.

BRIEF DESCRIPTION OF THE DRAWINGS

FIG. 3A depicts the number of $CD4^+$ cells and FIG. 3B depicts the number of $CD11c^+CD11b^+$ cells (myeloid DC) in mice treated with the selective RXR agonist IRX4204 (4204) versus the vehicle control.

FIG. 7 depicts effects of selective RXR agonist IRX4204 on EAE in mice,

FIG. 15B: 1 nM IRX4204; FIG. 15C: 0.1 nM IRX4204). * P<0.0001;  P<0.01.

FIG. 16A depicts remyelination in the hippocampus and FIG. 16B depicts remyelination in the cortex.

FIG. 20A depicts the myelinated axons per CC unit; FIG. 20B depicts the density of myelinated axons (per 10,000 $\mu m^2$); and FIG. 20C depicts the density of SM132+ ovoids (per 250,000 $\mu m^2$).

DETAILED DESCRIPTION

Figure 1:
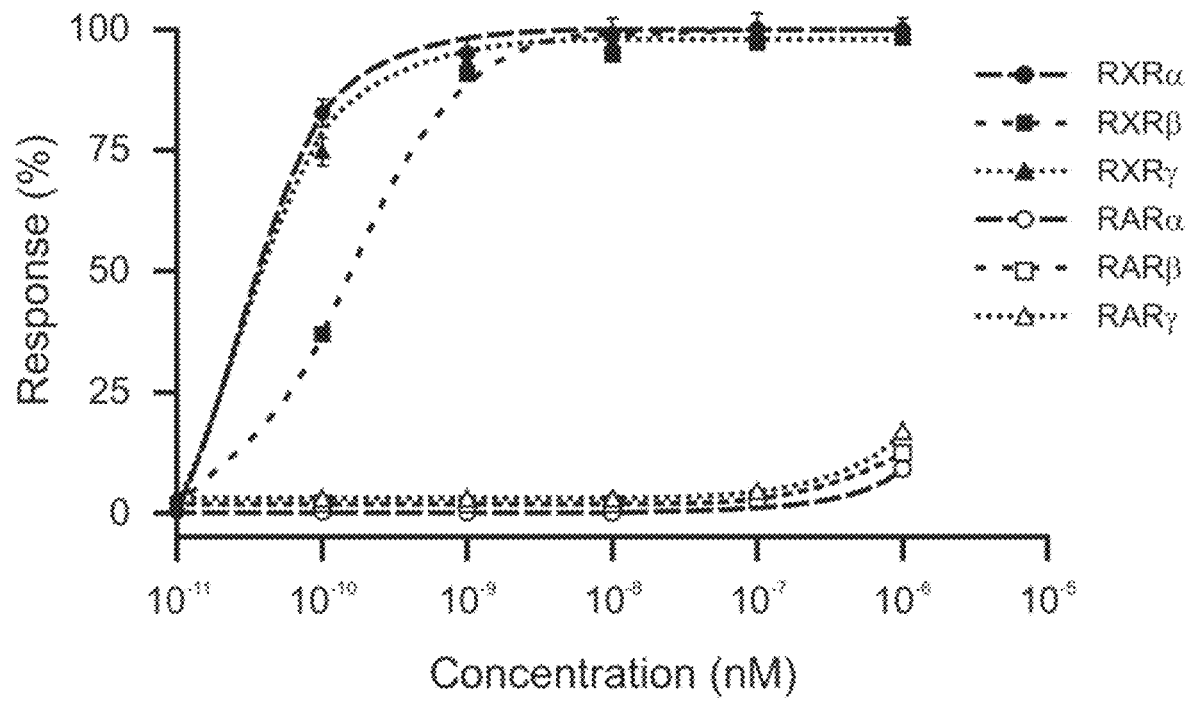
FIG. 1 shows RXR agonist activation of transcription from RXRα, RXRβ, RXRγ, RARα, RARβ, and RARγ using transactivation assays.

Many diseases of the nervous system are associated with demyelination of axons and neurons. Such disorders of demyelination may be autoimmune diseases or disorders of other etiologies. Multiple sclerosis (MS) is an example of an autoimmune disorder which is also associated with demyelination. Accordingly, an optimal drug or combination of drugs for the treatment of MS would address the autoimmune aspects of the disease while concurrently enhancing remyelination and providing neuroprotection by preventing demyelination. MS is currently treated by several immunomodulatory drugs that provide clinical benefit by modulating patient immune responses and producing anti-inflammatory effects. These drugs delay disease progression but do not reverse disease pathology or restore neurological function by restoring myelination of damaged neurons. IRX4204 (194204, Formula III), a retinoid X receptor (RXR) ligand that has an unique mechanism of action in being a selective activator of RXR homodimers and RXR-Nurr1 heterodimers, when combined with a thyroid hormone simultaneously provides immunomodulatory activities and also promotes remyelination and neuroprotection. IRX4204 promotes the differentiation of suppressive Treg cells while simultaneously inhibiting the differentiation of pro-inflammatory Th17 cells thereby favorably affecting the aberrantly skewed Th17/Treg cell ratio which underlies human autoimmune diseases such as MS (see co-pending US 2015/0038585, which is incorporated by reference for all it discloses regarding RXR agonists). Thus, by virtue of its effects on Th17/Treg cell ratios, IRX4204 will have clinical benefits similar to current standard of care treatments in MS. In addition, IRX4204 promotes remyelination of demyelinated neurons and neuroprotection by preventing demyelination. IRX4204 in combination with a thyroid hormone can additionally promote further remyelination of demyelinated neurons and afford greater neuroprotection by preventing demyelination more effectively. Accordingly, a thyroid hormone and IRX4204, and other RXR ligands of the same receptor activating profile, combination of compounds that provide both immunomodulatory activity and promote remyelination and neuroprotection (and regeneration), will not only delay disease progression in MS but also effect neural maintenance and repair by protecting and regenerating healthy axons and neurons. IRX4204 together with thyroid hormone is expected to be an optimal drug combination for the treatment of MS and other autoimmune diseases which are also associated with demyelination.

The Retinoic Acid Receptors (RARs) and RXRs and their cognate ligands function by distinct mechanisms. The RARs always form heterodimers with RXRs and these RAR/RXR heterodimers bind to specific response elements in the promoter regions of target genes. The binding of RAR agonists to the RAR receptor of the heterodimer results in activation of transcription of target genes leading to retinoid effects. On the other hand, RXR agonists do not activate RAR/RXR heterodimers. RXR heterodimer complexes like RAR/RXR can be referred to as non-permissive RXR heterodimers as activation of transcription due to ligand-binding occurs only at the non-RXR protein (e.g., RAR); activation of transcription due to ligand binding does not occur at the RXR. RXRs also interact with nuclear receptors other than RARs and RXR agonists may elicit some of its biological effects by binding to such RXR/receptor complexes. These RXR/receptor complexes can be referred to as permissive RXR heterodimers as activation of transcription due to ligand-binding could occur at the RXR, the other receptor, or both receptors. Examples of permissive RXR heterodimers include, without limitation, peroxisome proliferator activated receptor/RXR (PPAR/RXR), farnesyl X receptor/RXR (FXR/RXR), nuclear receptor related-1 protein (Nurr1/RXR) and liver X receptor/RXR (LXR/RXR). Alternately, RXRs may form RXR/RXR homodimers which can be activated by RXR agonists leading to rexinoid effects. Also, RXRs interact with proteins other than nuclear receptors and ligand binding to an RXR within such protein complexes can also lead to rexinoid effects. Due to these differences in mechanisms of action, RXR agonists and RAR agonists elicit distinct biological outcomes and even in the instances where they mediate similar biological effects, they do so by different mechanisms. Moreover, the unwanted side effects of retinoids, such as pro-inflammatory responses or mucocutaneous toxicity, are mediated by activation of one or more of the RAR receptor subtypes. Stated another way, biological effects mediated via RXR pathways would not induce pro-inflammatory responses, and thus, would not result in unwanted side effects.

Thus, aspects of the present specification provide, in part, a RXR agonist. As used herein, the term RXR agonist" refers to a compound that binds to one or more RXR receptors like an RXRα, a RXRβ, or a RXRγ in a manner that elicits gene transcription via an RXR response element. As use the term "selective RXR agonist" refers to the discriminatory activation of heterodimeric partners for RXR (such as a PPAR or a LXR) upon binding of a RXR agonist to one type of RXR heterodimer but not to another.

In one embodiment, the selective RXR agonist does not activate to any appreciable degree the permissive heterodimers PPAR/RXR, FXR/RXR, and LXR/RXR. In another embodiment, the RXR agonist activates the permissive heterodimer Nurr1/RXR, but not other permissive RXR heterodimers. One example of such a selective RXR agonist is 3,7-dimethyl-6(S),7(S)-methano,7-[1,1,4,4-tetramethyl-1,2,3,4-tetrahydronaphth-7-yl]2(E),4(E) heptadienoic acid (IRX4204, 194204) disclosed herein, the structure of which is shown in Formula III. In other aspects of this embodiment, the RXR agonist activates the permissive heterodimers PPAR/RXR, FXR/RXR, or LXR/RXR by 1% or less, 2% or less, 3% or less, 4% or less, 5% or less, 6% or less, 7% or less, 8% or less, 9% or less, or 10% or less relative to the ability of an activating RXR agonist to activate the same permissive heterodimer. Examples of an RXR agonist which activates one or more of PPAR/RXR, FXR/RXR, or LXR/RXR include, e.g., LGD1069 (bexarotene) and LGD268.

IRX4204, like some other RXR ligands, does not activate non-permissive heterodimers such as RAR/RXR. However, IRX4204 is unique in that it specifically activates the Nurr1/RXR heterodimer and does not activate other permissive RXR heterodimers such as PPAR/RXR, FXR/RXR, and LXR/RXR. Other RXR ligands generally activate these permissive RXR heterodimers. Thus, all RXR ligands cannot be classified as belonging to one class. IRX4204 belongs to a unique class of RXR ligands which specifically and selectively activate RXR homodimers and only one of the permissive RXR heterodimers, namely the Nurr1/RXR heterodimer. This unique receptor profile enables IRX4204 to have both immunomodulatory and neural repair properties.

RXR agonists are known to suppress thyroid function. Treatment of human subjects with the specific RXR agonist IRX4204 results first in a reduction in plasma levels of TSH followed by a reduction in circulating thyroxine levels. If a patient on IRX4204 develops adverse clinical symptoms due to the functional hypothyroidism, such clinical symptoms can be resolved by treatment of the patient with pharmacological doses of thyroxine. However supplementation of RXR agonist therapy with thyroid hormones has not been utilized therapeutically. Surprisingly, the combination of a RXR agonist and a thyroid hormone produces unexpectedly better efficacy than the use of a RXR agonist alone, demonstrating synergism between the RXR agonist and thyroid hormone in treatment of the nervous system disorder independent of regulation of plasma thyroid hormone levels.

Thus, the use of selective RXR homodimer, Nurr1/RXR activators, such as IRX4204, together with thyroid hormone provides uniquely effective ways of treating nervous system disorders.

Binding specificity is the ability of a RXR agonist to discriminate between a RXR receptor and a receptor that does not contain its binding site, such as, e.g., a RAR receptor. Certain RXR agonists can activate RXR homodimers as well as most permissive RXR heterodimers (for example, RXR/PPAR, RXR/LXR, RXR/Nurr1); such RXR agonists are known as non-selective RXR agonists. Certain other RXR agonists activate RXR homodimers and, unexpectedly, activate only one or a few RXR heterodimers. Such RXR agonists (e.g., IRX4204) are known as selective RXR agonists.

Thus, disclosed herein are selective RXR agonists having the structure of formula I:

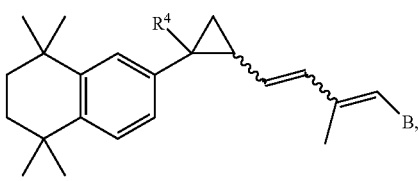

(I)

where $R^4$ is lower alkyl of 1 to 6 carbons; B is —COOH or —COOR$^8$ where $R^8$ is lower alkyl of 1 to 6 carbons, and the configuration about the cyclopropane ring is cis, and the configuration about the double bonds in the pentadienoic acid or ester chain attached to the cyclopropane ring is trans in each of the double bonds, or a pharmaceutically acceptable salt of the compound.

In an exemplary embodiment, a selective RXR agonist is a compound having the structure of formula II:

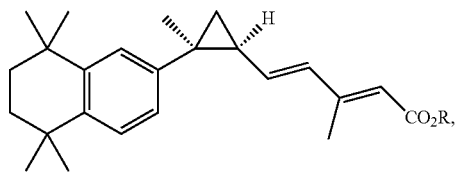

(II)

wherein R is H or lower alkyl of 1 to 6 carbons.

In a further exemplary embodiment, a selective RXR agonist is 3,7-dimethyl-6(S),7(S)-methano,7-[1,1,4,4-tetramethyl-1,2,3,4-tetrahydronaphth-7-yl]2(E),4(E) heptadienoic acid (IRX4204), and has the structure of formula III:

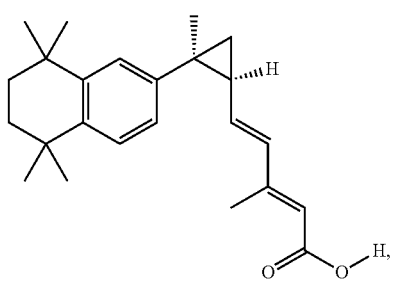

(III)

In certain embodiments, the ester form of 3,7-dimethyl-6(S),7(S)-methano,7-[1,1,4,4-tetramethyl-1,2,3,4-tetrahydronaphth-7-yl]2(E),4(E) heptadienoic acid is not within the scope of the present disclosure.

In certain embodiments, a non-selective RXR agonist is bexarotene (TARGRETIN®, 4-[1-(3,5,5,8,8-pentamethyl-6,7-dihydronaphthalen-2-yl)ethenyl]benzoic acid).

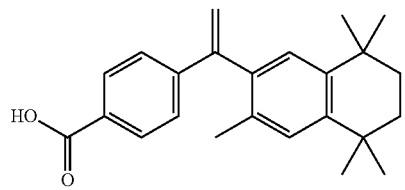

Bexarotene

In other embodiments, a RXR agonist is LG268 (LG100268, 2-[1-(3,5,5,8,8-pentamethyl-5,6,7,8-tetrahydro-2-naphthyl)cyclopropyl]pyridine-5-carboxylic acid).

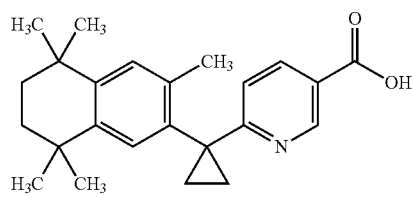

LG268

As used herein, the term "thyroid hormone" refers to thyroxine and triiodothyronine. Thyroxine (thyroid hormone $T_4$, levothyroxine sodium) is a tyrosine-based hormone produced by the thyroid gland and is primarily responsible for regulation of metabolism. Thyroxine is a prohormone for triiodothyronine ($T_3$). RXR agonists are known to suppress thyroid function. The clinical symptoms associated with this hypothyroidism can be treated with thyroid hormone. However supplementation of RXR agonist therapy with thyroid hormones to increase efficacy of the RXR agonist has not been utilized therapeutically.

As disclosed herein, the combination of a RXR agonist and a thyroid hormone increases myelination in the central or peripheral nervous system or provides neuroprotection by preventing demyelination by at least about 10% to at least about 25%, at least about 10% to at least about 50%, at least about 10% to at least about 75%, at least about 10% to at least about 100%, at least about 10% to at least about 200%, at least about 10% to at least about 300%, at least about 10% to at least about 400%, at least about 10% to at least about 500%, at least about 25% to at least about 50%, at least about 25% to at least about 75%, at least about 25% to at least about 100%, at least about 25% to at least about 200%, at least about 25% to at least about 300%, at least about 25% to at least about 400%, at least about 25% to at least about 500%, at least about 50% to at least about 100%, at least about 50% to at least about 200%, at least about 50% to at least about 300%, at least about 50% to at least about 400%, or at least about 50% to at least about 500%, relative to myelination levels in the absence of treatment with the RXR agonist and thyroid hormone.

In yet other aspects of this embodiment, the combination of a RXR agonist and a thyroid hormone increases differentiation of oligodendrocyte progenitor cells into functional oligodendrocytes in the central or peripheral nervous system by at least about 10% to at least about 25%, at least about 10% to at least about 50%, at least about 10% to at least about 75%, at least about 10% to at least about 100%, at least about 10% to at least about 200%, at least about 10% to at least about 300%, at least about 10% to at least about 400%, at least about 10% to at least about 500%, at least about 25% to at least about 50%, at least about 25% to at least about 75%, at least about 25% to at least about 100%, at least about 25% to at least about 200%, at least about 25% to at least about 300%, at least about 25% to at least about 400%, at least about 25% to at least about 500%, at least about 50% to at least about 100%, at least about 50% to at least about 200%, at least about 50% to at least about 300%, at least about 50% to at least about 400%, or at least about 50% to at least about 500%, relative to differentiation levels in the absence of treatment with the RXR agonist and thyroid hormone.

In yet another aspect of the present specification, the combination of a RXR agonist and a thyroid hormone increases the rate of myelin repair by at least about 10% to at least about 25%, at least about 10% to at least about 50%, at least about 10% to at least about 75%, at least about 10% to at least about 100%, at least about 10% to at least about 200%, at least about 10% to at least about 300%, at least about 10% to at least about 400%, at least about 10% to at least about 500%, at least about 25% to at least about 50%, at least about 25% to at least about 75%, at least about 25% to at least about 100%, at least about 25% to at least about 200%, at least about 25% to at least about 300%, at least about 25% to at least about 400%, at least about 25% to at least about 500%, at least about 50% to at least about 100%, at least about 50% to at least about 200%, at least about 50% to at least about 300%, at least about 50% to at least about 400%, or at least about 50% to at least about 500%, relative to myelin repair rates in the absence of treatment with the RXR agonist and thyroid hormone.

Aspects of the present specification provide, in part, a composition comprising a RXR agonist and a thyroid hormone. Exemplary RXR agonists are IRX4204, bexarotene, and LG268. Also provided are methods of treating nervous system disorders with a combination of IRX4204 and thyroxine.

Aspects of the present disclosure provide, in part, treatment of a nervous system disorder, such as a demyelination-related disorder. A demyelination-related disorder is any disease or disorder of the nervous system in which the myelin sheath of neurons is damaged. This damage impairs the conduction of signals in the affected nerves. In turn, the reduction in conduction ability causes deficiency in sensation, movement, cognition, or other functions depending on which nerves are involved. Both the central nervous system and the peripheral nervous system can be involved.

Some demyelination-related disorders are caused by genetics, some by infectious agents or toxins, some by autoimmune reactions, some by radiation injury, and some by unknown factors. Neuroleptics can also cause demyelination. The precise mechanism of demyelination is not clearly understood but there is substantial evidence that the body's own immune system is at least partially responsible, causing demyelination-related disorders to be considered autoimmune disorders.

Autoimmune disorders, including some nervous system and demyelination disorders, arise from an overactive immune response of the body against substances and tissues normally present in the body resulting in a break in tolerance toward self-antigens. In other words, the body actually attacks its own cells because the immune system mistakes some part of the body as a pathogen and attacks it. Characterized by the development of pathogenic T cell populations infiltrating the target organ or tissue, autoimmune disorders may be restricted to certain organs or involve a particular tissue in different places.

Nervous system disorders can be broadly divided into central and peripheral nervous system disorders, depending on the organs most affected. Central nervous system disorders include, without limitation, relapsing/remitting, primary progressive, and secondary progressive forms of multiple sclerosis (MS), diffuse white matter injury in pre-term infants, neuromyelitis optica, acute disseminated encephalomyelitis, Marburg multiple sclerosis, diffuse myelinoclastic sclerosis (Schilder's disease), Balo concentric sclerosis, solitary sclerosis, optic neuritis, transverse myelitis, amyotrophic lateral sclerosis (ALS), leukodystrophy (multiple variants, e.g. adrenoleukodystrophy, adrenomyeloneuropathy), Parkinson's disease, Alzheimer's disease, progressive supranuclear palsy, stroke, traumatic CNS injury including brain and spinal cord trauma, radiation induced neuroinflammation, radiation somnolence syndrome, Devic's disease, inflammatory demyelinating diseases, CNS neuropathies like those produced by vitamin B12 deficiency, central pontine myelinolysis, myelopathies like Tabes dorsalis (syphilitic myelopathy), leukoencephalopathies like progressive multifocal leukoencephalopathy, radiation induced central nervous system inflammation and leukodystrophies. Peripheral nervous system disorders include, without limitation, Guillain-Barre Syndrome, acute inflammatory demyelinating polyneuropathy, chronic inflammatory demyelinating polyneuropathy, demyelinating diabetic neuropathy, progressive inflammatory neuropathy, drug- or toxin-induced neuropathy, such as chemotherapy-induced neuropathy or radiation-induced neuropathy or organophosphate-induced neuropathy, anti-MAG peripheral neuropathy, Charcot-Marie-Tooth Disease, radiation induced neuropathy, copper deficiency, depression, schizophrenia, epilepsy, migraine, and dementias.

In some embodiments, the disorder is not cachexia.

In certain embodiments, the nervous system disorder is Alzheimer's disease. In other embodiments, the disorder is not Alzheimer's disease.

In one embodiment, the demyelination-related disorder is MS. Multiple sclerosis is currently treated by several immunomodulatory drugs that provide clinical benefit by modulating patient immune responses and producing anti-inflammatory effects. These drugs delay disease progression but do not prevent disease progression by preventing demyelination and affording neuroprotection or reverse disease pathology or restore neurological function by restoring myelination of damaged neurons. The selective RXR agonist IRX4204 has a unique mechanism of action in that it is a specific activator of RXR homodimers and RXR/Nurr1 heterodimers and simultaneously provides immunomodulatory activities and promotes remyelination and prevents demyelination particularly when used in combination with thyroid hormone. IRX4204 promotes the differentiation of suppressive Treg cells while simultaneously inhibiting the differentiation of pro-inflammatory Th17 cells, thereby favorably affecting the aberrantly skewed Th17/Treg cell ratio which underlies human autoimmune diseases such as MS. Thus, by virtue of its effects on Th17/Treg cell ratios, the combination of IRX4204 and a thyroid hormone is expected to have clinical benefits similar to, or better than, current standard of care treatments in MS. Moreover, IRX4204 in combination with thyroid hormone is more effective in promoting remyelination of demyelinated neurons and affording neuroprotection by preventing demyelination. Accordingly, the combination of IRX4204 and a thyroid hormone will not only delay disease progression in MS but also effect neural repair by regenerating healthy axons and neurons.

Aspects of the present disclosure includes, in part, reducing at least one symptom associated with a nervous system disorder. The actual symptoms associated with a nervous system disorder disclosed herein are well known and can be determined by a person of ordinary skill in the art by taking into account factors, including, without limitation, the location of the nervous system disorder, the cause of the nervous system disorder, the severity of the nervous system disorder, the tissue or organ affected by the nervous system, and the nervous system associated with inflammation. Non-limiting examples of symptoms reduced by a method of treating a nervous system disorder disclosed herein include inflammation, fatigue, dizziness, headache, malaise, elevated fever and high body temperature, extreme sensitivity to cold in the hands and feet, weakness and stiffness in muscles and joints, weight changes, digestive or gastrointestinal problems, low or high blood pressure, irritability, anxiety, depression, blurred or double vision, ataxia, clonus, dysarthria, clumsiness, hand paralysis, hemiparesis, genital anaesthesia, incoordination, paresthesias, ocular paralysis, impaired muscle coordination, weakness (muscle), loss of sensation, impaired vision, neurological symptoms, unsteady gait, spastic paraparesis, incontinence, hearing problems, and speech problems. In certain embodiments, treatment with a combination of an RXR agonist and a thyroid hormone reduces at least one symptom, at least two symptoms, at least three symptoms, at least four symptoms, or at least five symptoms of a nervous system disorder.

In certain embodiments, the RXR agonist treats MS and reduces one or more symptoms of MS such as, but not limited to, pain in the back or eyes, tremors, muscle cramping, difficulty walking, inability to rapidly change motions, involuntary movements, muscle paralysis, muscle rigidity, muscle weakness, problems with coordination, stiff muscles, clumsiness, muscle spasms, overactive reflexes, fatigue, dizziness, heat intolerance, poor balance, vertigo, weakness, excessive urination at night, leaking of urine, persistent urge to urinate, urinary retention, pins and needles, abnormality of taste, uncomfortable tingling and burning, blurred vision, double vision, vision loss, erectile dysfunction, sexual dysfunction, anxiety, mood swings, slurred speech, impaired voice, acute episodes, constipation, depression, difficulty swallowing, difficulty thinking and understanding, headache, heavy legs, numbness, numbness of face, rapid involuntary eye movement, sleep deprivation, tongue numbness, or difficulty raising the foot.

Efficacy of a compound or combination disclosed herein in MS can be determined by improvement in one or more recognized scales of MS including, but not limited to, the Expanded Disability Status Scale (EDSS; Kurtzke scale), Functional System Score (FSS), MS Progression: Disease Steps (DS), and MS Progression: Multiple Sclerosis Functional Composite (MSFC).

In certain embodiments, the RXR agonist treats Parkinson's disease and reduces one or more symptoms of Parkinson's disease such as, but not limited to, tremor (can occur at rest, in the hands, limbs, or can be postural), stiff muscles, difficulty standing, difficulty walking, difficulty with bodily movements, involuntary movements, muscle rigidity, problems with coordination, rhythmic muscle contractions, slow bodily movement, slow shuffling gait, daytime sleepiness, early awakening, nightmares, restless sleep, fatigue, dizziness, poor balance, restlessness, amnesia, confusion in the evening hours, dementia, difficulty thinking and understanding, impaired voice, soft speech, voice box spasms, anxiety, apathy, distorted sense of smell, loss of smell, dribbling of urine, leaking of urine, jaw stiffness, reduced facial expression, blank stare, constipation, depression, difficulty swallowing, drooling, falling, fear of falling, loss in contrast sensitivity, neck tightness, small handwriting, trembling, or unintentional writhing.

Efficacy of a compound or combination disclosed herein in Parkinson's disease can be determined by improvement in one or more recognized scales of Parkinson's disease including, but not limited to, Multiple Sclerosis Functional Composite (MSFC), Unified Parkinson's Disease Rating Scale (UPDRS), the Hoehn and Yahr scale, and the Schwab and England Activities of Daily Living Scale.

In certain embodiments, the RXR agonist treats Alzheimer's disease and reduces one or more symptoms of Alzheimer's disease such as, but not limited to, mental decline, difficulty thinking and understanding, confusion in the evening hours, delusion, disorientation, forgetfulness, making things up, mental confusion, difficulty concentrating, inability to create new memories, inability to do simple math, inability to recognize common things, aggression, agitation, difficulty with self care, irritability, meaningless repetition of own words, personality changes, lack of restraint, wandering and getting lost, anger, apathy, general discontent, loneliness, mood swings, depression, hallucination, paranoia, loss of appetite, restlessness, inability to combine muscle movements, jumbled speech.

Efficacy of a compound or combination disclosed herein in Alzheimer's disease can be determined by improvement in one or more recognized scales of Alzheimer's disease including, but not limited to, the Dementia Severity Rating Scale (DSRS), Mini-Mental State Examination (MMSE), Alzheimer's Disease Assessment Scale (ADAS), including the ADAS-cog, Neuropsychological Test Battery (NTB), Severe Impairment Battery (SIB), an Activities of Daily Living Scale, a Clinical Global Impression (CGI) scale, BEHAVE-AD, Brief Psychiatric Rating Scale (BPRS), Alzheimer Disease Related Quality of Life (ADRQL), Dementia Quality of Life Instrument (DQoL), the Quality of Life-Alzheimer's Disease (QoL-AD), and the Quality of Life in Late-Stage Dementia Scale (QUALID). Also within the scope of this disclosure is the treatment of other disorders with a combination of an RXR agonist and a thyroid hormone. Such disorders include cancer without limitation on the type of cancer, autoimmune diseases, and muscular diseases.

Aspects of the methods of the present disclosure include, in part, treatment of a mammal. A mammal includes a human, and a human can be a patient. Other aspects of the present disclosure provide, in part, an individual. An individual includes a mammal and a human, and a human can be a patient.

A combination of a RXR agonist disclosed herein and a thyroid hormone, is generally administered to an individual as a pharmaceutical composition. Pharmaceutical compositions may be prepared by combining a therapeutically effective amount of at least one RXR agonist and one thyroid hormone, or pharmaceutically acceptable acid addition salts thereof, as an active ingredient, with conventional acceptable pharmaceutical excipients, and by preparation of unit dosage forms suitable for therapeutic use. As used herein, the term "pharmaceutical composition" refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

A pharmaceutical composition produced using the methods disclosed herein may be a liquid formulation, semi-solid formulation, or a solid formulation. A formulation disclosed herein can be produced in a manner to form one phase, such as, e.g., an oil or a solid. Alternatively, a formulation disclosed herein can be produced in a manner to form two phase, such as, e.g., an emulsion. A pharmaceutical composition disclosed herein intended for such administration may be prepared according to any method known to the art for the manufacture of pharmaceutical compositions.

Liquid formulations suitable for parenteral injection or for nasal sprays may comprise physiologically acceptable sterile aqueous or nonaqueous solutions, dispersions, suspensions or emulsions and sterile powders for reconstitution into sterile injectable solutions or dispersions. Formulations suitable for nasal administration may comprise physiologically acceptable sterile aqueous or nonaqueous solutions, dispersions, suspensions or emulsions. Examples of suitable aqueous and nonaqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Pharmaceutical formulations suitable for administration by inhalation include fine particle dusts or mists, which may be generated by means of various types of metered, dose pressurized aerosols, nebulizers, or insufflators.

Semi-solid formulations suitable for topical administration include, without limitation, ointments, creams, salves, and gels. In such solid formulations, the active compound may be admixed with at least one inert customary excipient (or carrier) such as, a lipid and/or polyethylene glycol.

Solid formulations suitable for oral administration include capsules, tablets, pills, powders and granules. In such solid formulations, the active compound may be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

In liquid and semi-solid formulations, a concentration of a RXR agonist typically may be between about 50 mg/mL to about 1,000 mg/mL. In aspects of this embodiment, a therapeutically effective amount of a therapeutic compound disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In semi-solid and solid formulations, an amount of a RXR agonist typically may be between about 0.01% to about 45% by weight. In aspects of this embodiment, an amount of a therapeutic compound disclosed herein may be from, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

A pharmaceutical composition disclosed herein can optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

The combination of a RXR agonist and a thyroid hormone may also be incorporated into a drug delivery platform in order to achieve a controlled release profile over time. Such a drug delivery platform comprises the combination disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., U.S. Pat. Nos. 4,756,911; 5,378,475; 7,048,946; U.S. Patent Publication 2005/0181017; U.S. Patent Publication 2005/0244464; U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a compound or combination disclosed herein over a period of about seven days or more. As used herein, the term "extended release" refers to the release of a compound or combination disclosed herein over a period of time of less than about seven days.

In aspects of this embodiment, a sustained release drug delivery platform releases a a combination of a RXR agonist and a thyroid hormone with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a combination disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a combination disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a combination disclosed herein with substantially first order release kinetics over a period of, e.g., at most 1 day after administration, at most 2 days after administration, at most 3 days after administration, at most 4 days after administration, at most 5 days after administration, or at most 6 days after administration.

Aspects of the present disclosure include, in part, administering a combination of a RXR agonist and a thyroid hormone. As used herein, the term "administering" means any delivery mechanism that provides a compound or a combination disclosed herein to an individual that potentially results in a clinically, therapeutically, or experimentally beneficial result.

Administration of a combination disclosed herein include a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; buccal, nasal, and/or inhalation administration in any acceptable form; rectal administration in any acceptable form; vaginal administration in any acceptable form; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or subretinal injection or epidural injection; intravesicular administration in any acceptable form, such as, e.g., catheter instillation; and by placement device, such as, e.g., an implant, a stent, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A combination disclosed herein can be administered to a mammal using a variety of routes. Routes of administration suitable for treating a demyelination-related disorder as disclosed herein include both local and systemic administration. Local administration results in significantly more delivery of a combination to a specific location as compared to the entire body of the mammal, whereas, systemic administration results in delivery of a combination to essentially the entire body of the individual. Routes of administration suitable for or treating a nervous system disorder as disclosed herein also include both central and peripheral administration. Central administration results in delivery of a combination to essentially the central nervous system of the individual and includes, e.g., nasal administration, intrathecal administration, epidural administration as well as a cranial injection or implant. Peripheral administration results in delivery of a compound or a combination to essentially any area of an individual outside of the central nervous system and encompasses any route of administration other than direct administration to the spine or brain. The actual route of administration of a compound or a combination disclosed herein used can be determined by a person of ordinary skill in the art by taking into account factors, including, without limitation, the type of nervous system disorder, the location of the nervous system disorder, the cause of the nervous system disorder, the severity of the nervous system disorder, the duration of treatment desired, the degree of relief desired, the duration of relief desired, the particular compound or combination used, the rate of excretion of the compound or combination used, the pharmacodynamics of the compound or combination used, the nature of the other compounds to be included in the combination, the particular route of administration, the particular characteristics, history and risk factors of the individual, such as, e.g., age, weight, general health and the like, the response of the individual to the treatment, or any combination thereof. An effective dosage amount of a compound or a combination disclosed herein can thus readily be determined by the person of ordinary skill in the art considering all criteria and utilizing his best judgment on the individual's behalf.

In an embodiment, a combination disclosed herein is administered systemically to a mammal. In another embodiment, a combination disclosed herein is administered locally to a mammal. In an aspect of this embodiment, a combination disclosed herein is administered to a site of a nervous system disorder of a mammal. In another aspect of this embodiment, a combination disclosed herein is administered to the area of a nervous system disorder of a mammal.

In other embodiments, the combination is administered directly to the nervous system by intrathecal administration, epidural administration, cranial injection or implant, or nasal administration.

In other embodiments, the RXR agonist is administered orally, buccally, by nasal, and/or inhalation administration, intravascularly, intravenously, by intraperitoneal injection, intramuscularly, subcutaneously, intraocularly injection, by epidural injection; or by intravesicular administration and the thyroid hormone is administered orally. The RXR agonist and the thyroid hormone do not need to be administered by the same route or on the same administration schedule.

Aspects of the present specification provide, in part, administering a therapeutically effective amount of a combination of a RXR agonist and a thyroid hormone. As used herein, the term "therapeutically effective amount" is synonymous with "therapeutically effective dose" and when used in reference to treating a nervous system disorder means the minimum dose of a combination necessary to achieve the desired therapeutic effect and includes a dose sufficient to reduce at least one symptom associated with a nervous system disorder. In aspects of this embodiment, a therapeutically effective amount of a combination reduces at least one symptom associated with a nervous system disorder by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a compound or a combination disclosed herein reduces at least one symptom associated with a nervous system disorder by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a compound or a combination disclosed herein reduces at least one symptom associated with a nervous system disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a combination is the dosage sufficient to reduces at least one symptom associated with a nervous system disorder for, e.g., at least one week, at least one month, at least two months, at least three months, at least four months, at least five months, at least six months, at least seven months, at least eight months, at least nine months, at least ten months, at least eleven months, or at least twelve months.

In further embodiments, treatment with the combination reduces at least one symptom, at least two symptoms, at least three symptoms, at least four symptoms, or at least five symptoms of a nervous system disorder.

The amount of active component in a combination disclosed herein for treating a nervous system disorder can be varied so that a suitable dosage is obtained. The actual therapeutically effective amount of a combination disclosed herein to be administered to a mammal can be determined by a person of ordinary skill in the art by taking into account factors, including, without limitation, the type of the demyelination-related disorder, the location of the nervous system disorder, the cause of the nervous system disorder, the severity of the nervous system disorder, the duration of treatment desired, the degree of relief desired, the duration of relief desired, the particular combination used, the rate of excretion of the combination, the pharmacodynamics of the combination, the nature of the other compounds to be included in the combination, the particular route of administration, the particular characteristics, history and risk factors of the individual, such as, e.g., age, weight, general health and the like, the response of the individual to the treatment, or any combination thereof. An effective dosage amount of a compound or a combination disclosed herein can thus readily be determined by the person of ordinary skill in the art considering all criteria and utilizing his best judgment on the individual's behalf.

Additionally, where repeated administration of a combination disclosed herein is used, the actual effective amount of compound, composition, or combination disclosed herein will further depend upon factors, including, without limitation, the frequency of administration, the half-life of the compound, composition, or combination disclosed herein, or any combination thereof. It is known by a person of ordinary skill in the art that an effective amount of a compound or a combination disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

As a non-limiting example, when administering a RXR agonist disclosed herein to a mammal, a therapeutically effective amount generally is in the range of about 0.001 mg/kg/day to about 100.0 mg/kg/day. In aspects of this embodiment, an effective amount of a compound disclosed herein can be, e.g., about 0.01 mg/kg/day to about 0.1 mg/kg/day, about 0.03 mg/kg/day to about 3.0 mg/kg/day, about 0.1 mg/kg/day to about 3.0 mg/kg/day, or about 0.3 mg/kg/day to about 3.0 mg/kg/day. In yet other aspects of this embodiment, a therapeutically effective amount of a compound disclosed herein can be, e.g., at least 0.001 mg/kg/day, at least 0.01 mg/kg/day, at least 0.1 mg/kg/day, at least 1.0 mg/kg/day, at least 10 mg/kg/day, or at least 100 mg/kg/day. In yet other aspects of this embodiment, a therapeutically effective amount of a compound disclosed herein can be, e.g., at most 0.001 mg/kg/day, at most 0.01 mg/kg/day, at most 0.1 mg/kg/day, at most 1.0 mg/kg/day, at most 10 mg/kg/day, or at most 100 mg/kg/day.

In other embodiments, the RXR agonist is administered to a mammal in a therapeutically effective amount generally in the range of about 0.001 mg/day to about 100 mg/day, about 0.1 mg/day to about 50 mg/day, about 0.5 mg/day to about 40 mg/day, about 1 mg/day to about 30 mg/day, or about 1 mg/day to about 20 mg/day.

Suitable thyroxine doses are generally from about 5 µg/day to about 250 µg/day orally initially with an increase in dose every 2-4 weeks as needed. In other embodiments, the suitable thyroxine dose is from about 5 µg/day to about 225 µg/day, from about 7.5 µg/day to about 200 µg/day, from about 10 µg/day to about 175 µg/day, from about 12.5 µg/day to about 150 µg/day, from about 15 µg/day to about 125 µg/day, from about 17.5 µg/day to about 100 µg/day, from about 20 µg/day to about 100 µg/day, from about 22.5 µg/day to about 100 µg/day, from about 25 µg/day to about 100 µg/day, from about 5 µg/day to about 200 µg/day, from about 5 µg/day to about 100 µg/day, from about 7.5 µg/day to about 90 µg/day, from about 10 µg/day to about 80 µg/day, from about 12.5 µg/day to about 60 µg/day, or from about 15 µg/day to about 50 µg/day. Increases in dose are generally made in increments of about 5 µg/day, about 7.5 µg/day, about 10 µg/day, about 12.5 µg/day, about 15 µg/day, about 20 µg/day, or about 25 µg/day. In certain embodiments, the suitable thyroid hormone dose is a dose able to produce serum levels of T4 in the top 50%, the top 60%, the top 70%, the top 80%, or the top 90% of the normal range for the testing laboratory. As the normal range of T4 levels may vary by testing laboratory, the target T4 levels are based on normal ranges determined for each particular testing laboratory.

Dosing can be single dosage or cumulative (serial dosing), and can be readily determined by one skilled in the art. For instance, treatment of a nervous system disorder may comprise a one-time administration of an effective dose of a combination disclosed herein. As a non-limiting example, an effective dose of a combination disclosed herein can be administered once to a mammal, e.g., as a single injection or deposition at or near the site exhibiting a symptom of a nervous system disorder or a single oral administration of the combination. Alternatively, treatment of a nervous system disorder may comprise multiple administrations of an effective dose of a combination disclosed herein carried out over a range of time periods, such as, e.g., daily, once every few days, weekly, monthly or yearly. As a non-limiting example, a combination disclosed herein can be administered once or twice weekly to a mammal. The timing of administration can vary from mammal to mammal, depending upon such factors as the severity of a mammal's symptoms. For example, an effective dose of a combination disclosed herein can be administered to a mammal once a month for an indefinite period of time, or until the mammal no longer requires therapy. A person of ordinary skill in the art will recognize that the condition of the mammal can be monitored throughout the course of treatment and that the effective amount of a combination disclosed herein that is administered can be adjusted accordingly. Additionally, each element of the combination, for example the RXR agonist and the thyroid hormone, can be administered by different routes and on different schedules and are optionally administered individually, although both compositions (the RXR agonist and the thyroid hormone) are administered to the individual such that plasma levels of both compounds are detectable at the same time.

A combination disclosed herein as disclosed herein can also be administered to a mammal in combination with other therapeutic compounds to increase the overall therapeutic effect of the treatment. The use of multiple compounds to treat an indication can increase the beneficial effects while reducing the presence of side effects.

Also disclosed herein are combinations of a RXR agonist and a thyroid hormone co-administered with one or more neurotrophic factors, including but not limited to brain-derived neurotrophic factor (BDNF), glial-derived neurotrophic factor (GDNF), nerve growth factor (NGF), neurotrophin-3 (NT-3), fibroblast growth factor, basic (bFGF), ciliary neurotrophic factor (CNTF), neurotrophic factors-4/5 (NT-4/5), insulin-like growth factor (IGF), insulin; or another neurotrophic factor; or a synthetic mimetic molecule effecting similar biological activities as BDNF, GDNF, NGF, NT-3, bFGF, CNTF, NT-4/5, IGF, insulin or another neurotrophic factor.

Administration of a combination of a RXR agonist and thyroid hormone with a neurotrophic factor, or a neurotrophic factor mimetic, may be used to affect neuroprotection, i.e enhanced survival of various types of neural system cells (including neurons and glial cells).

In addition, administration of a combination of a RXR agonist and thyroid hormone with a neurotrophic factor, or a neurotrophic factor mimetic, may be used to effect repair of damaged neural system cells (including neurons and glial cells), as manifested by promotion of neurite outgrowth, resulting in formation and/or restoration of neural connections; or formation or restoration of glial structures, such as myelin sheaths around neurons, which are essential for supporting optimal neuronal signal transmission and nervous system functions.

Specific examples of uses of a combination of a RXR agonist and thyroid hormone with a neurotrophic factor or neurotrophic factor mimetic include, but are not limited to: co-administration of a combination of a thyroid hormone and a RXR agonist such as IRX4204 or bexarotene, with GDNF or a GDNF mimetic, to promote dopaminergic neuron survival, or promote repair or restoration of dopaminergic neurons, in patients with Parkinson's disease or other diseases of dopaminergic neurons; co-administration with GDNF or a GDNF mimetic to enhance survival or promote repair or restoration of motor neurons in patients with amyotrophic lateral sclerosis; co-administration with BDNF or a BDNF mimetic, or with insulin or insulin-like growth factor, to enhance survival or promote repair or restoration of cortical or hippocampal neurons in Alzheimer's disease; or co-administration with NGF to enhance survival or promote repair or restoration of sensory neurons in patients with peripheral neuropathies. Other combinations of a RXR agonist and thyroid hormone with other neurotrophic factors or neurotrophic factor mimetics, may be used for enhancing survival or promoting repair or restoration of neurons or glial cells for additional diseases of the central or peripheral nervous systems, including but not limited to multiple sclerosis of various forms, including relapsing-remitting or progressive multiple sclerosis; optic neuritis; stroke of various etiologies; nervous system trauma of various types; neuropathies of various etiologies; nervous system hypoxia; toxic insults of the nervous system of various types; dementias of various etiologies; retinopathies of various etiologies; Huntington's disease, various synucleinopathies such as progressive supranuclear palsy; epilepsy; autism; schizophrenia; depression, or aging-related nervous system degeneration.

In the above embodiments, the neurotrophic factor or neurotrophic factor mimetic may be delivered to the patient orally, or by a parenteral route, or by a topical route such as nasally, or as an inhaled medicament; or alternatively by means of an implantable or wearable slow release formulation or slow delivery device.

A combination of a RXR agonist and thyroid hormone and a neurotrophic factor, or neurotrophic factor mimetic also may be used for in vitro promotion of survival or growth of neurons or glial cells of various types, for subsequent implantation into the nervous system of a patient with a neurologic disease.

Aspects of the present specification may also be described as follows:

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of treating an autoimmune disorder, a nervous disorder, and/or a demyelination-related disorder, using the RXR agonists in combination with a thyroid hormone disclosed herein, uses of a RXR agonist and a thyroid hormone disclosed herein to manufacture a medicament and/or treat an autoimmune disorder, a nervous system disorder, and/or a demyelination-related disorder.

Example 1

Selective RXR Agonist, IRX4204, Exerts its Biological Effects Through RXR Signaling To determine whether a RXR agonist can mediate its effects via RXRα receptor homodimers, RXRβ receptor homodimers, RXRγ receptor homodimers, or any combination thereof, or the corresponding RAR/RXR heterodimers, receptor-mediated transactivation assays were performed. For transactivation assays assessing RXR homodimer signaling, CV-1 cells were transfected with 1) an expression construct including a full length RXRα, RXRβ, or RXRγ; and 2) a rCRBPII/RXRE-tk-Luc reporter construct that included RXR homodimer-specific RXRE/DR1 responsive element linked to a luciferase gene. For transactivation assays assessing RAR/RXR heterodimer signaling, CV-1 cells were transfected with 1) an expression construct comprising a fusion protein including an estrogen receptor (ER) DNA binding domain linked to the ligand binding domain of RARα, RARβ, or RARγ and 2) a ERE-tk-Luc reporter construct that included an estrogen receptor responsive element linked to a luciferase gene. The ER-RAR fusion proteins provided an accurate readout of only the transfected ER-RAR. After transfection, CV-1 cells were treated with RXR agonist IRX4204 at increasing concentrations for 20 hours before measuring luciferase activity. Luciferase activity is expressed as percent of maximal activity obtained using 1 μM RXR agonist IRX4204 for RXRs and 1 μM all-trans-retinoic acid (ATRA) for RARs (Table 1). Data are mean values±SE from five independent experiments.

TABLE 1

| Com-pound | $EC_{50}$ (nM) Efficacy (% of 1 μM IRX4204) | | | $EC_{50}$ (nM) Efficacy (% of 1 μM ATRA) | | |
| --- | --- | --- | --- | --- | --- | --- |
| | RXRα | RXRβ | RXRγ | RARα | RARβ | RARγ |
| IRX4204 | 0.08 ± 0.01 100 | 0.47 ± 0.05 100 | 0.09 ± 0.01 100 | >1,000 | >1,000 | >1,000 |

These results indicate that RXR agonist IRX4204 activated RXR receptors with very high potency ($EC_{50}$<0.5 nM) for all three RXR subtypes (Table 1). In contrast, $EC_{50}$ of the RXR agonist for RARs was >1,000 nM with minimal activity detected at >1 μM. This difference represents >2,000-fold selectivity for RXRs over RARs in functional transactivation assays. Additionally, these data demonstrate that RXR agonist IRX4204 was more than 1,000-fold more potent in activating RXR receptors rather than RAR receptors. These results indicate that Treg differentiation was mediated through a RXR signaling pathway and not via a RAR signaling pathway. Also, using appropriate receptor and reporter constructs, RXR agonist IRX4204 was shown not to transactivate so called "permissive RXR heterodimers" PPAR/RXR, FXR/RXR and LXR/RXR (FIG. 1A-C). In this regard, RXR agonist IRX4204 is distinct from other RXR agonists. Additionally, IRX4204 selectively activates the Nurr1/RXR permissive heterodimer (FIG. 1D). Thus, RXR agonist IRX4204 has a unique profile in that it selectively activates only RXR homodimers and Nurr1/RXR heterodimers.

Example 2

Binding Affinity of RXR Agonists

To determine the binding affinity for a RXR agonist, competitive displacement assays were performed. RXRα, RXRβ, RXRγ, RARα, RARβ, or RARγ were expressed in SF21 cells using a baculovirus expression system and the resulting proteins were purified. To determine the binding affinity for a RXR agonist for an RXR, purified RXRα, RXRβ, and RXRγ were separately incubated with 10 nM [$^3$H]-9CRA, and the binding affinity of the RXR agonist IRX4204 was determined by competitive displacement of [$^3$H]-9CRA from the receptor. To determine the binding affinity for a RXR agonist for an RAR, purified RARα, RARβ, and RARγ were incubated with 5 nM [$^3$H]-ATRA, and the binding affinity of the RXR agonist IRX4204 was determined by competitive displacement of [$^3$H]-ATRA from the receptor. Ki values are mean values of at least two independent experiments (Table 2). Standard errors (±) among independent experiments are indicated.

As shown in Table 2, RXR agonist IRX4204 displayed high affinity for RXRα, RXRβ, and RXRγ with Ki values being 1.7, 16, and 43 nM, respectively. In contrast, the RXR agonist IRX4204 bound with very low affinity to each of the RARs (Ki values being >1,000 nM). These data indicate that IRX4204 is highly selective for the RXRs relative to the RARs.

TABLE 2

| | RXR Binding Affinity Ki (nM) | | | RAR Binding Affinity Ki (nM) | | |
| --- | --- | --- | --- | --- | --- | --- |
| Compound | RXRα | RXRβ | RXRγ | RXRα | RXRβ | RXRγ |
| IRX4204 | 1.7 ± 0.1 | 16 ± 1.0 | 43 ± 3.0 | 6344 ± 674 | 7552 ± 638 | 4742 ± 405 |

Example 3

RXR Agonists Attenuate EAE in B6 Mice

To determine whether a RXR agonist can attenuate multiple sclerosis, C57BL/6 (B6) mice were immunized (day 0) to induce experimental autoimmune encephalomyelitis (EAE) by subcutaneous (s.c.) injection at the base of their spine with 200 μL of adjuvant containing 125 μg myelin oligodendrocyte glycoprotein peptide (35-55) (MOG peptide; Peptides International, Louisville, Ky.) and 400 μg non-viable *M. tuberculosis* H37 desiccate emulsified in a mixture of incomplete Freund's adjuvant and phosphate buffered saline (PBS). Mice were also given 200 ng of pertussis toxin in PBS administered by inter-peritoneal (i.p.) injection on the same day as MOG emulsion injection (day 0) and 2 days later (day 2). Starting on day 7 after immunization, mice were given the RXR agonist IRX4204 (50 μg), vehicle control (i.p.), thyroxine (T4), or IRX4204+ thyroxine every other day for the duration of the experiment (n=6-7 mice/group). Statistics show the results of a Mann Whitney test (analyzed from start of treatment to the end of the experiment). Mice were scored using the following scale: 0—Mice have no disease, 1—Mice have distal limp tail or rear leg weakness (paresis), 1.5—Mice have distal limp tail and rear leg weakness, 2—Mice have complete limp tail and rear leg weakness, 2.5—Mice have complete limp tail and weakness in both rear legs, 3—Mice have complete limp tail and paralysis in both rear legs, 3.5—Mice have complete limp tail, paralysis in both rear legs, and forelimb weakness. Mice receiving a score of 3.5 were immediately euthanized.

Figure 2:
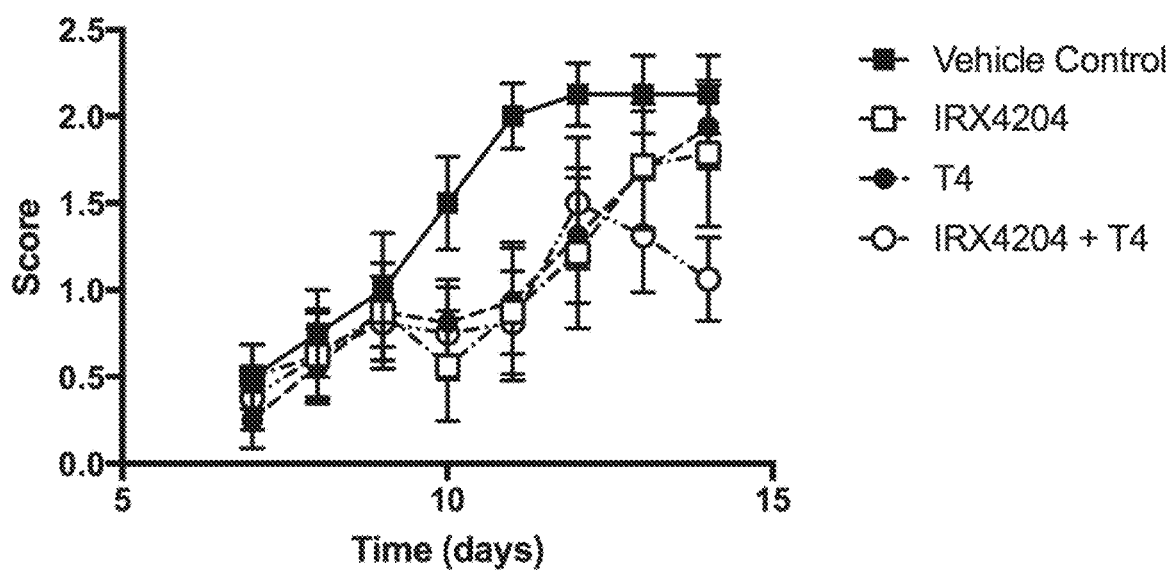
FIG. 2 shows that RXR agonists combined with thyroid hormone attenuate experimental autoimmune encephalomyelitis (EAE) in C57BL/6 mice.

FIG. 2 depicts scores of disease severity over time. The results indicate that administration of the RXR agonist IRX4204 at 50 μg significantly reduces the symptoms of EAE in mice. Efficacy of the RXR agonist was observed after the first administration (day 7) and maintained throughout the course of the study (day 20). However, the combination of IRX4204 and thyroxine reduced the symptoms of EAE in mice to an even greater degree (FIG. 2).

A dose titration experiment was also conducted in EAE mice. EAE was induced in 28 B6 mice with MOG/CFA and PT as above. Mice were scored on day 7 as indicated above and divided into groups by score so means are as equal as possible. Starting day 8, mice were scored and injected with a vehicle control or IRX4204 (50 μg, 100 μg, or 200 μg) every day.

The mice were weighed at the beginning of experiment and every day they had a score of 2.5 or higher and mice were euthanized if they lost 15% or more of their start weight. All mice that were treated with IRX4204 had significantly less disease overall (FIG. 7). At the completion of the experiment, the vehicle control and 200 μg/day groups were euthanized and spleen and CNS samples obtained.

Figure 8A:
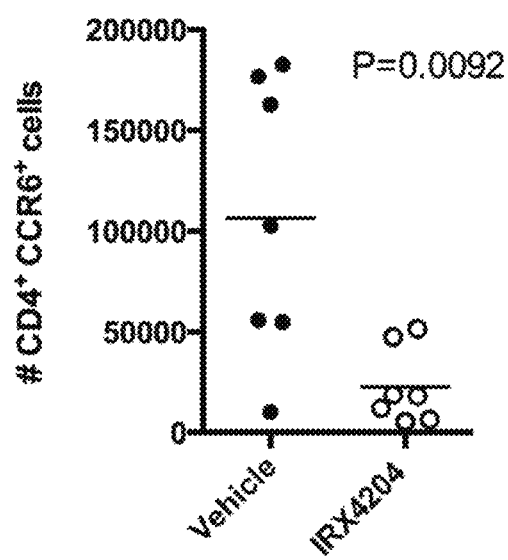
FIGS. 8A-B depicts expression of CCR6 (FIG. 8A) and CD49d (FIG. 8B) on splenocytes from EAE mice treated with 200 μg/day of IRX4204 or control.
Figure 8B:
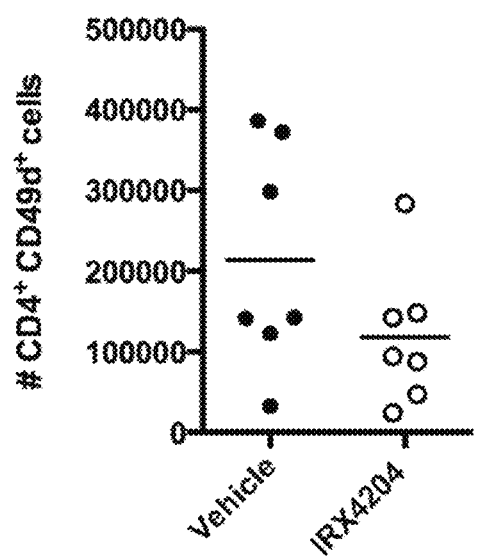
Figure 9A:
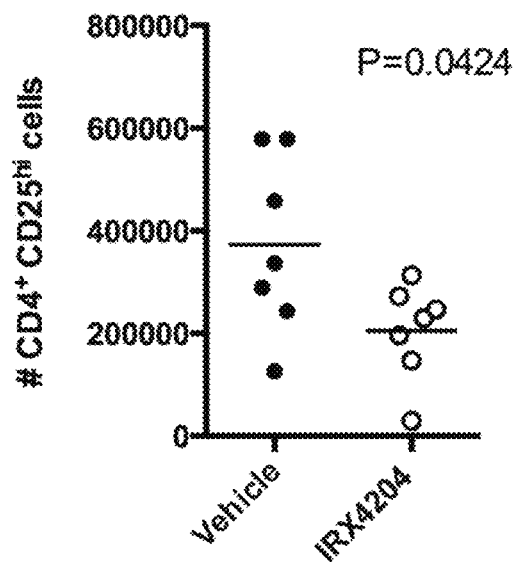
FIGS. 9A-D depicts quantification (FIG. 9A) and frequency (FIG. 9B) of CD4+CD25hi cells, total number of effector and memory CD4 T cells (FIG. 9C), and total number of activated CD4 T cells (FIG. 9D) in splenocytes from EAE mice treated with 200 μg/day of IRX4204 or control.
Figure 9B:
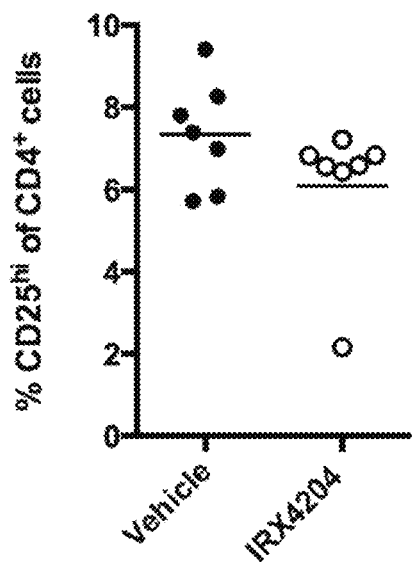
Figure 9C:
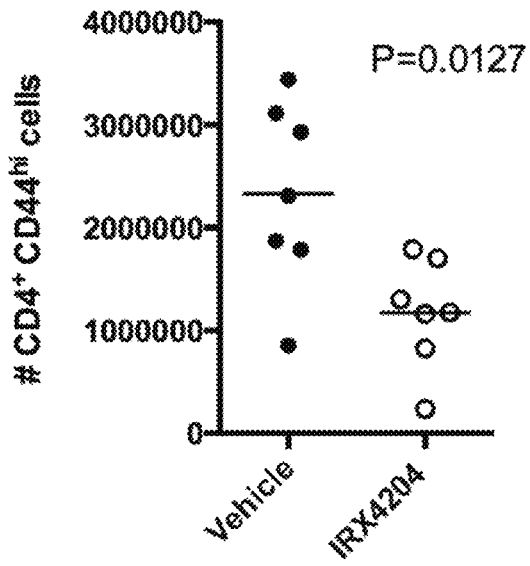
Figure 9D:
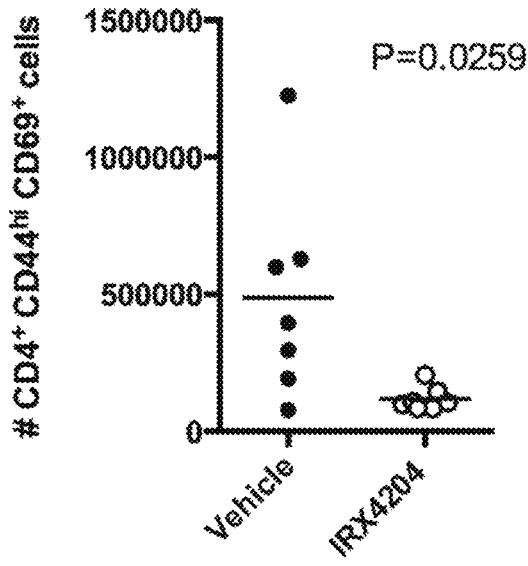

The spleen samples were evaluated for CD49d (FIG. 8A) and CCR6 (FIG. 8B), and IRX4204 treatment lowered CCR6, but not CD49d, expression on CD4 T cells. Additionally, CD4+CD25hi cells (generally consisting of TReg) were reduced, although the frequency was not altered (FIGS. 9A and 9B). The total number of effector and memory CD4 T cells, as indicated by CD44 expression, decreased with IRX4204 treatment (FIG. 12C) and the total number of recently activated CD4 T cells, as indicated by expression of both CD69 and CD44, was also decreased with IRX4204 treatment (FIG. 9D).

Figure 10:
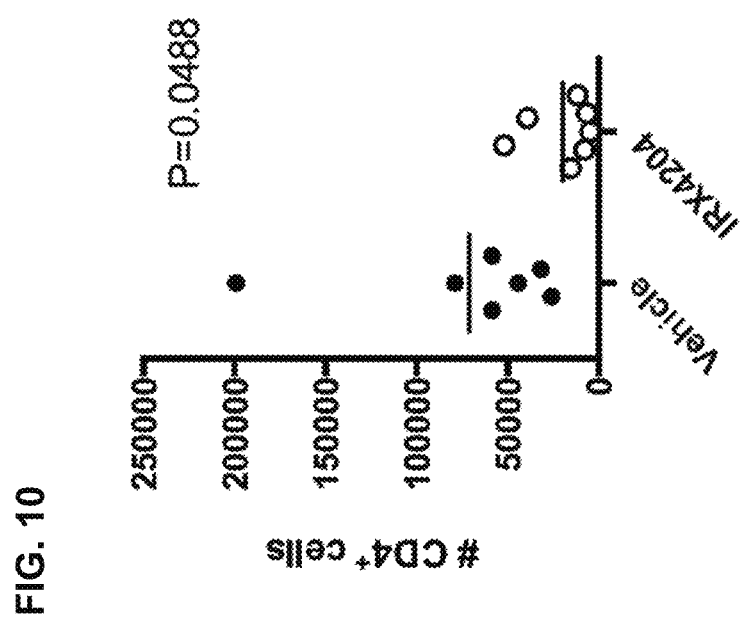
FIG. 10 depicts the total number of infiltrating CD4 T cells in the CNS of EAE mice treated with 200 μg/day of IRX4204 or control.
Figure 11A:
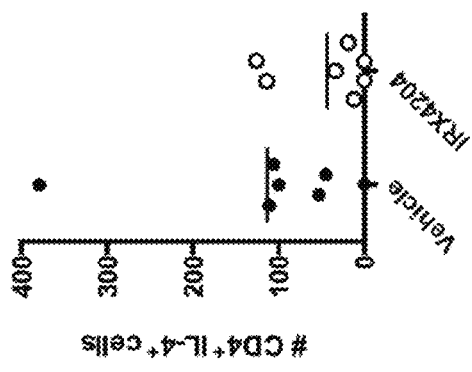
FIGS. 11A-D depicts re-stimulation of the infiltrating lymphocytes of FIG. 10 to determine expression of interferon gamma (IFNγ) (FIG. 11A), IL-17A (FIG. 11B), tumor necrosis factor (TNF) (FIG. 11C), and IL-4 (FIG. 11D).
Figure 11B:
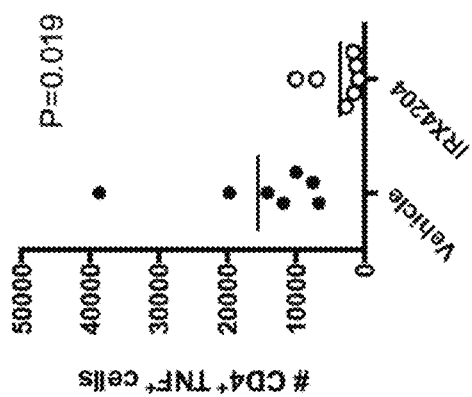
Figure 11C:
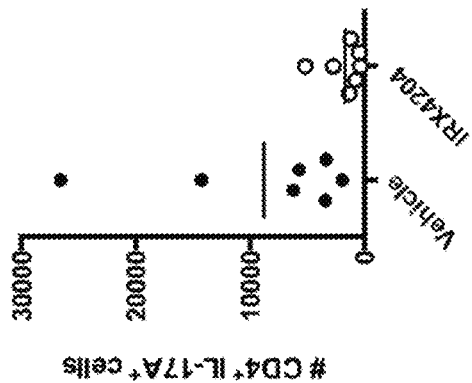
Figure 11D:
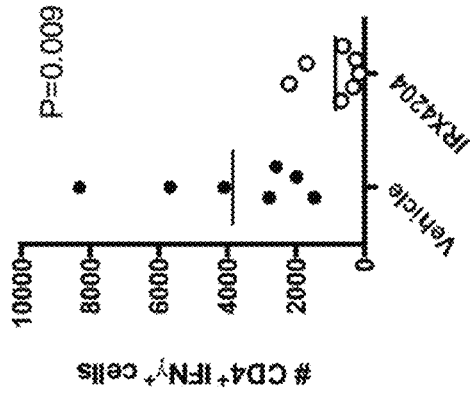
Figure 12A:
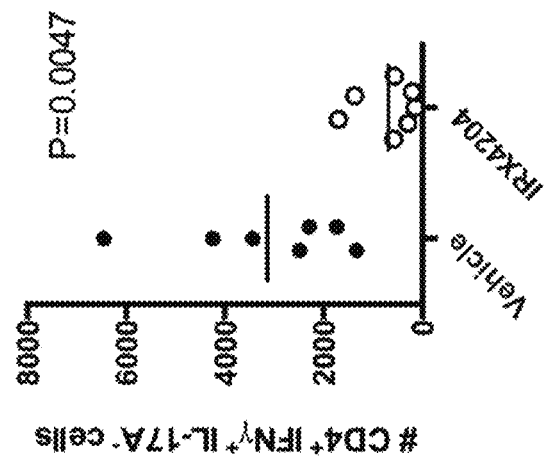
FIGS. 12A-C depicts the quantification of co-expression of IFNγ and IL-17A by CD4 T cells of FIG. 10 expressing IL-17A and not IFNγ (FIG. 12A), IL-17A and IFNγ (FIG. 12B), IFNγ and not IL-17A (FIG. 12C).
Figure 12B:
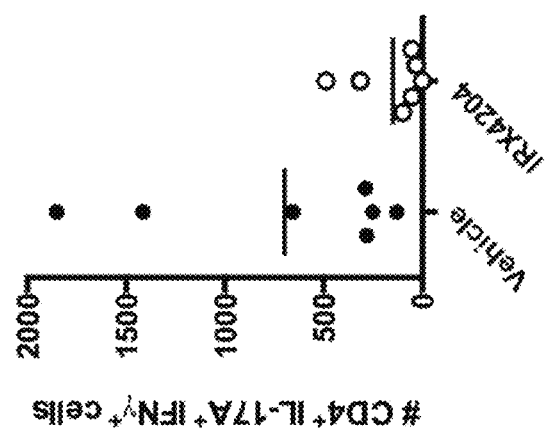
Figure 12C:
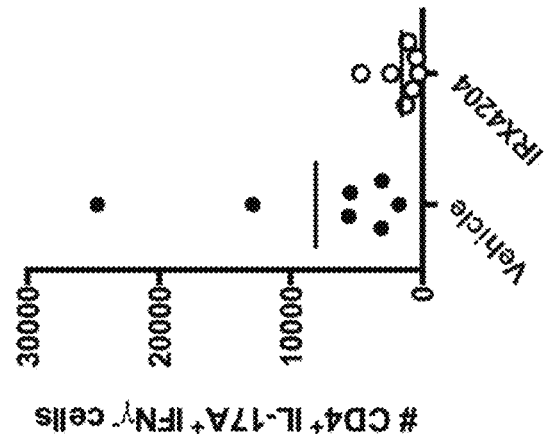

In the CNS, the total the total number of infiltrating CD4 T cells was reduced with IRX4204 treatment (FIG. 10). Restimulation with PMA/Ionomycin was used to help detect the cytokine production. Both IFNγ (FIGS. 11A and 11B) and TNF (FIGS. 11C and 11D) were significantly reduced with treatment. Co-expression of IFNg and IL-17A by CD4 T cells in CNS was quantified, but was not significantly different between groups (FIG. 12A-12C).

Example 4

RXR Agonist-Treated Mice have Reduced Central Nervous System Infiltrating Cells

To determine whether a RXR agonist can reduce central nervous system (CNS) infiltrating cells, C57BL/6 (B6) mice were treated as described in Example 3. On day 20 after immunization, mice were sacrificed and perfused with phosphate buffered saline (PBS). Brain and spinal cord tissue was isolated, digested with DNase and LIBERASE DL® (Roche Diagnostics, Indianapolis, Ind.) for 30 minutes, and homogenized through 70 micron nylon mesh filters. Resulting cells were placed over a Percoll gradient to remove myelin. The remaining cells (microglia and CNS infiltrating cells) were counted, stained for molecules of interest, and run on a flow cytometer. Based on the frequencies obtained by FACS of these cell populations, total cell numbers of CNS infiltrating leukocytes expressing CD45, including CD4+T cells and CD11c+CD11 b+myeloid dendritic cells (DC), were calculated.

Figure 3A:
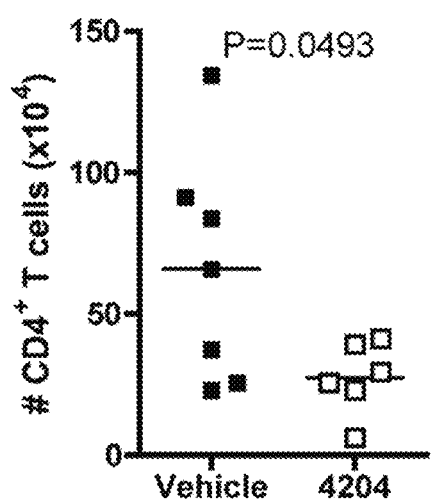
FIGS. 3A-B shows that RXR agonists reduce leukocyte infiltration into the central nervous system.
Figure 3B:
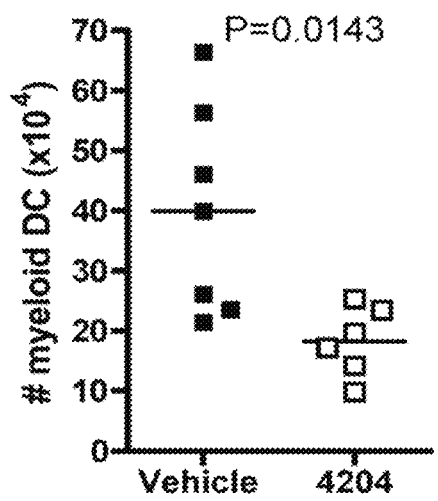

FIG. 3 depicts the number of $CD4^+$ cells (FIG. 3A) or $CD11c^+CD11b^+$ cells (myeloid DC; FIG. 3B) in mice treated with the RXR agonist IRX4204 versus the vehicle control. There was a significant reduction in the infiltration of both $CD4^+$ cells and $CD11c^+ CD11b^+$ cells in to the CNS in animals treated with a RXR agonist as compared to the control. It is expected that if the mice were treated with a combination of IRX4204 and thyroxine, there would be a further reduction of infiltration of these cells in to the CNS. As disease is propagated in the CNS through the $CD4^+$ cells infiltrating the CNS and becoming re-activated by $CD11c^+ CD11b^+$ cells, this suggests that part of the mechanism of action in this model is to limit the presence of the cells in the CNS.

Example 5

RXR Agonists Attenuate EAE in SJL Mice

To determine whether a RXR agonist can attenuate multiple sclerosis, SJL mice were immunized to induce EAE by s.c. injection at the base of their spine with 200 μL of adjuvant containing 200 μg proteolipid proteins (139-151) (PLP peptide; Peptides International, Louisville, Ky.) and 400 μg of non-viable *M. tuberculosis* H37 desiccate emulsified in a mixture of incomplete Freund's adjuvant and PBS. Mice were also given 150 ng of pertussis toxin in PBS i.p. on the same day as PLP emulsion injection and 2 days later. Starting day 7 after immunization, mice were given the RXR agonist IRX4204 (50 μg) or vehicle control i.p. every other day for the duration of the experiment (n=6 mice/ group). Mice were scored using the scale described in Example 3.

Figure 4:
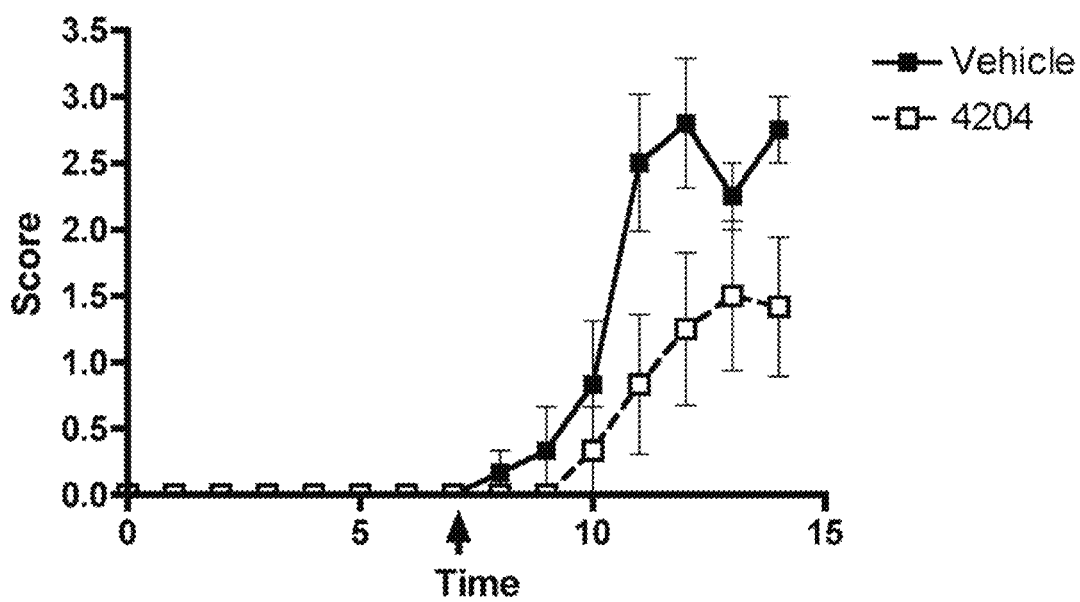
FIG. 4 shows RXR agonists attenuate EAE in SJL mice.

The results indicate that administration of the RXR agonist IRX4204 significantly reduces the symptoms of EAE in mice. Table 3 shows the features of a RXR agonist IRX4204 treatment in SLJ mice. FIG. 4 depicts scores of disease severity over time. Efficacy of the RXR agonist was observed after the second administration (day 8) and maintained throughout the course of the study (day 14). It is expected that if administration of IRX4204 was combined with thyroxine treatment, there would be a further reduction in the symptoms of EAE and disease severity scores.

TABLE 3

| RXR agonist Treatment in SJL Mice | | |
|---|---|---|
| Clinical Features | Vehicle | IRX4204 |
| Mean Maximum Score | 3.2 ± 0.6 | 1.5 ± 1.4 |
| Disease Incidence | 6/6 | 4/6 |
| Death from Disease | 4/6 | 0/6 |

Example 6

Figure 5A:
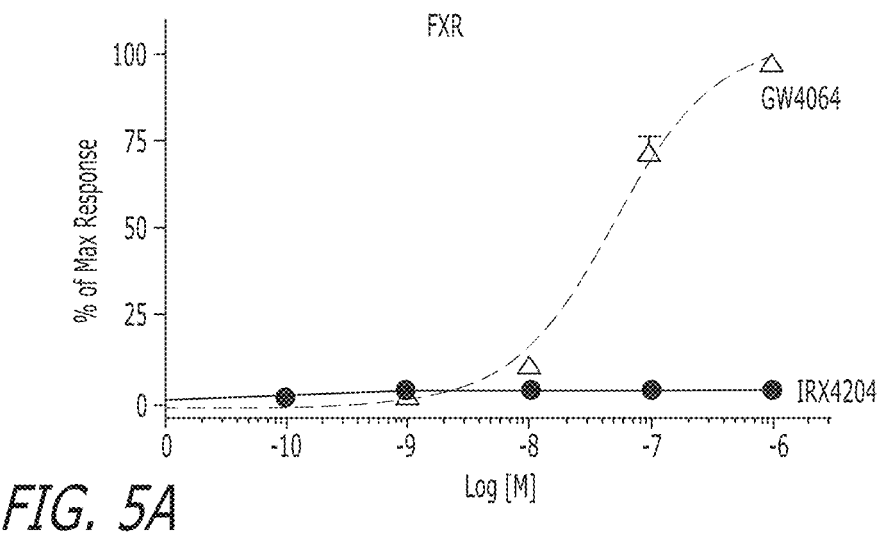
FIGS. 5A-D shows that IRX4204 selectively activates RXR-Nurr1 heterodimers. Transactivation assay of IRX4204 (194204, Formula III) for farnesoid X receptor FXR (FIG. 5A); for liver X receptors LXRα and LXRβ (FIG. 5B); for peroxisome proliferator-activated receptor PPARγ (FIG. 5C); and for Nurr1 receptor in the presence or absence of RXR (FIG. 5D).
Figure 5B:
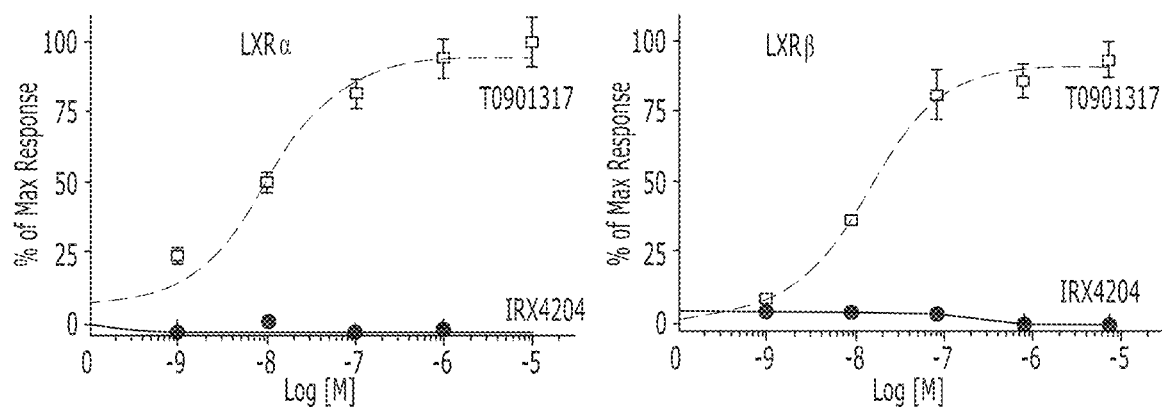
Figure 5C:
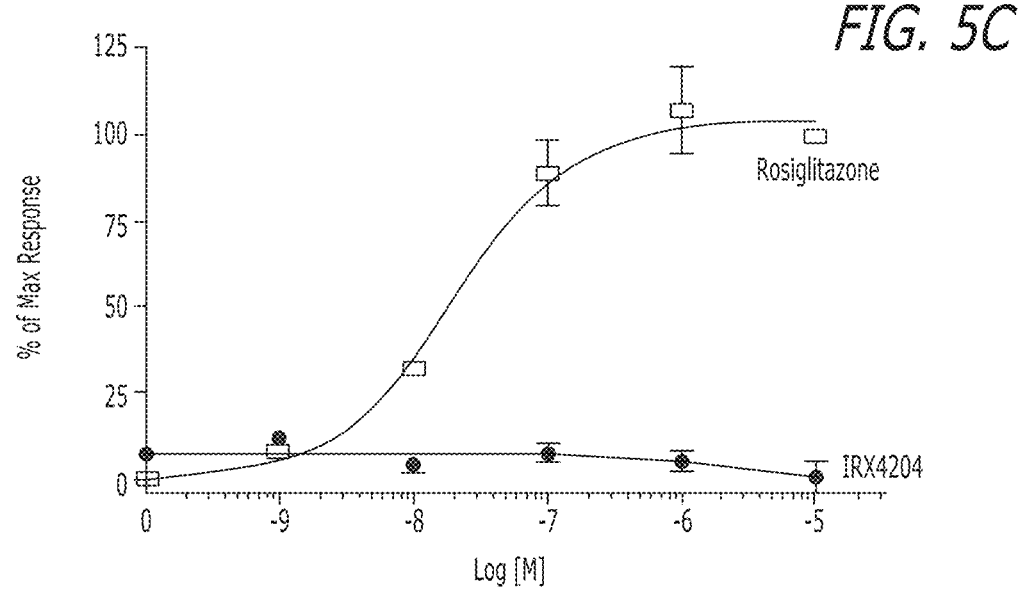
Figure 5D:
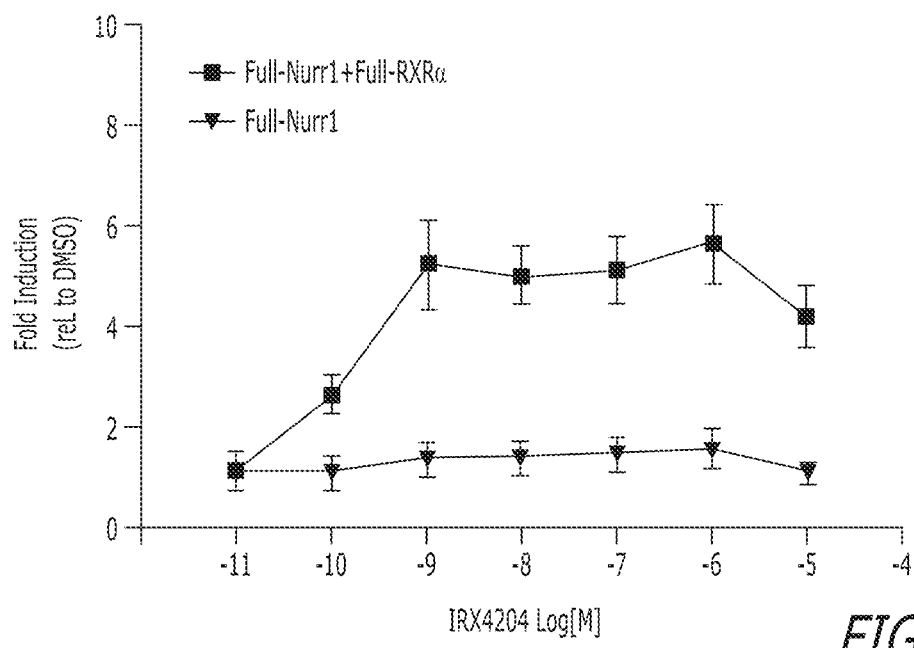

RXR Agonist IRX4204 as a Selective Activator of Nurr1/RXR Permissive Heterodimer In order to determine which permissive RXR heterodimer is activated by the RXR agonist IRX4204, receptor transactivation assays were carried out as follows for PPARγ/RXR, FXR/RXR, LXRα/RXR, LXRβ/RXR, and Nurr1/RXR. For PPARγ: CV-1 cells were transfected with 3×(rAOX/DR1)-tk-Luc reporter gene and an expression vector for PPARγ. For FXR:CV-1 cells were transfected with 3×(IBABP/IRI)-tk-Luc reporter gene and vectors for FXR and RXRα. For LXR:CV-1 cells were transfected with 3×(PLTP/LXRE)-tk-Luc reporter gene with vectors for LXRα or LXRβ. For Nurr1: COS7 cells were transfected with 3×NBRE-tk-luc reporter gene and full length Nurr-1 with or without full-length RXRα plasmid. Cells were then treated with vehicle or IRX4204 for 20 hr. Luciferase data were normalized to co-transfected β-gal activity. Luciferase activity was expressed as percent of maximal activity obtained using specific agonists. Rosiglitazone (PPARγ), GW4064 (FXR), T0901317 (LXR). The data indicate that IRX4204 does not activate FXR/RXR (FIG. 5A), LXRα/RXR or LXRβ/RXR (FIG. 5B), or PPARγ/RXR (FIG. 5C). In contrast, IRX4204 potently ($EC_{50}$<1 nm) activates the Nurr1/RXR heterodimer. These data collectively indicate that IRX4204 is a unique RXR agonist in that it selectively activates the Nurr1/RXR heterodimer but not the PPARγ/RXR, FXR/RXR or LXR/RXR heterodimers.

Example 7

Effect of RXR Agonists on Oligodendrocyte Precursor Cell Differentiation

Figure 6:
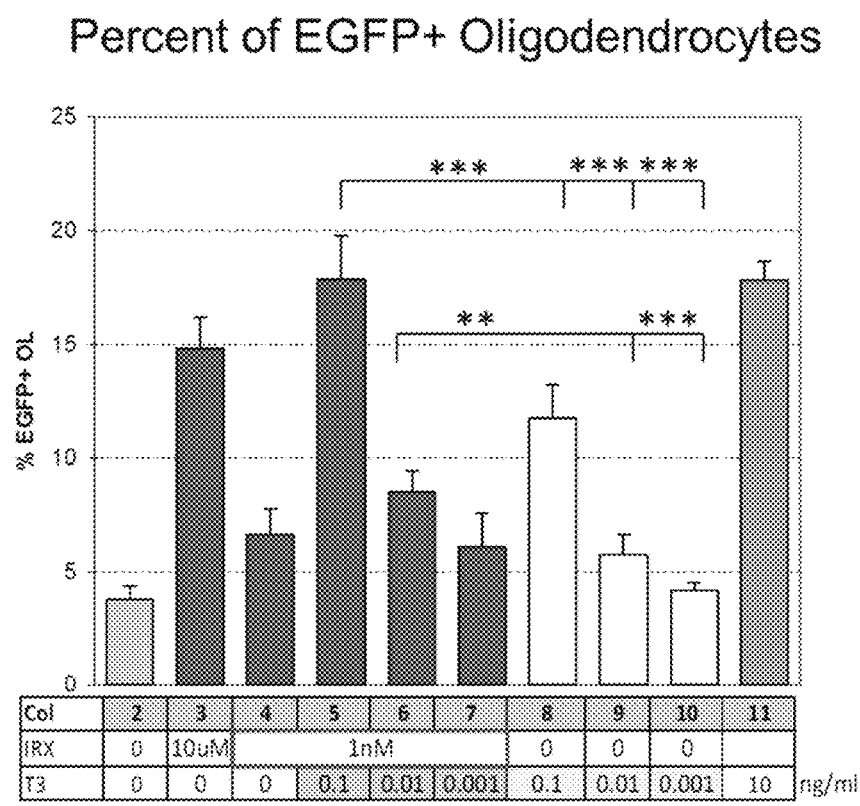
FIG. 6 shows the percentage of green fluorescent protein (EGFP) positive oligodendrocytes after culture of oligodendrocyte precursor cells derived from embryonic mouse brains with IRX4204 and thyroid hormone.

The goal of this study was to evaluate the effect of IRX4204 on differentiation of oligodendrocyte precursor cells (OPCs) into oligodendrocytes. OPCs were generated from a neurosphere culture of E14.5 PLP-EGFP (on C57BL/6J background) mouse brains. The isolated OPCs were treated with IRX4204 and/or T3 to evaluate the expression of green fluorescent protein (EGFP), which correlates with differentiation of OPCs into oligodendrocytes. The EGFP expressing cells were quantified with Cellomics Neuronal Profiling Algorithm. The positive (T3) control demonstrated differentiation of OPCs as expected. The results demonstrate that IRX4204 promotes OPC differentiation into oligodendrocytes as shown by the increase in the number of the EGFP positive cells compared to negative control (DMSO). All tested concentrations except the lowest concentration ($1^{-6}$ μM) showed a significant increase in OPC differentiation into oligodendrocytes (FIG. 6). However, addition of T3 to the IRX4204-treated cultures induced even higher levels of EGFR+ oligodendrocytes demonstrating the significant benefit of the combination of IRX4204 and thyroid hormone.

The EGFP expressing cells in controls and all compounds were quantified with Cellomics Neuronal Profiling Algorithm. The experiment was successful as demonstrated by the significant increase in % EGFP cells in positive control (T3; 8.5%) compared to the negative control (DMSO; 2.3%). IRX4204 promotes OPC differentiation into oligodendrocytes as demonstrated by the dose dependent increase in the number of the EGFP positive cells compared to negative control (DMSO). IRX4204 did not show any differences in total cell number and pyknotic cells compared to controls. The results from this study demonstrate that IRX4204 promotes OPC differentiation. The data show a dose-dependent increase in the percentage of EGFP cells compared to the negative control. These date indicate that IRX4204 promotes the growth of myelin-forming cells in cell culture.

Example 8

IRX4204 Enhances Central Nervous System (CNS) Remyelination in an In Vivo Model by Acting Directly on the Remyelination Process A focal toxin (ethidium bromide) induced rat model of demyelination is used to ascertain the direct effects of IRX4204 on acute demyelination independent of the immunomodulatory effects of IRX4204. The experiment uses rats of relatively advanced age (1 year) since such rats undergo remyelination in a less efficient manner, thereby providing data that are more relevant to the clinical treatment of human patients with multiple sclerosis or other demyelination disorders.

Focal demyelination is induced in one year old rats (approximately 300 g in weight) by injecting stereotactically 5 μl of ethidium bromide solution (0.01% vol/vol in saline) in a bilateral manner into the caudal cerebellar peduncles (CCP). Starting seven days after injection of the ethidium bromide, the rats are treated by oral gavage for fourteen days (day 7 to day 21 post-ethidium bromide treatment) with 10 mg/kg/day of IRX4204 (in DMSO and corn oil), or the same dose of oral IRX4204 plus 20 ng/g of subcutaneous thyroxine, or vehicles (DMSO and corn oil plus thyroxine vehicle) for fourteen days. The rats are killed on day 24 post-ethidium bromide treatment for analysis of remyelination by quantitative polymerase chain reaction (qPCR) and microscopy.

Analysis of the lesions revealed the following: the densities of $Olig2^+$ oligodendrocyte lineage cells and CC1+ differentiated oligodendrocytes increased in IRX4204-treated animals relative to vehicle treated animals and increased further in the IRX4204 plus thyroxine animals; Nkx2.2+ oligodendrocyte precursor cells (OPCs) increased in IRX4204-treated lesions relative to vehicle treated lesions and were highest in IRX4204 plus thyroxine treated lesions. Also, real-time qPCR analysis of lesion samples show an increase in Mbp expression and an increase in Pdgfra expression indicating higher levels of myelin regeneration in IRX4204-treated animals with highest levels of Mbp and Pdgfra expression seen in IRX4204 plus thyroxine animals. Ultrastructural analyses of CCP lesions further demonstrate that IRX4204 plus thyroxine treatment results in more remyelinated axons in animals than IRX4204 only treatment which in turn leads to more remyelinated axons than vehicle treatment. AG-ratio analysis (this ratio is that of axon diameter to myelinated axon) also shows that IRX4204-treated animals have a lower G-ratio than vehicle treated animals and that this lower ratio is due to the formation of thicker remyelinated sheaths surrounding axons in IRX4204-treated animals. The G-ratio was further reduced in animals treated with the combination of IRX4204 and thyroxine. All these findings are consistent with an increase in CNS remyelination in IRX4204-treated animals and an optimal increase in IRX4204 plus thyroxine treated animals.

Example 9

IRX4204 in Combination with Thyroid Hormone Accelerates Remyelination in the Cuprizone/Rapamycin Mouse Model of Toxic Demyelination The cuprizone (bis-cyclohexanone oxaldihydrazone) model facilitates reliable, reproducible and unequivocal analysis of myelin parameters in both white and grey matter. The cuprizone model is a model for toxic demyelination. In this model, young mice are fed with the copper chelator cuprizone, leading to oligodendrocyte death and a subsequent reversible demyelination. Cuprizone-fed mice with rapamycin, a drug that blocks mTOR and spontaneous remyelination, allows for better quantification of oligodendrocyte turnover. In the acute cuprizone paradigm, male C57BL/6 mice at 6 to 9 weeks of age are fed a diet of chow mixed with 0.2% cuprizone over the course of 6 weeks. By the third week of cuprizone feeding, consistent demyelination can be observed in the corpus callosum, the largest white matter tract in the mouse brain. Demyelination reaches a maximum at 5 or 6 weeks. Chronic demyelination can be induced if C57BL/6 mice are maintained on a diet with cuprizone for 12 weeks.

The goal of this study was to evaluate the remyelination potential of IRX4204 in a mouse model of toxic demyelination. Previous studies have demonstrated efficacy of IRX4204 in an EAE model of MS. Also, previous data demonstrates that IRX4204 can induce significant oligodendrocyte precursor cell (OPC) differentiation in vitro. The current study is conducted to further investigate the CNS effects of IRX4204 in a cuprizone model of MS on remyelination and neuroprotection.

The animals (8 week-old male C57BL/6J mice) were subjected to cuprizone diet plus rapamycin injections (CR, 10 mg/kg) for 12 weeks to induce demyelination in white matter (CC, corpus callosum). After 12 weeks, CR was discontinued and subsets of animals were treated daily for 6 weeks with either vehicle (oral IRX4204 vehicle) or IRX4204 (10 mg/kg, PO). All animals were sacrificed after 12 weeks of CR or after further 6 weeks of treatment to evaluate myelin in white matter (corpus callosum) and gray matter (hippocampus and cortex). In addition, the size of myelinated axons was quantified and the large myelinated axons were further assessed by 3D-electron microscopy (3D-EM).

Demyelinating diseases, such as MS, are characterized by myelin loss, chronic inflammation, and axonal and oligodendrocyte loss in the CNS. Although the etiology of MS remains unknown, the disease generally starts with sporadic, acute episodes and develops over time into a chronic and progressive state. The acute and chronic demyelinated lesions of MS can be demonstrated in cuprizone-diet induced mouse models that depend for severity upon the duration of cuprizone administration. Cuprizone induces extensive demyelination in adult mouse brain and simultaneous administration of rapamycin blocks the differentiation of oligodendrocytes and prevents spontaneous remyelination during the demyelination phase. This model also demonstrates the hippocampal demyelination in MS. When cuprizone+rapamycin (CR) is discontinued, there is quantifiable spontaneous remyelination in this model, which can be modified by drug intervention in the remyelination process. The 12-week CR model of demyelination provides an opportunity to evaluate the therapeutic potential of new drugs to promote remyelination in the mouse brain.

A total of 40 animals were included in the study, where all 40 animals received CR demyelination for 12 weeks. After demyelination, a subset (n=10) of animals are sacrificed to serve as controls to assess baseline demyelination. The remaining animals are divided into groups (n=15) which are treated daily with oral IRX4204 (10 mg/kg) or oral vehicle for IRX4204 for six weeks.

There was no significant difference in any of the groups with regard to body weight.

Figure 16A:
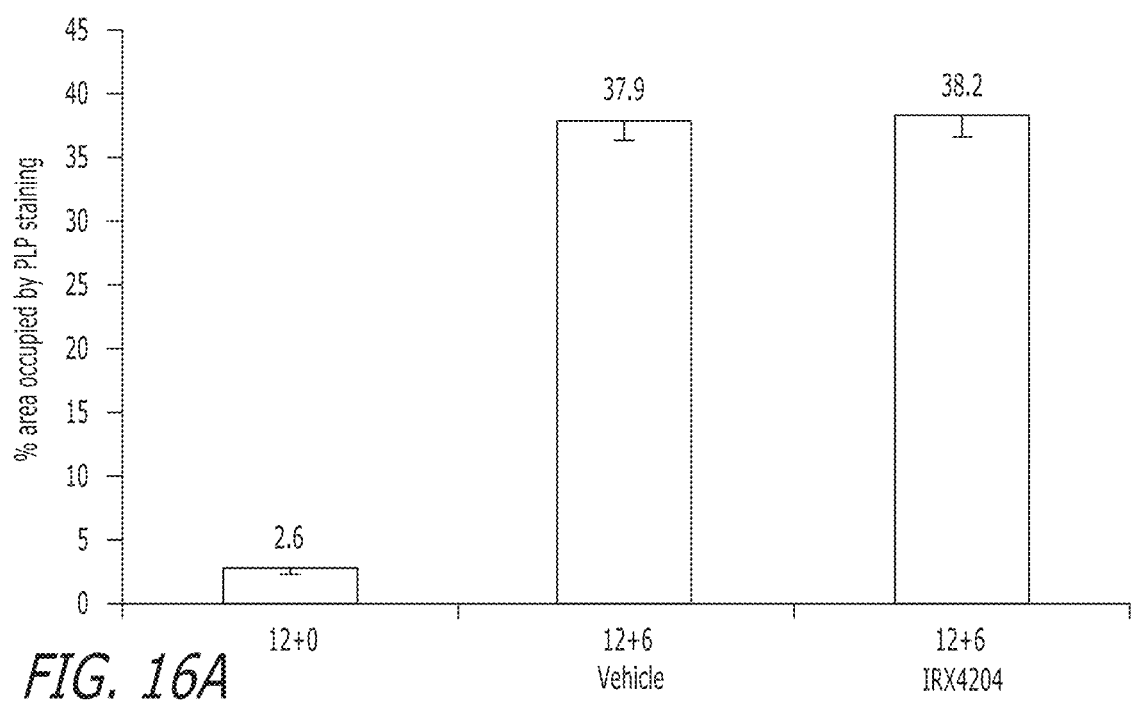
FIGS. 16A-B depicts the effect of IRX4204 on remyelination in a cuprizone-induced demyelination model.
Figure 16B:
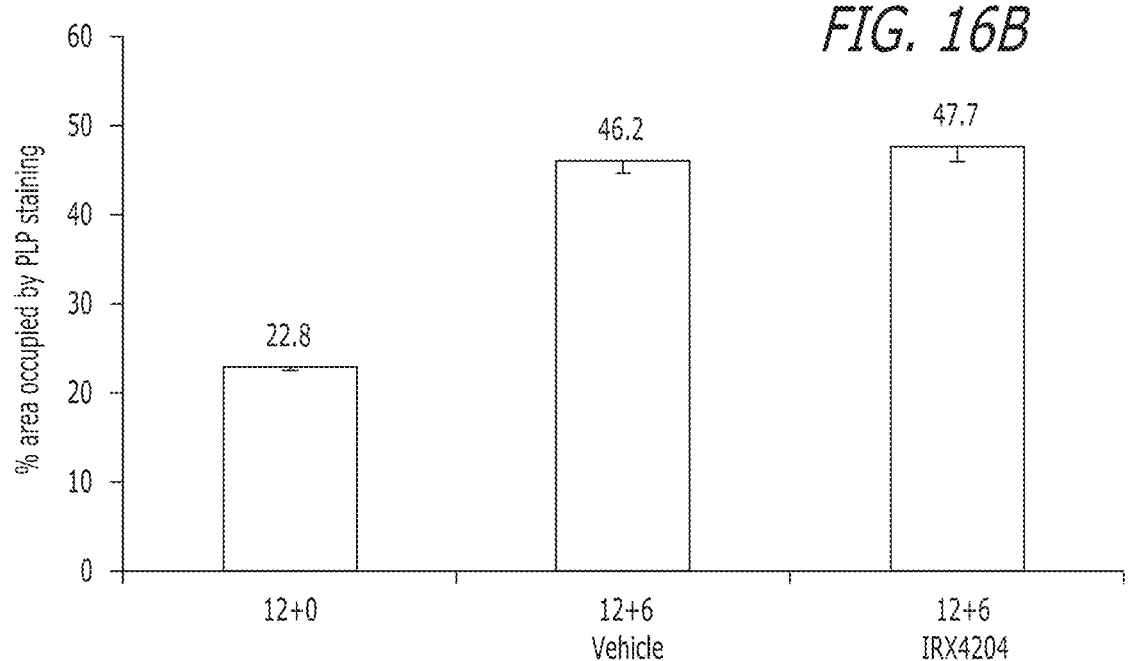

Floating brain sections are immunostained with myelin prolipid protein (PLP) to visualize and quantify myelin in gray matter, hippocampus (FIG. 16A) and cortex (FIG. 16B). The percentage area covered by PLP staining in animals treated with vehicles only after discontinuation of the demyelination regimen is significantly greater than in animals who were sacrificed immediately after CR demyelination demonstrating the occurrence of spontaneous remyelination.

Figure 17A:
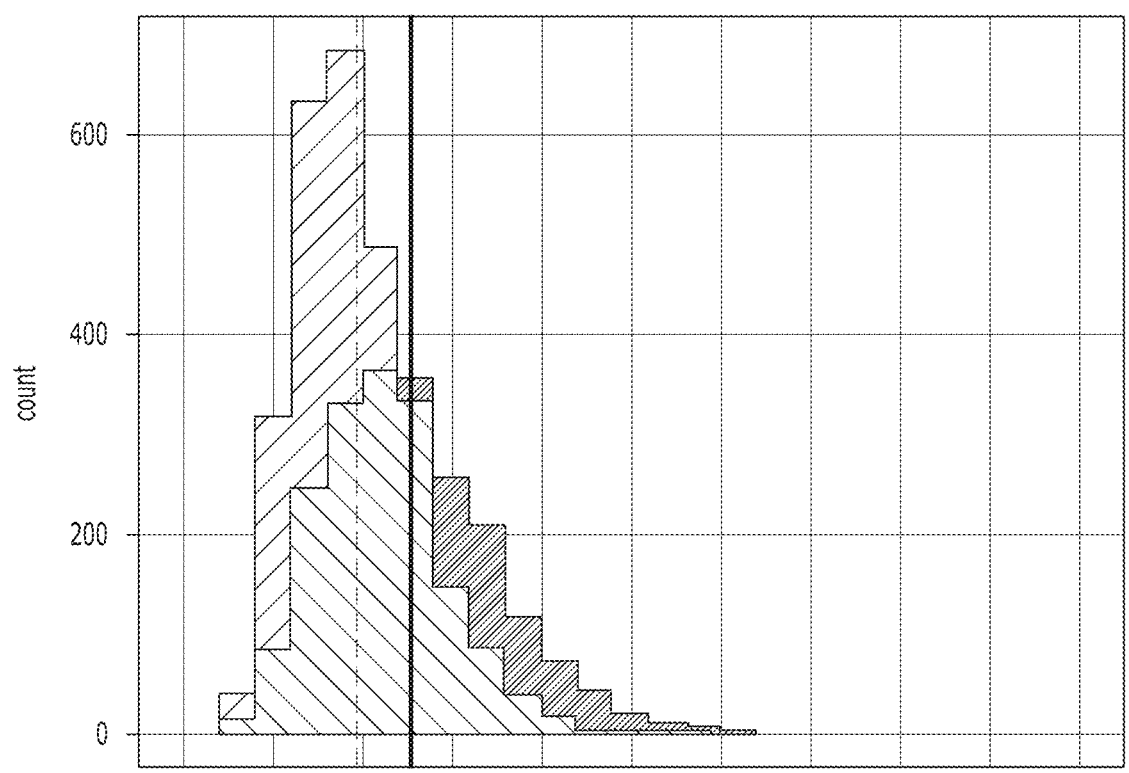
FIGS. 17A-B depicts quantitation of the size of myelinated axons. The size of myelinated axons after 6 weeks of treatment were quantified by Image J. Histogram of axon size distribution demonstrates a shift in distribution to larger axon diameter in IRX4204-treated axons (FIG. 17A). Examination of the 3rd quartile date of axons about 0.7 μm demonstrates a significant increase (P<0.0001) in the size of axons in the upper quartile (FIG. 17B).
Figure 17B:
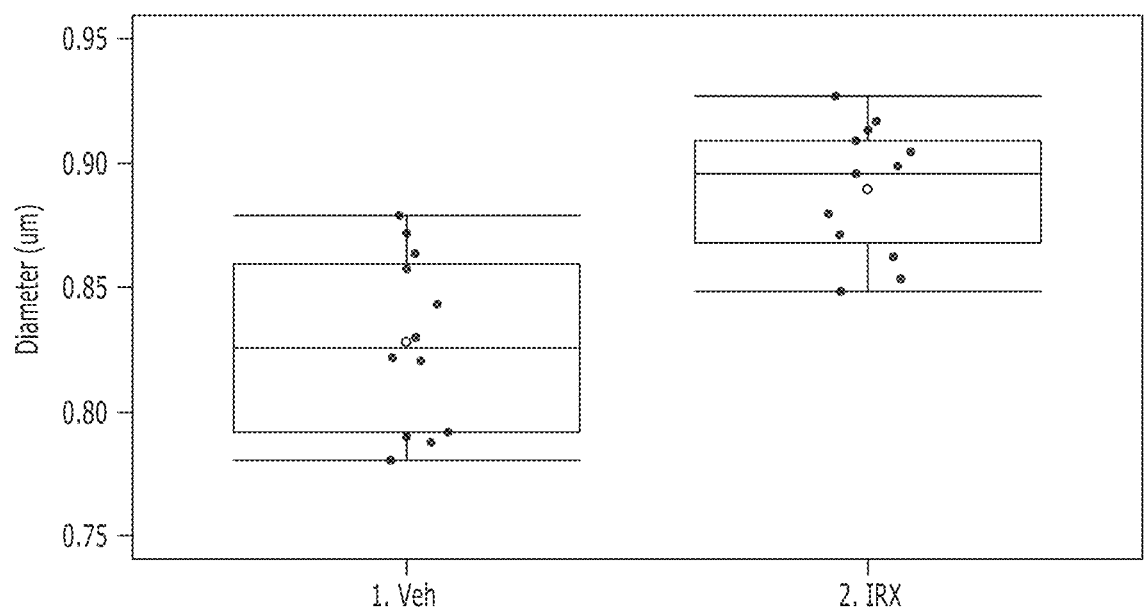
Figure 18:
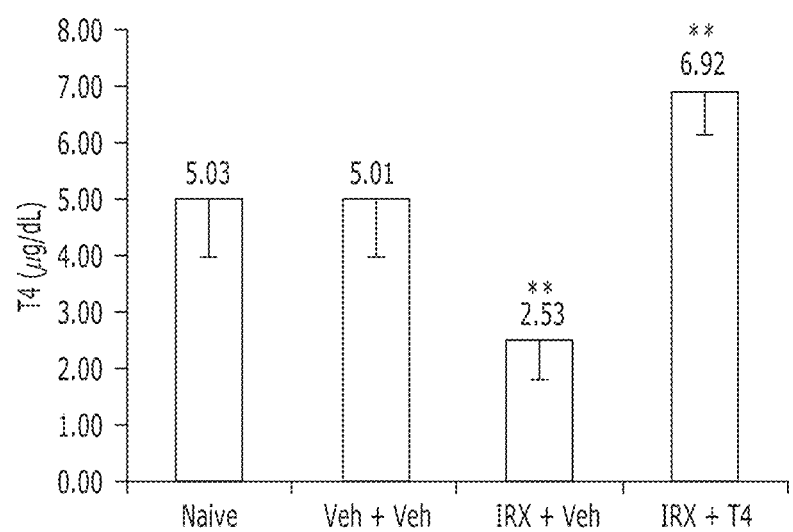
FIG. 18 depicts terminal circulating serum T4 levels in animals that received vehicle, IRX4204, or IRX4204 and T4 (** P<0.005 vs vehicle and naïve control).
Figure 19:
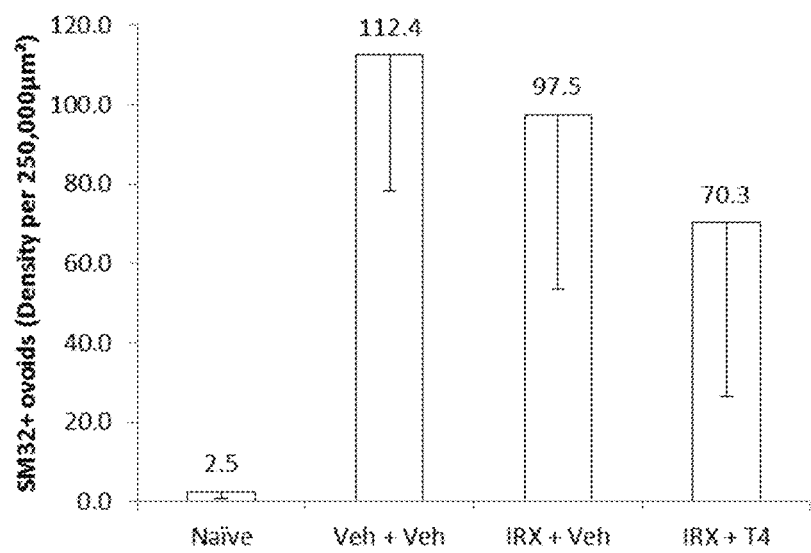
FIG. 19 depicts a quantification of SMI32 positive ovoids in corpus callosum in animals that received vehicle, IRX4204, or IRX4204 and T4 for 6 weeks (* P<0.05 vs Veh+Veh Control).

In this study, the 12-week demyelination model is used to assess CNS effects of IRX4204, with and without thyroid hormone supplementation, following 6-weeks of treatment. The results from this study demonstrate that IRX4204 significantly increases the size of myelinated axons in the corpus callosum (FIG. 17). In addition, these large myelinated fibers demonstrate a healthy phenotype. Thus, IRX4204 and has a neuroprotective effect on myelinated neurons.

Additionally, IRX4204 plus thyroxine increases the number and density of myelinated axons in white and gray matter in addition to increasing the size of myelinated axons in the corpus callosum.

Example 10

Evaluation of the Neuroprotective Potential of IRX4204 and IRX4204+Thyroxine in a Mouse Model of Non-Immune Mediated Demyelination The modified cuprizone model (cuprizone+rapamycin) facilitates reliable, reproducible and unequivocal analysis of neurodegeneration caused by demyelination. SMI-32 immunostaining enables the visualization and quantification of swollen and transected axons (ovoids) in the corpus callosum and enables the assessment of the extent of axonal degeneration. There were four groups of mice in the study: cuprizone+rapamycin (CR) only (n=6), CR+ vehicles (n=12), CR+IRX4204 (n=12), and CR+IRX4204+thyroxine (n=12). The test articles were administered concurrently with CR for 6 weeks. IRX4204 was administered orally once daily at 10 mg/kg body weight. Thyroxine (T4) treatment was initiated one day after initiation of the IRX4204 treatment. T4 was administered subcutaneously (SC) once daily at 20 ng/g body weight. The CR+ vehicles group received the IRX4204 vehicle (oral) and the T4 vehicle (SC). All animals were subjected to terminal blood collection to determine plasma T4 levels. After sacrifice, the density of SMI-32 positive ovoids per unit area was determined for each group. The higher the SMI-32 positive ovoid density, the greater the extent of axonal degeneration. There was a 13.3% reduction in SMI-32+ ovoids in the IRX4204 group relative to the vehicles group indicating some neuroprotection by IRX4204 alone. However, the IRX4204+thyroxine group gave a 37.5% reduction relative to the vehicles group indicating that the IRX4204 plus thyroxine combination provides a substantial degree of neuroprotection from the CR induced neurotoxicity.

Example 11

A Human Clinical Trial to Demonstrate Effects of IRX4204 in Parkinson's Disease An open-label, single site clinical study of early Parkinson's Disease subjects treated with IRX4204 was conducted to determine whether the preclinical promise of IRX4204 as a disease modifying agent for PD will translate to the clinical setting upon treatment of early PD patients with IRX4204 as determined by Unified Parkinson's Disease Rating Scale (UPDRS) measurements and safety assessments. The changes in UPDRS scores were correlated with circulating thyroxine levels.

The objectives of this study were to further characterize the safety and tolerability of IRX4204 in early patients, particularly reduction in T4 levels, and to evaluate the effect of treatment with IRX4204 on the motor symptoms of PD measured by the UPDRS.

The study endpoints were (1) the change in motor testing scores from end of dosing period (Day 17), and (2) changes in T4 levels.

(a) Design Overview

This was a single site, open-label study designed to examine efficacy (reduction in UPDRS scores) and safety of 3 dose levels of IRX4204 in cohorts of early PD patients for a period of approximately two weeks. In the three cohorts, each subject reported to the clinical research site on at least 3 occasions:

Screening (Visit 1)—Screening to determine eligibility (up to 30 days prior to Baseline Visit)

Baseline Period (Visit 2)—Treatment with IRX4204 began on Day 1.

Week 2 (Visit 3)—subjects returned to the clinic approximately 17 days after initiation of IRX4204 for safety and efficacy evaluations.

Safety and tolerability was assessed through all study visits including blood and urine samples for laboratory tests, ECGs, physical examination, neurological examination and assessments for adverse events.

To qualify for study participation, subjects were required to meet the following criteria: 40-80 years of age, inclusive; have a clinical diagnosis of PD based on the UK Brain Bank Criteria; participant has Hoehn and Yahr stage <3; participant may be treated with PD symptomatic therapy on a stable dose for at least 30 days prior to the Screening Visit. Dose levels of PD symptomatic therapies will remain stable through the study; must be willing and able to provide informed consent; females must be of either non-child bearing potential or must be willing to avoid pregnancy by using medically accepted contraception for 4 weeks prior to and 4 weeks following the last dose of study medication.

Subjects who met any of the following criteria were not included in the study: has any form of Parkinsonism other than idiopathic PD; are currently experiencing motor fluctuations (end of dose wearing off or dyskinesia) reflective of later stages of PD; has evidence of dementia or significant cognitive dysfunction; has clinically significant abnormal laboratory value and/or clinically significant unstable medical or psychiatric illness; the subject has any disorder that may interfere with drug absorption, distribution, metabolism or excretion; the subject has evidence of clinically significant gastrointestinal, cardiovascular, hepatic, pulmonary, or other disorder or disease; pregnancy or breastfeeding.

The clinical site prepared the study drug for administration by dispensing the correct dosage (20 mg/day, 10 mg/day or 5 mg/day) of IRX4204 for each subject. On Day 1, subjects received their first dose of IRX4204. After Day 1, IRX4204 drug dosing occurred at home daily. Patients took their daily dose of study medication with food approximately the same time each day, preferably between 8 AM and 10 AM. On Day 1, subjects received a 15-day supply of IRX4204 for a once daily dose of 20 mg, 10 mg, or 5 mg. Five subjects were recruited for each of the three dose levels. All fifteen subjects completed 15 days of dosing.

All subjects (n=52 total, n=12-13 per dose level) completed 15 days of dosing and returned to the clinic at the end of 2 weeks (day 15-17) for UPDRS score determination and safety assessments including determination of plasma thyroxine (T4) levels. Percent changes in Total Motor scores, Total UPDRS scores and plasma T4 values were determined according to the following:

$$\text{Percent Change} = \frac{\text{Baseline Value} - 2 \text{ Week Value}}{\text{Baseline Value}} \times 100$$

The average percent changes in Total Motor and Total UPDRS scores for the three dose levels are given in Table 4. A negative score indicates an improvement in the disease as measured by the comprehensive UPDRS evaluation. The largest therapeutic response to IRX4204 treatment as measured by the Total Motor score (−31.4%) was obtained for the lowest dose of IRX4204 (5 mg/day). Surprisingly, there was less efficacy, as measured by the Total Motor sores, at each of the higher doses, 10 mg/day (11.7%) and 20 mg/day (−14.5%). Similar results were obtained when the Total UPDRS scores were considered. The best therapeutic response was obtained with the 5 mg/day cohort (−18.7%). Each of the higher doses, 10 mg/day and 20 mg/day, were progressively less efficacious with total UPDRS changes of −13.6% and 6.6%, respectively.

TABLE 4

| Dose | Total Motor Change | Total UPDRS Change |
| --- | --- | --- |
| 20 mg/day | −14.5% | −6.6% |
| 10 mg/day | −11.7% | −13.6% |
| 5 mg/day | −31.4% | −18.7% |

The average percent changes in plasma T4 levels for the three cohorts are given in Table 5. The relationship between dose level and percentage reduction in plasma thyroxine (T4) was direct: the higher the dose of IRX4204 the greater the decrease in T4 levels. The 20 mg/day dose of IRX4204 leads to an almost complete abrogation of plasma T4 (98.8% reduction). Interestingly, this high dose of IRX4204 is associated with the least efficacy (only a 6.6% reduction in Total UPDRS scores).

TABLE 5

| Dose | Change in TSH |
| --- | --- |
| 20 mg/day | −98.8% |
| 10 mg/day | −36.6% |
| 5 mg/day | −28.9% |

These data in a human clinical trial clearly indicate that the reduction in thyroid hormone levels upon dosing with IRX4204 negatively impacts the therapeutic benefit of IRX4204. The clinical trial data from shows an inverse relationship between suppression of the thyroid axis (manifested by suppression of TSH, thyroid stimulating hormone) and clinical improvement from baseline in total motor scores and UPDRS.

Example 12

A Human Clinical Trial to Demonstrate Effects of the Combination of IRX4204 and Thyroxine on Myelin Repair in Multiple Sclerosis Patients with Relapsing-Remitting Disease A double blinded, placebo-controlled proof of concept clinical trial of the combination of IRX4204 and thyroxine is conducted in multiple sclerosis (MS) patients to demonstrate the direct effects of IRX4204 on myelin repair in patients with relapsing-remitting MS. Patients with relapsing-remitting MS are recruited to participate in the clinical trial and are provided informed consent describing risks and potential benefits of participation. The MS patients are treated with one of several dose levels of IRX4204, ranging from 1 mg/day to 40 mg/day, such as 5 mg/day administered orally as capsules, once per day and thyroxine, administered at 12.5 µg/day to 250 µg/day orally, such as 50 µg/day. Some patients are randomized to receive a placebo dose using matching capsules, which do not contain IRX4204 or thyroxine. Patients are dosed for a minimum of 30 days, and as long as 180 days. Patients are assessed for the status of myelin damage and speed of repair of demyelination in MS lesions that occur over this period of time in their brains, spinal cords, and/or optic nerves. Quantitation of myelin damage and repair is performed at baseline and periodically through the dosing, using specialized imaging methods, which specifically examine and quantitate myelin damage and repair in these parts of the nervous system. Such methods include, but are not limited to, Positron Emission Tomography (PET) scanning, utilizing imaging agents such as the thioflavine-T derivative 2-(4'-methylaminophenyl)-6-hydroxybenzothiazole (PIB), which also binds to amyloid plaques. This compound is useful for useful for quantitating myelin repair. Alternatively, magnetic resonance imaging (MRI) using special contrast agents that bind to or enhance the appearance of areas of myelin damage or repair is utilized; or special MRI analytical algorithms, such as magnetization transfer imaging, or diffusion tensor imaging, are utilized to quantitate myelin damage and repair in the IRX4204 and thyroxine-treated patients compared to the placebo-treated patients. Dose response relationships of the IRX4204/thyroxine combination to myelin protection or repair are analyzed across the cohorts of patients treated with various dose levels of IRX4204 and thyroxine. In addition to the quantitation of myelin damage and repair by imaging methods, the clinical status of the MS patients' disease progression is preliminarily evaluated using standard clinical endpoints for MS clinical trials, such as the Expanded Disability Status Scale (EDSS). The EDSS is a 10 point scale which quantitates the MS patients' levels of disability by evaluating physical activities of daily life, such as walking, swallowing, bowel and bladder function, etc. In addition, visual acuity testing is performed to quantitate effects of the IRX4204/thyroxine combination on myelin damage and repair in the optic nerves. Substantial clinical benefit as measured by one or more of the techniques described above is observed in groups treated with a combination of IRX4204 and thyroxine compared to the vehicles combination group. Positive but less substantial clinical benefit is obtained in groups treated with a combination of IRX4204 plus thyroxine vehicle.

Example 13

A Human Clinical Trial to Demonstrate the Effects of a Combination of IRX4204 and Thyroxine Treatment on Progression of Disability in Multiple Sclerosis Patients with Relapsing-Remitting Disease A double blind, placebo-controlled, clinical trial to demonstrate evidence of benefit of IRX4204/thyroxine treatment on progression of disability in MS is conducted in MS patients with relapsing-remitting MS. Patients with relapsing-remitting MS are recruited to participate in the clinical trial and are provided informed consent describing risks and potential befits of participation. The MS patients are randomized to treatment with a dose level of IRX4204, in the range of 1 to 40 mg/day administered orally, and a dose level of thyroxine (12.5 µg/day to 250 µg/day orally) or matching placebo, for 24 months. The primary clinical efficacy outcome measure is the EDSS, a 10 point scale which quantitates the MS patients' levels of disability by evaluating physical activities of daily life, such as walking, swallowing, bowel and bladder function, etc. The clinical trial uses a sample size selected to demonstrate to a statistically significant level, a difference in change in the mean EDSS over time, of a least 1 point, between the IRX4204/thyroxine-treated group, and the placebos-treated group, at the end of 24 months of treatment. In addition, in this clinical trial visual acuity testing is performed to quantitate effects of IRX4204/thyroxine on myelin damage and repair in the optic nerves. A sample size is selected which will demonstrate to a statistically significant level, a difference in change in visual acuity over time, of a least 1 line on the standard visual acuity chart, between the IRX4204/thyroxine-treated group, and the placebo-treated group, at the end of 24 months of treatment.

Example 14

A Human Clinical Trial to Demonstrate the Effects of a Combination of IRX4204 and Thyroxine Treatment on Clinical Improvement in Parkinson's Disease A double blind, placebo-controlled, clinical trial to demonstrate evidence of benefit of IRX4204/thyroxine treatment on progression of disability in Parkinson's disease (PD) is conducted in patients who have provided informed consent describing risks and potential befits of participation. The PD patients are randomized to treatment with a dose level of IRX4204, in the range of 1 to 40 mg/day administered orally, and a dose level of thyroxine (12.5 µg/day to 250 µg/day orally) or matching placebo, for 24 months. The primary clinical efficacy outcome measure is the Unified Parkinson's Disease Rating Scale (UPDRS). The UPDRS is a rating tool to follow the longitudinal course of PD. It is made up of the 1) mentation, behavior, and mood, 2) activities of daily living (ADL) and 3) motor sections. These are evaluated by interview. Some sections require multiple grades assigned to each extremity. A total of 199 points are possible with 199 representing the worst (total) disability) and 0 indicating no disability.

The clinical trial uses a sample size selected to demonstrate to a statistically significant level, a difference in change in the mean UPDRS over time, between the IRX4204/thyroxine-treated group, and the placebo-treated group, at the end of 24 months of treatment.

Example 15

A Human Clinical Trial to Demonstrate the Effects of a Combination of IRX4204 and Thyroxine Treatment on Clinical Improvement in Alzheimer's Disease A double blind, placebo-controlled, clinical trial to demonstrate evidence of benefit of IRX4204/thyroxine treatment on progression of cognitive impairment in Alzheimer's disease (AD) is conducted in patients who have provided informed consent describing risks and potential befits of participation. The AD patients are randomized to treatment with a dose level of IRX4204, in the range of 1 to 40 mg/day administered orally, and a dose level of thyroxine (12.5 µg/day to 250 µg/day orally) or matching placebo, for 24 months. The primary clinical efficacy outcome measure is the Mini-Mental State Examination (MMSE), and optionally includes one or more of the Functional Assessment Questionnaire (FAQ), Physical Self-Maintenance Scale (PSMS), and Neuropsychiatric Inventory (NPI). The clinical trial uses a sample size selected to demonstrate to a statistically significant level, a difference in change in the mean MMSE over time, between the IRX4204/thyroxine-treated group, and the placebo-treated group, at the end of 24 months of treatment.

Example 16

Effect of IRX4204 in Parkinson's Disease Model

The purpose of this study was to evaluate IRX4204 treatment for amelioration of behavioral deficits in the rat 6-OHDA induced Parkinson Disease (PD) model. The rat model of PD was produced by unilateral intra striatum injection of the neurotoxin 6-hydroxydopamine (6-OHDA). This injection produces dopaminergic (DA) neuron loss on the injected side while sparing the contralateral DA neurons. The study design is depicted in Table 6.

TABLE 6

| Group # | Group Size | Test Item | Route | Dose Level of Test Item (mg/kg) | Dose Volume of Test Item (ml/kg) | Dosing Regimen | Testing Regimen |
|---|---|---|---|---|---|---|---|
| 1 | n = 13 | Vehicle TA1 | PO | NA | 5 | Once daily from day 4 until the end of the study (day 24) | Paw Placement/ cylinder test: Day - 1 (baseline), 3, 10, 17, and 24. |
|  |  | Vehicle TA2 | SC |  | 1 |  |  |
| 2 | n = 13 | TA1 | PO | 10 | 5 |  |  |
|  |  | Vehicle TA2 | SC | NA | 1 |  |  |
| 3 | n = 13 | Vehicle TA1 | PO | NA | 5 |  |  |
|  |  | TA2 | SC | T3: 1.5 µg/kg T4: 9 µg/kg | 1 |  |  |
| 4 | n = 12 | TA1 | PO | 10 | 5 |  |  |
|  |  | TA2 | SC | T3: 1.5 µg/kg T4: 9 µg/kg | 1 |  |  |

The paw placement (cylinder test) was used for assessment of the damage. This test assessed a rat's independent forelimb use to support the body against the walls of a cylindrical enclosure. The test took advantage of the animals' innate drive to explore a novel environment by standing on the hind limbs and leaning towards the enclosing walls.

To perform this test, rats were placed individually in a glass cylinder (21 cm diameter, 34 cm height) and wall exploration was recorded for 3 minutes. No habituation to the cylinder prior to recording was allowed.

The statistical analysis was performed as ratio between the intact and impaired legs (R/L ratio). The ratio was expressed as the values of intact right+both forelimbs divided by the values of impaired left+both forelimbs. A lower value of the ratio means greater healing of the 6-OHDA induced brain damage.

All treated animals gained weight throughout the study. The mean body weight of animals treated with the test item IRX4204 (TA1) with the vehicle of TA2 (group 2) or in combination with thyroxine and triiodothyronine (TA2; group 4) were significantly higher than the vehicle treated group (Group 1) on study days 17 and 24 (157.17±2.93% for Group 2 and 157.61±3.54% for Group 4 vs. 142.62±2.93% for the Vehicle group on day 24; p<0.05).

All animals with R/L ratio >1.5 were included in the study (ratio between the intact (R) and impaired legs (L) was expressed as the values of intact right+both forelimbs divided into the values of impaired left+both forelimbs).

Paw placement was measured prior to induction of lesion (baseline) and again 3 days after 6-OHDA injection, which was one day prior to IRX4204 treatment. Once a week during three weeks (study days 10, 17 and 24), the animals were re-tested for their performance in the paw placement test.

Animals were pre-selected based on the R/L ratio on study day 3, when the averaged ratio between the injured side and the intact side was increased relative to baseline levels (1.01±0.01 prior to surgery vs. 6.49±0.59, 3 days after surgery).

Figure 13:
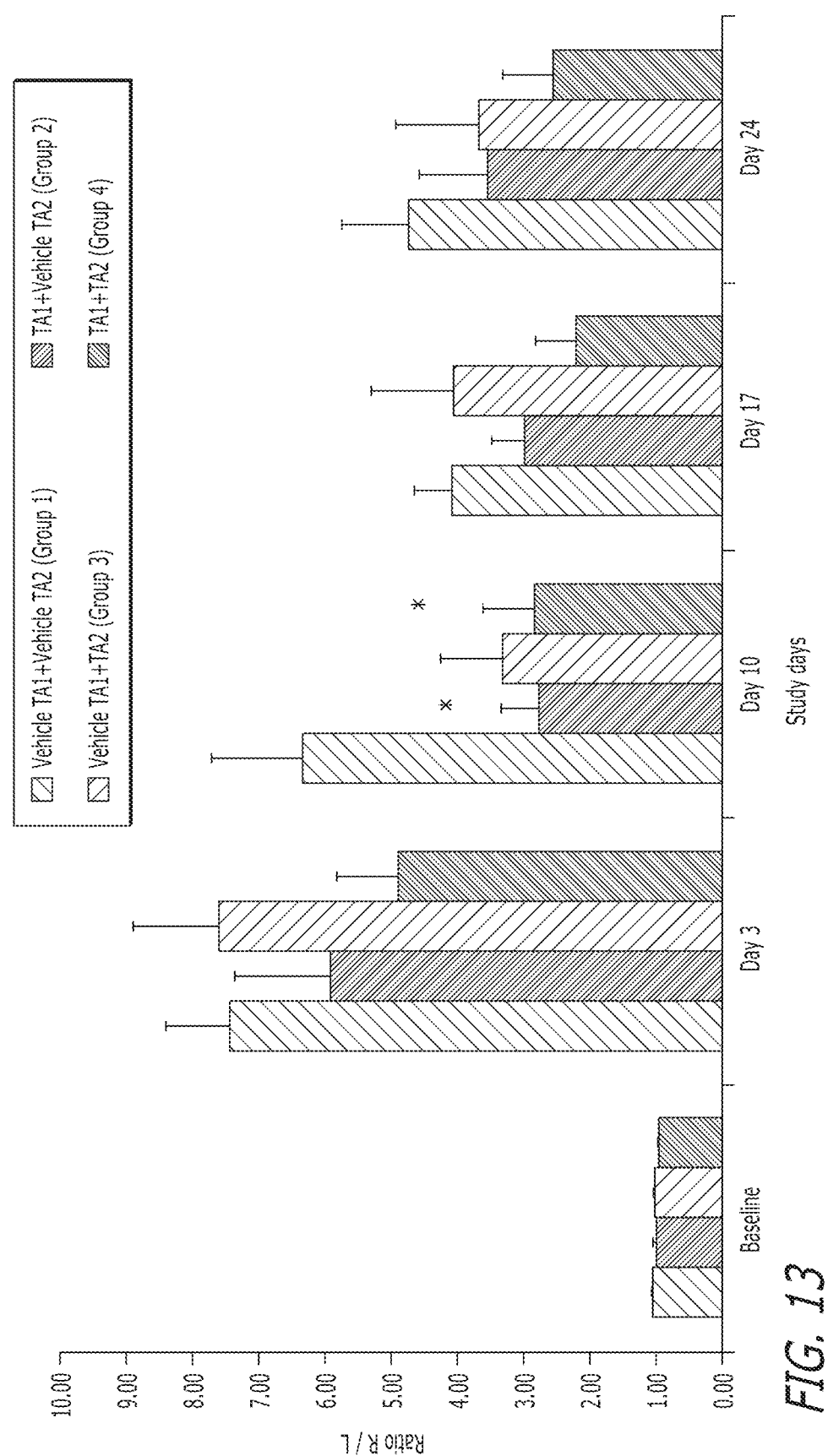
FIG. 13 depicts changes in paw placement behavior in a rat 6-OHDA-induced model of Parkinson's disease upon treatment with compounds and combinations described herein (*P<0.05 vs. vehicle using one way ANOVA followed by Dunnett test).

As shown in FIG. 13, treatment with IRX4204 (TA1) with the vehicle of TA2 (group 2) or in combination with thyroxine and triiodothyronine (TA2; group 4) significantly reduced the mean calculated R/L ratio, compared to the vehicle treated group (group 1) on study day 10 (2.76±0.57 for Group 2 and 2.86±0.76 for Group 4 vs. 6.33±1.41 for the Vehicle group; p<0.05).

The mean calculated ratio was lower in these groups compared to the vehicle group also on study days 17 and 24, however this ratio was not statistically significant.

The average value of the ratio was calculated from the four values from days 3, 10, 17 and 24. The calculated values for group 2 and group 4 are 3.79 and 3.14, respectively. This indicates that group 4 (IRX4204 in combination with thyroxine and triiodothyronine) is more effective than group 2 (IRX4204) alone.

Example 17

Mouse Oligodendrocyte Progenitor Cell Differentiation in the Presence of Vitamin D The purpose of this study was to assess possible effects of IRX4204 in combination with vitamin D, or vitamin D and triiodothyronine (T3), on differentiation of mouse oligodendrocyte progenitor cells (OPCs) into oligodendrocytes. OPCs were derived from p/p-EGFP expressing mice.

Therapeutic agents were tested in 96-well plates (6 wells per concentration). Negative and positive controls (DMSO or 10 ng/ml T3 thyroid hormone) were included in each plate. All media contained 0.1% DMSO and 0.1% EtOH. At the end of the 5-day treatment, cells were imaged on Cellomics in two channels and algorithms were used to count nuclei and EGFP+ oligodendrocytes.

Figure 14:
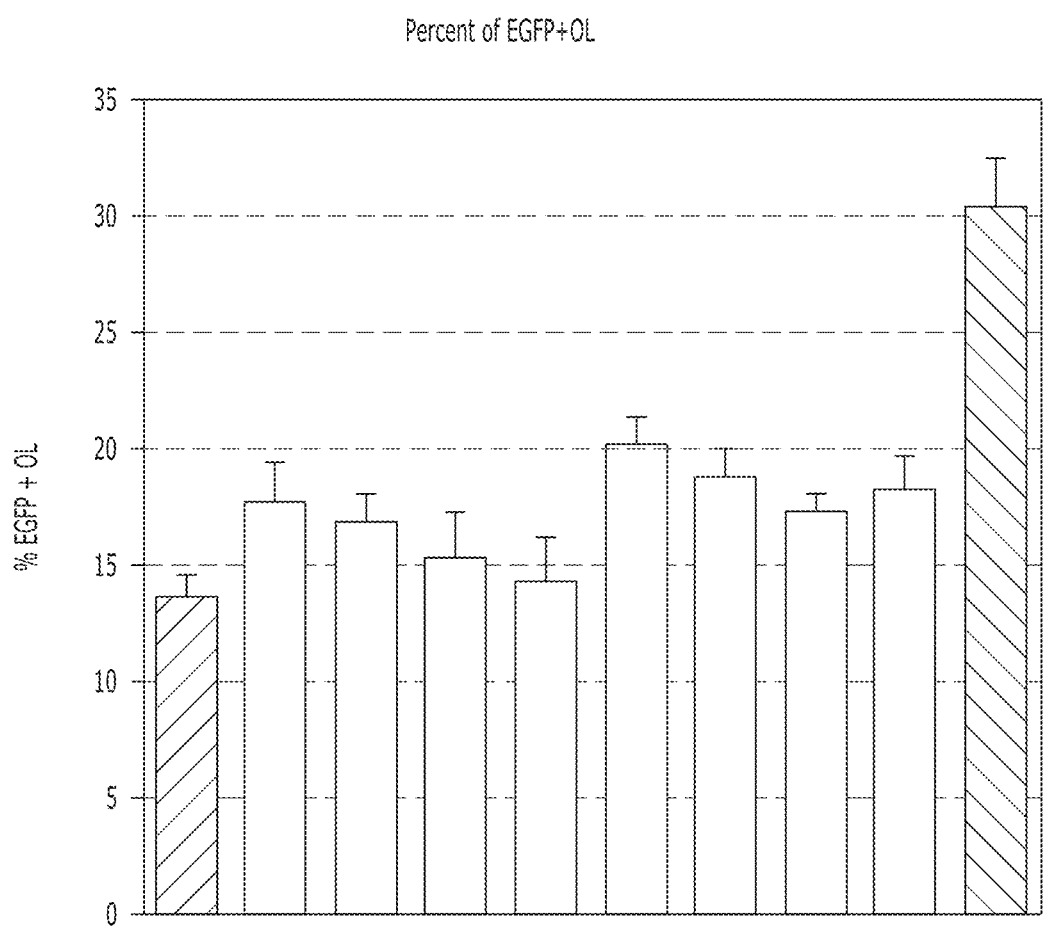
FIG. 14 depicts the percent and fold change of EGFP+ oligodendrocytes following treatment of oligodendrocytes with IRX4204, thyroid hormone, and Vitamin D (*: P<0.05, student's t-test against DMSO control; Error bar, SD).

Surprisingly, it was observed that different doses of vitamin D in combination with IRX4204 showed a negative effect in oligodendrocyte production (FIG. 14). The production of oligodendrocytes in response to a three regimen treatment (IRX4204, Vitamin D and T3) was slightly higher than that of the treatment without T3 (IRX4204 and Vitamin D). This suggests an additive effect of T3 in the three regimen combination.

Example 18

Mouse Oligodendrocyte Progenitor Cell Differentiation

The purpose of this study was to assess possible effects of IRX4204 in combination with triiodothyronine (T3), on differentiation of mouse oligodendrocyte progenitor cells (OPCs) into oligodendrocytes. OPCs were derived from plp-EGFP expressing mice.

Therapeutic agents were tested in 96-well plates (6 wells per concentration). Negative and positive controls (DMSO or 10 ng/ml T3 thyroid hormone) were included in each plate. All media contained 0.1% DMSO. At the end of the 5-day treatment, cells were imaged on Cellomics in two channels and algorithms were used to count nuclei and EGFP+ oligodendrocytes.

Figure 15A:
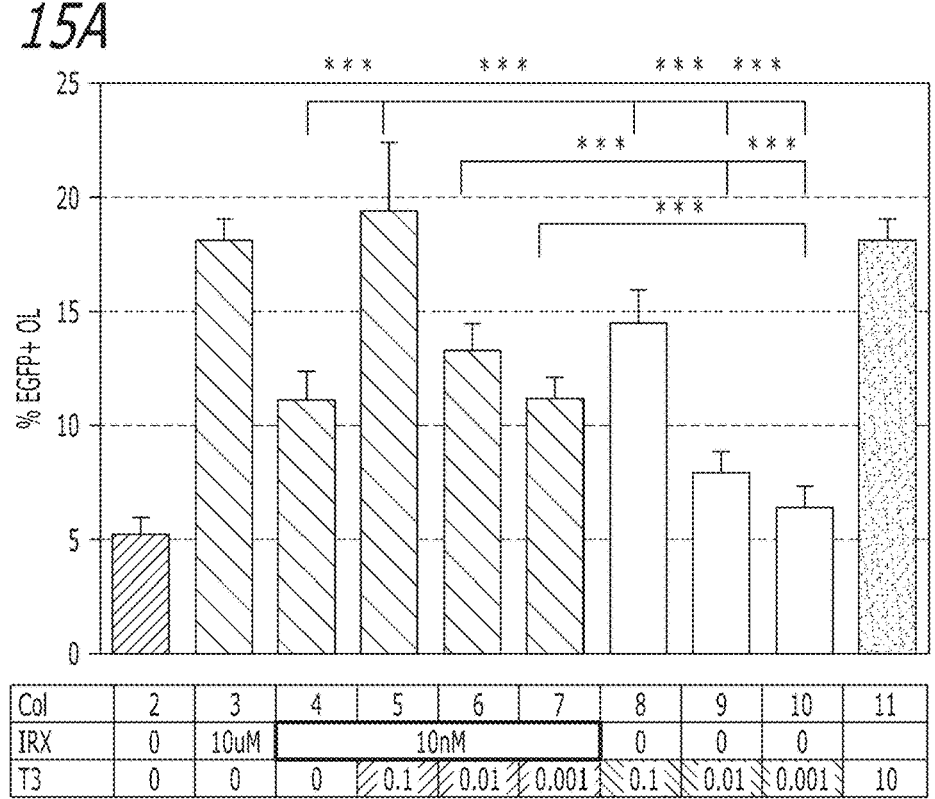
FIGS. 15A-C depicts the percent change of EGFP+ oligodendrocytes following treatment of oligodendrocytes with IRX4204 and thyroid hormone (FIG. 15A: 10 nM IRX4204.
Figure 15B:
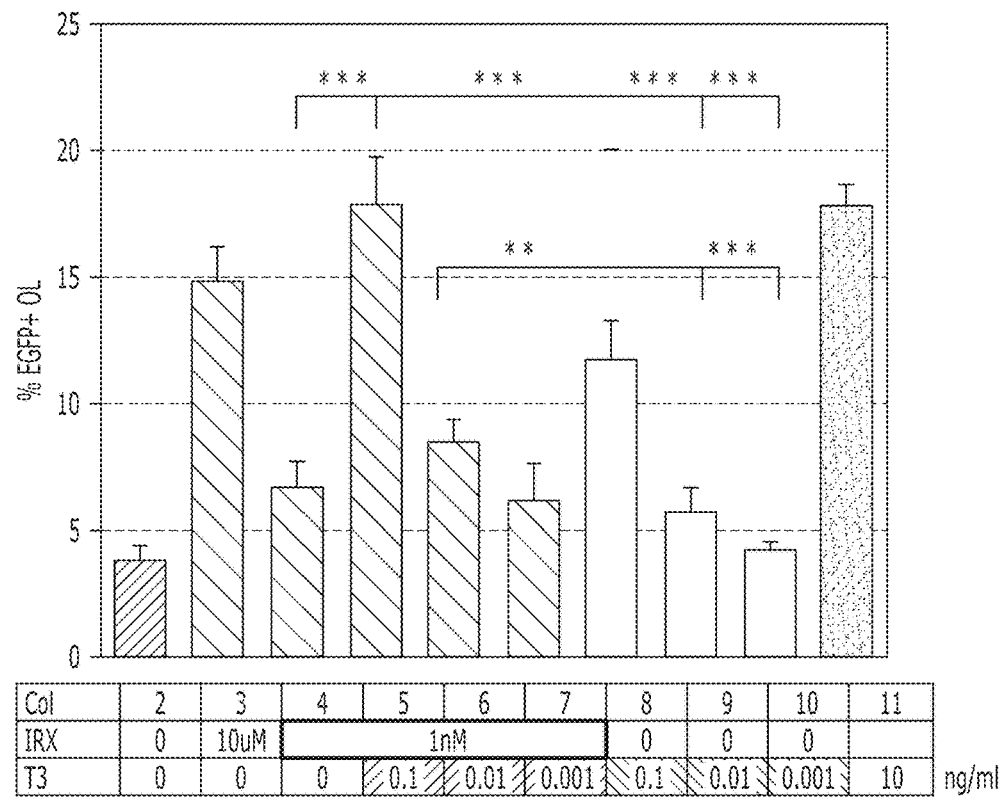
Figure 15C:
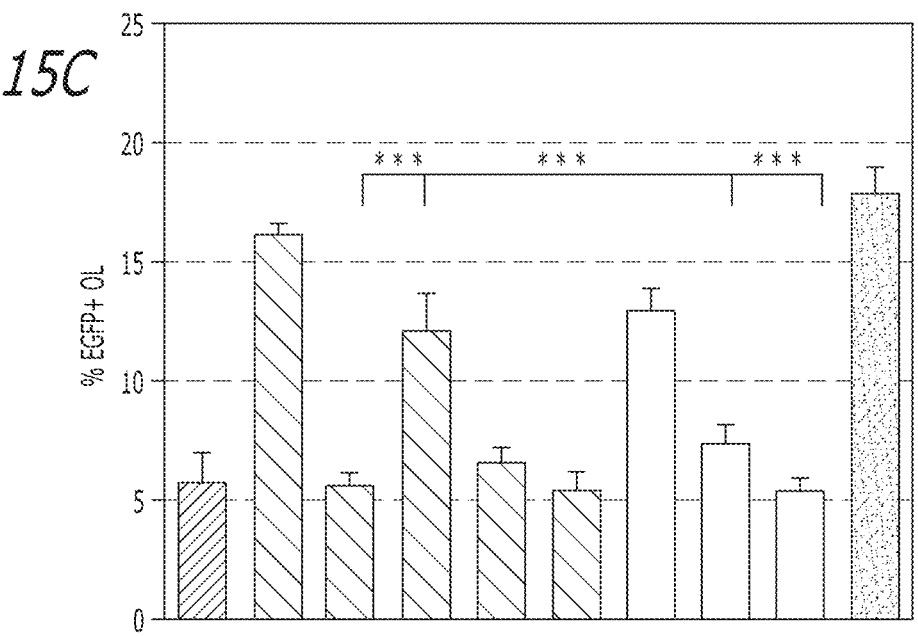

FIG. 15A-C show clear dose-responses in oligodendrocyte production in response to different doses of IRX4204 and T3. The production of oligodendrocytes in response to combination treatments of IRX4204 and T3 was more than that of individual treatment alone in all conditions. This suggests an additive, or potentially a synergistic, effect in driving oligodendrocyte precursor cell differentiation between IRX4204 and T3. Similar results were obtained when cells were stained with MBP antibody and quantified (data not shown). These data suggest that a combination of IRX4204 and T3 (or T4) will be optimal in remyelination.

Example 19

Neuroprotective Effect of IRX4204 in a Mouse Model of Demyelination

The goal of this study was to evaluate the neuroprotective effect of IRX4204 in a mouse model of non-immune mediated demyelination.

In this study, the 6-week demyelination model was used to assess neuroprotective potential of IRX4204 following 6-week concurrent treatment during demyelination. A subgroup of animals were treated with T4 along with IRX4204. The results from this study demonstrate that IRX4204 promotes neuroprotection without reducing the extent of demyelination in the corpus callosum.

Animals (8 week-old male C57BL/6J mice) were subjected to cuprizone diet plus rapamycin injections (CR) for 6 weeks to induce demyelination. Animals were treated with either vehicle or IRX4204 (10 mg/kg, PO), or IRX4204+T4 (10 mg/kg, PO, and 20 ng/g, SQ) daily for the entire 6 weeks during demyelination. All animals were sacrificed after 6 weeks of CR to evaluate axonal integrity and microglial/macrophage activity in the white matter (corpus callosum, CC). Two groups (Vehicle and IRX4204+T4) were further examined for any protective effects on the extent of myelination in the CC.

There was a significant reduction in axonal transection as shown by the decrease in the number of SMI32 positive axonal ovoids in the animals treated with IRX4204+T4. However, there was no difference in microglial/macrophage activation and the number of myelinated axons in the CC between the Vehicle and IRX4204+T4 groups. These findings support a neuroprotective role of IRX4204 mediated by a potential direct effect on demyelinated axons.

A total of 50 animals were included in the study, where 43 animals received CR demyelination for 6 weeks. During demyelination, a subset (n=7) of animals were kept on normal diet to serve as naïve age-matched controls. The remaining animals received IRX4204 (n=14) or vehicle (n=14) or IRX4204+T4 (n=15) for 6 weeks concurrently during CR. There was no mortality during the in-life phase. In addition, there were no observed health concerns during the treatment phase. All animals were alert and demonstrated proper grooming behavior. ANOVA analysis with multiple group comparison showed no significant difference in terminal body weights between IRX4204 or vehicle groups.

To assess thyroid hormone levels, terminal blood draws were taken to quantify the levels of T4. Animals treated with IRX4204 alone showed an approximate 50% decrease in T4 levels when compared to vehicle control animals. Exogenous treatment with T4 corrected the thyroid hormone levels as shown by increase in T4 levels in IRX4204+T4 group.

The floating brain sections were immunostained with SMI-32 to visualize and quantify axonal ovoids in the CC. Animals that were subjected to CR showed significantly higher numbers of SMI32 stained axonal ovoids in CC compared to naïve animals. There was a significant decrease in the number of axonal ovoids in animals treated with both IRX4204 and T4 compared to Vehicle. IRX4204 alone showed a trend towards decreased number of axonal ovoids but was not statistically different from the Vehicle.

The floating brain sections were immunostained with Iba-1 to visualize and quantify microglia/macrophages in CC. Animals subjected to CR and treated with Vehicle had a robust increase in Iba1 staining in CC compared to naïve animals. There was no difference in the levels of Iba1 staining in IRX4204 or IRX4204+T4 treated animals compared to vehicle.

Semi-thin (1 μm) sections of Epon-embedded CC tissue from animals that received CR and Vehicle or IRX4204+T4 were used to visualize and quantify the number and density of myelinated axons in the CC. Animals that received CR and vehicle demonstrated robust demyelination of the CC. There was no significant difference in the number and density of myelinated axons in IRX4204+T4 treated animals when compared to vehicle.

IRX4204 treatment alone without T4 showed a trend towards decrease in axonal ovoids, but it was statistically not different from vehicle. However, when animals that received IRX4204 were supplemented with exogenous T4 there was a significant decrease in the number of axonal ovoids compared to vehicle. This data along with our previous in vivo findings support a neuroprotective effect of IRX4204. While there was a decrease in axonal ovoids, there was no significant difference in microglial/macrophage activation and myelination in the corpus callosum in Vehicle and IRX4204+T4 groups.

The finding that IRX4204 demonstrated a neuroprotective effect only in the group with supplemental T4 suggests an enhanced effect of the combination therapy over IRX4204 alone.

Figure 20A:
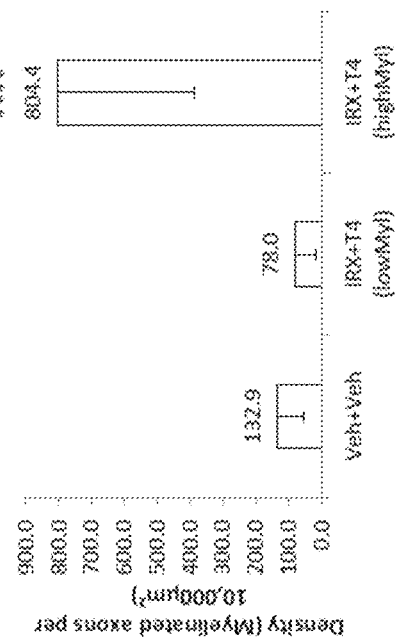
FIGS. 20A-C depicts a quantification of myelination of the corpus callosum following in vivo treatment with combinations described herein, and a separation of the data into potential responders and non-responders (one way ANOVA with Tukey's multiple comparisons, *P<0.05  P<0.01, ** P<0.001).
Figure 20B:
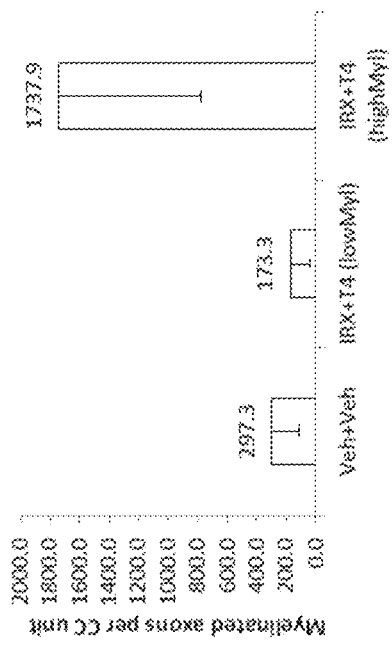
Figure 20C:
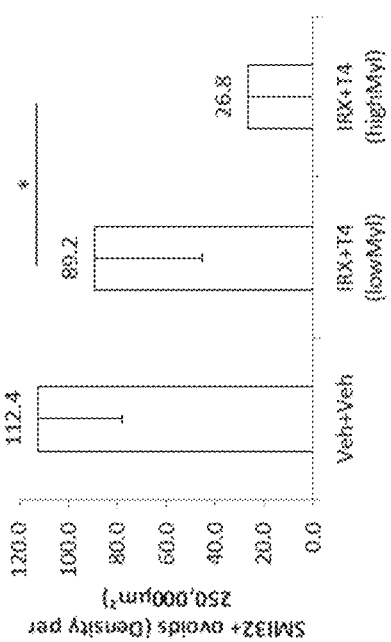

Quantification of myelinated axons in the corpus callosum shows potential responders and non-responders. FIG. 20A-C shows a high correlation between the number of axonal ovoids and myelinated axons (i.e. the animals that had very few ovoids had very high number and density of myelinated axons in the corpus callosum).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating depression-associated demyelination or neuroinflammation, the method comprising administering to a human individual in need thereof a therapeutically effective amount of a RXR agonist and a thyroid hormone, wherein administration of the combination of the RXR agonist and the thyroid hormone treats the depression in the individual, wherein the RXR agonist is 3,7-dimethyl-6(S),7(S)-methano,7-[1,1,4,4-tetramethyl-1,2,3,4-tetrahydronaphth-7-yl]2(E),4(E) heptadienoic acid, and has the structure of formula III:

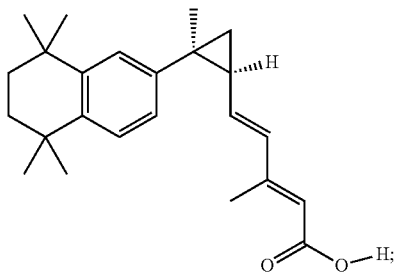

(III)

and wherein the combination of RXR agonist and thyroid hormone causes a greater improvement in the depression than the RXR agonist or thyroid hormone alone.

2. The method according to claim 1 wherein the combination of RXR agonist and thyroid hormone treats depression in the individual by both promoting remyelination and neuroprotection of neurons and modulating the individual's immune system.

3. The method according to claim 1, wherein the therapeutically effective amount of the RXR agonist is about 0.001 mg/day to about 100 mg/day.

4. The method according to claim 1, wherein the therapeutically effective amount of the RXR agonist is about 1 mg/day to about 20 mg/day.

5. The method according to claim 1, wherein the thyroid hormone is thyroxine.

6. The method according to claim 5, wherein the dose of thyroxine is about 12.5 µg/day to about 250 µg/day.

7. The method according to claim 1, wherein the RXR agonist is administered by nasal administration.

8. The method according to claim 7, wherein both the RXR agonist and thyroid hormone are administered by nasal administration.

9. The method according to claim 1, wherein the RXR agonist is administered orally.

10. The method according to claim 1, wherein the RXR agonist and the thyroid hormone are administered on the same schedule.

11. The method according to claim 1, wherein the RXR agonist and thyroid hormone are administered on different schedules.

12. The method according to claim 1, wherein the thyroid hormone is administered orally or subcutaneously.

13. The method according to claim 1, wherein treatment with the combination of RXR agonist and thyroid hormone reduces at least one symptom of depression, wherein the at least one symptom reduced is difficulty with bodily movements, problems with coordination, slow bodily movement, daytime sleepiness, early awakening, nightmares, restless sleep, fatigue, dizziness, poor balance, restlessness, amnesia, confusion in the evening hours, dementia, difficulty thinking and understanding, impaired voice, soft speech, anxiety, apathy, reduced facial expression, blank stare, or depression.

14. The method of claim 1, further comprising administration of a neurotrophic factor, or neurotrophic factor mimetic.

15. The method of claim 1, further comprising administration of a neurotrophic factor.

16. The method of claim 14, wherein the neurotrophic factor is brain-derived neurotrophic factor (BDNF), glial-derived neurotrophic factor (GDNF), nerve growth factor (NGF), neurotrophin-3 (NT-3), fibroblast growth factor, basic (bFGF), ciliary neurotrophic factor (CNTF), neurotrophic factors-4/5 (NT-4/5), insulin-like growth factor (IGF), or insulin, or a mimetic of any one of these neurotrophic factors.

17. The method of claim 14, wherein the neurotrophic factor is GDNF.

18. The method of claim 14, wherein the neurotrophic factor is insulin or insulin-like growth factor.

19. The method of claim 14, wherein the neurotrophic factor is BDNF.

20. The method of claim 14, wherein further combination with the neurotrophic factor promotes remyelination or neuroprotection.

21. The method according to claim 14, wherein therapeutically effective amount of the RXR agonist is about 0.001 mg/day to about 20 mg/day.

22. The method according to claim 14, wherein the therapeutically effective amount of the RXR agonist is about 1 mg/day to about 10 mg/day.

23. The method according to claim 14, wherein the RXR agonist is administered directly to the central nervous system.

24. The method according to claim 14, wherein the combination of RXR agonist and thyroid hormone is administered directly to the central nervous system.

25. The method according to claim 14, wherein the combination of RXR agonist, thyroid hormone, and neurotrophic factor is administered directly to the central nervous system.

26. The method according to claim 14, wherein the neurotrophic factor is administered directly to the central nervous system.

27. The method according to claim 14, wherein the thyroid hormone is administered directly to the central nervous system.

28. The method according to claim 14, wherein the neurotrophic factor is administered by nasal administration.

29. The method according to claim 14, wherein the combination of RXR agonist, thyroid hormone, and neurotrophic factor is administered by nasal administration.

30. The method according to claim 14, wherein the neurotrophic factor is administered subcutaneously or intramuscularly.

* * * * *